US006962985B2

(12) United States Patent
Palm et al.

(10) Patent No.: US 6,962,985 B2
(45) Date of Patent: Nov. 8, 2005

(54) MAMMALIAN NEURALIZED FAMILY TRANSCRIPTIONAL REGULATORS AND USES THEREFOR

(75) Inventors: Kaia Palm, Santa Monica, CA (US); Tonis Timmusk, Helsinki (FI)

(73) Assignee: CeMines, Inc., Golden, CO (US)

(*) Notice: Subject to any disclaimer, the term of this patent is extended or adjusted under 35 U.S.C. 154(b) by 462 days.

(21) Appl. No.: 09/808,387

(22) Filed: Mar. 14, 2001

(65) Prior Publication Data

US 2002/0132293 A1 Sep. 19, 2002

(51) Int. Cl.$^7$ .............................................. C07H 21/02
(52) U.S. Cl. ................. 536/23.1; 435/69.1; 435/320.1; 435/440; 435/252.3
(58) Field of Search ..................... 536/23.1; 435/69.1, 435/440, 252.3, 320.1

(56) References Cited

U.S. PATENT DOCUMENTS 4,946,778 A  8/1990 Ladner et al.
6,294,328 B1 * 9/2001 Fleischmann et al. ......... 435/6

FOREIGN PATENT DOCUMENTS

WO    WO 99/25827 A1    5/1999

OTHER PUBLICATIONS

Attachment 1: "Homology, identity, similarity, and distance".*
Price, B. D. et al. (1993) The Drosophila neuralized gene encodes a C3HC4 zinc finger. EMBO J. vol. 12, pp. 2411–2418.*
Nakamura, H. et al. (1998) Identification of a human homolog of the Drosophila neuralized gene within the 10q25.1 malignant astrocytoma deletion region. Oncogene. vol. 16, pp. 1009–1019.*
Yeh, E. (2000) Neuralized functions cell autonomously to regulate Drosophila sense organ development. EMBO J., vol. 19, pp. 4827–4837.*
Guy, C. T. (1996) Activated neu induces rapid tumor progression. J.. Biol Chem. vol. 271, pp. 7673–7678.*
Aguilera, et al., *Genetics,* 155(3):1231–44 (1996).
Artavanis–Tsakonas et al., *Science,* 284:770–776 (1999).
Beatus & Lendahl, *J Neurosci Res,* 54:125–136 (1998).
Boulianne et al., *EMBO J,* 10:2975–2983 (1991).
Boulikas, *J Cell Biochem,* 60:61–82 (1996).
Campos–Ortega & Jan, *Annu Rev Neurosci,* 14:399–420 (1991).
Carballo et al., *Science,* 281:10011005 (1998).
Chiaramello et al., *J Biol Chem,* 271:22035–22043 (1996).
Chuang, et al., *Biochem Biophys Res Commun,* 18:235(2)317–20 (1997).
Cole et al., *Monoclonal Antibodies and Cancer Therapy,* Alan R. Liss Inc, New York N.Y., pp 77–96 (1985).
Corbin et al., *Cell,* 311–323 (1991).
Cote et al, *Proc Natl Acad Sci,* 80:2026–2030 (1983).
Datta, et al., *Genes and Dev,* 13:2905–27 (1999).
Engvall, E., *Meth Enzymol,* 70:419 (1980).
Fornerod et al., *Cell,* 90:1051–1060 (1997).
Freemont, *Ann NY Acad Sci,* 684:174–192 (1993).
Freemont, *Biochem J.,* 278:1–23 (1991).
Fukuda et al., *Nature,* 390:308–311 (1997).
Glass and Rosenfeld, *Endocr Rev.* 21:447 (2000).
Guzovsky et al., *Nat Neurosci,* 2:1120–1124 (1999).
Harentstein et al., *Development,* 116:1203–1220 (1992).
Hood and Silver, *Curr Opin Cell Biol,* 241–247 (1999).
Huse W.D. et al., *Science,* 256:1275–1281 (1989).
Izaurralde and Adam, *RNA,* 4;351–364 (1998).
Jarriault et al, Letters to Nature 1995, ********* Ohtsuka et al., (1999).
Jaye et al., *Nucl. Acid Res.,* 11:2325, (1983).
Kageyama et al., *Int J Biochem Cell Biol,* 29:1389–1399 (1997).
Kang et al., *J. Biol. Chem,* 274, 8570–8576 (1999).
Kanno et al., *EMBO J.,* 15;14(22):5672–8 (1995).
Keller et al., *Dev Biol,* 181:197–212 (1997).
Keller et al., *Dev Biol,* 202:157–171 (1998).
Klebler and DesGroseillers, *Neuron,* 25:19–28 (2000).
Kitada, et al., *Nature,* 392(6676):605–8 (1998).
Knoepfler and Eisenman, *Cell,* 99:447–450 (1999).
Koehler and Milstein, *Nature,* 256:495–497 (1975).
Kogerman et al., *Nat Cell Bio,* 1:312–319 (1999).
Kozbor et al., *Immunol Today,* 4:72 (1983).
Kudo et al., *Exp Cell Res,* 242:540–547 (1998).
Kudo et al., *Proc Natl Acad Sci* USA, 96:9112–9117 (1999).
Kuhl and Skehel, *Curr Opin Neurobiol,* 8(5):600–6 (1998).
Kuroda et al., *J Biol Chem,* 274:7238–7244 (1999).
Leveillard and Wasylyk, *J Biol Chem,* 272:30651–30661 (1997).

(Continued)

*Primary Examiner*—Karen Cochrane Carlson
*Assistant Examiner*—Samuel W. Liu
(74) *Attorney, Agent, or Firm*—Dorsey & Whitney LLP; Todd A. Lorenz

(57) ABSTRACT

The disclosure relates to isolated polynucleotides and purified polypeptides of the Neu family of proteins, which have been shown to demonstrate transcriptional regulatory activity. For example, the purified polynucleotide can encode a Neu polypeptide, wherein the Neu polypeptide comprises at least one neuralized homology repeat domain and a C3HC4 RING-zinc finger domain is disclosed. A purified Neu polypeptide, wherein the Neu polypeptide comprises at least one neuralized homology repeat domain and a C3HC4 RING-zinc finger domain is disclosed. Antibodies capable of specifically binding to the disclosed Neu polypeptides are disclosed. Vectors expressing the disclosed Neu protein coding regions and host cells containing the vectors are disclosed. Methods of making the Neu proteins disclosed are also provided, as are method of identifying binding partners that interact with a Neu protein family member.

15 Claims, 15 Drawing Sheets

OTHER PUBLICATIONS

Lewis, *J Curr Opin Neurobiol,* 6:3–10 (1996).
Lieber, *Genes Dev,* 7:1949–1965 (1993).
Liu et al., *Proc Natl Acad Sci USA,* 95(18):10626–31 (1998).
Maldonado et al., *Cell,* 99:455–458 (1999).
Mannervik et al., *Science,* 284:606–609 (1999).
Metsis et al., *Gene,* 121:247–254 (1992).
Miki et al, *Science,* 266(5182):66–71 (1994).
Morrison et al., *Proc Natl Acad Sci,* 81:6851–6855 (1984).
Mowery–Rushton et al., DNA methylation patterns in human tissues of uniparental origin using a zinc–finger gene (ZNF127) from the Angelman/Prader–Willi region *Am J Med Genet,* 61(2):140–6 (1996).
Nakamura et al., *Oncogene,* 16(8):1009–1019 (1998).
Neuberger et al., *Nature,* 312:604–608 (1984).
Nishi et al., *J Biol Chem,* 269:6320–6324 (1994).
Orlandi et al., *Proc Natl Acad Sci* 86: 3833–3837 (1989).
Ouchterlony, O. et al., Chap. 19 in :*Handbook of Experimental Immunology,* D. Wier (ed) Blackwell (1973).
Pao et al., *Proc Natl Acad Sci USA,* 97:1020–1025 (2000).
Price et al., *EMBO J,* 12:2411–2418 (1993).
Redmond et al., *Nat Neurosci,* 3:30–40 (2000).
Reeben et al., *J Neurosci Res,* 40:177–188 (1995).
Rossner, et al., *Mol Cell Neurosci,* 10(3–4):460–475 (1997).
Saurin et al., *Trends Biochem Sci,* 21:208–214 (1996).
Schuman, *Neuron,* 23:645–8 (1999).
Sestan et al., *Science,* 286:741–746 (1999).
Shain et al., *Nucleic Acids Res,* 23:1696–1703 (1995).
Simpson, *Neuron,* 15:739–742 (1995).
Steward et al., *Neuron,* 21:741–51 (1997).
Taagepera et al., *Proc Natl Acad Sci USA,* 95:7457–7462 (1998).
Tabara et al., *Development,* 126(1):1–11 (1999).
Takeda et al., *Nature,* 314:452–454 (1985).
Tanabe & Jessell, *Science,* 274:1115–23 (1996).
Tiedge et al., *Science,* 283:186–7 (1999).
Timmusk et al., *Neuron,* 10:475–489 (1993).
Ullman et al., *Cell,* 90:967–970 (1997).
Vaitukaistis, J. et al., *J. Clin. Endocrinol. Metab,* 33:988–991 (1971).
Valdez et al., *Biochem Biophys Res Commun,* 234(2):335–40 (1997).
Wallace et al., *Nucl. Acids Res.,* 9:879 (1981).
Wang et al., *Mech Dev,* 58(1–2):203–15 (1996).
Winter G. and Milstein C; *Nature,* 349:293–299 (1991).
Wu et al., *Mech Dev,* 65(1–2):3–17 (1997).
Xio et al., *Curr Opin Neurobiol,* 10:370–74 (2000).
Yamaga et al., *J Biol Chem,* 274:28537–28541 (1999).
Yoneda, *Cell Struct Funct,* 25:205–208 (2000).
Crabtree, Gerald R., *Cell,* vol. 96, 611–614, (1999).
Fesquet, Didier, et al., Oncogene, vol. 15, 1303–1307, (1997).
Sestan, Nenad, et al., Science, vol. 288, 741–746, (1999).
Torchia, Joseph, et al., Curr. Opin. Cell Biol., vol. 10, 373–383 (1998).
International Search Report—Date of mailing: Dec. 30, 2002; re International Appln. No. PCT/US02/07201; International Filing Date: Mar. 8, 2002.
Tatematsu, K. et tal., "Transcriptional activity of RBCK1 protein (RBCC protein interacting with PKC 1): requirement of RING–finger and B–Box motifs and regulation by protein kinases.", Biochem Biophys Res Commun., vol. 247, pp. 392–396 (Jun., 1998).
Capili, A.D. et al., "Solution structure of the PHD domain from the KAP–12 coreprocessor: structural determinants for PDH, RING and LIM zinc–binding domains" *The EMBO J.,* vol. 20, pp. 165–177 (Jan. 2001).
NCI/Ninds–CGap, (Direct Submission), NCBI Accession No. AI571301 (GI No. 4536745), Mar. 31, 1999.
Zhou, L. et al., (Direct Submission), NCBI Accession No. Q24746 (GI No. 34222692), Oct. 10, 2003.
Zhou, L., et al., "Comparison of the *neuralized* genes of *Drosophila virilis* and *D. melanogaster,*"Genome 37(5):840–847 (Oct. 1994).

* cited by examiner

```
h1I     FHPHTKGSOLMDLSHKAVKR-QASFCNAIFSNRPVLIYEOVRHKHTKKQCCWSGHRL
h2I     FHAQAKGKNVRLDGHSRRATR-RNSFCNGVTFLORPIRLYEOVRLRLVAVRPGWSGHRI
h3      FHAEAKGAOVRLDTRGCIAHR-RTTFHDGIVFSORPVRLGERVALRVLREESGWCGGIRV
dI      FHS-VHGDNERISRDGTLRRR-FESFCRAIFSARPVRINERLCVKHAEISNNWNGGIR
dII     FHNTK-GRNVRLSQDRFVASRTESDFCQGYVFTARPIRIGEKLIVQVLKTEQMYVGALAL
h2II    FHATR-GPDVSESADRKVACAPRPDGGRTLVFSERPLRPGESLFVKVGRPGLAAPGAEA
h1II    FHALRAGAHVRLLDEQTVARVEHGRDERALVFISRPVRVAELIFVKVTRSGGARPGATSF h1I     GITSKLPSRLHPDSLPKYACPDLVSOSGFVAKAL-PEEFANEGNILAFWVDKKGRVFHRI
h2I     GITAHLPSLMSAQDIPKYACPDLVTRPGYVAKAL-PENLALRDTVLAYWADRHGRVFYSV
h3      GITRLPPACVSVPSLPPFLCPDLEESPTVAAVL-PEGCALTGDLVRFWVDRRGCFAKV
dI      GITSNLPVTLEG-TLPKYACPDLTNLPGFVAKAL-HEQYCEKDNILYYYVNGAGDVIYGI
dII     GITSCNPAMLQP-NDLPNDSDFLLDRPEYLVVSKDIAAAPQRGDELAFFVAPNGEVSISK
h2II    GITSCLPGVLRP-NELPADPDALLDRKEYLVVAR-AGPVPSGGDALSFTLRPGGDVLLGI
h1II    GVTTCLPGTLRP-ADLPFSPEALVDRKEFLAVCR-VPGPLHSGDILGLVVNADGEHLSH h1I     NDSAVMLFFSGVRTADPLWAVDVYG-LTRGVQLH
h2I     NDGEPVLFHCGVAVGGPLWAIDVYG-ITDEVQLH
h3      NAGCRLLLREGVPVGAPLWAVDVYG-TTKAIELH
dI      NNEEKGVILTGSDTRSLLWTVIDIYG-NCTGLRLH
dII     NNGPAVVVMH-VDQSLQLWAIDVYG-STQSLRVK
h2II    NGRPRGRLLC-VDTTQALWALAVRGGVAGQLRLH
h1II    NGAAAGMQLC-VDASQPLWMLGLFG-TITQLRLH
```

FIGURE 12

MAMMALIAN NEURALIZED FAMILY TRANSCRIPTIONAL REGULATORS AND USES THEREFOR

BACKGROUND OF THE INVENTION

1. Field of the Invention

The described invention relates to the family of mammalian Neuralized (neu) genes, proteins encoded by those genes (Neu), expression patterns of the gene family, their function as a transcriptional regulator, and the proteins with which the Neu family of proteins interacts. Additionally, therapeutic and diagnostic uses for the Neu family of proteins and agents that bind thereto are also provided.

2. Description of the Related Art

Development and functioning of the nervous system requires orchestrated action of thousands of transcriptional regulators. Balance between transcriptional activators and repressors determines the spectrum of expressed genes. The molecular basis of the initial stages of neurogenesis as well as several aspects of neuronal differentiation have been extensively studied. As a result, a variety of transcriptional activators and repressors have been discovered and characterized. Our understanding of these systems and their component interactions, however, is far from complete. Little is known about the molecular mechanisms that support neuronal circuits in developing and mature nervous systems or the molecular mechanisms that coordinate maintenance of the differentiated state.

The process of lateral inhibition prevents neighboring cells from developing into the same type of differentiated cells in flies and in vertebrates. See Tanabe & Jessell, *Science*, 274:1115–23 (1996). In *Drosophila*, a group of mutations has been described that shows severe defects in the process of lateral inhibition in the developing nervous system. These neurogenic mutations result in hyperplasia of the neural tissue at the expense of epidermal structures. See Campos-Ortega & Jan, *Annu Rev Neurosci*, 14:399–420 (1991). The temporal and spatial expression patterns of neu are compatible with its function as a neurogenic gene in *Drosophila*. The Neu protein is expressed throughout the ectoderm at the time when cell fate is determined and its expression proceeds in neuroblasts. See Boulianne, et al., *EMBO J*, 10:2975–2983 (1991). neu expression has been detected in actively proliferating neuroblasts in several regions of the central nervous system (CNS) and peripheral nervous system (PNS). Expression of neu in imaginal disc suggests that it is also involved in later stages of development. The neu gene encodes a RING finger (C3HC4) type zinc finger protein. The molecular function of the *Drosophila* Neu protein is unknown. Interestingly, it was discovered that EST databases contain a homologue of Neu suggesting that a family of Neu-like proteins is present in *Drosophila*.

Current studies of the brain development in *Drosophila* and vertebrates, indicate that many basic molecular and genetic mechanisms involved in neurogenesis are highly conserved. During development of the nervous system, neural cell specification is acquired through the series of progressive restrictive steps. In *Drosophila*, neural precursors are first specified by proneural genes including basic helix-loop-helix (bHLH) transcription factors of atonal and achaete-scute complex. Simpson, *Neuron*, 15:739–742 (1995). The process of lateral inhibition, which further restricts the developmental potential of neuroectodermal cells is regulated by neurogenic genes such as Notch, mastermind, big brain, Delta, Enhancer of split, and neuralized. Analysis of the function of these neurogenic loci in the *Drosophila* embryo has revealed that mutations in any of these genes result in hyperplasia of neural tissue at the expense of epidermal structures and also cause defects in tissues derived from mesoderm and endoderm. Campos-Ortega and Jan, *Annu. Rev Neurosci*, 14:399–420 (1991); Harentstein et al., *Development*, 116:1203–1220 (1992). Vertebrate homologues of Notch, Delta and the proneural/neurogenic genes of atonal, achaete-scute, hairy, and Enhancer of Split complex have been identified and recent work, mostly in Xenopus and mouse, suggests that their role in neurogenesis is conserved. Lewis, *Curr Opin Neurobiol*, 6:3–10 (1996); Kageyama et al., *Int J Biochem Cell Biol*, 29:1389–1399 (1997); and Beatus, Lendahl, *J Neurosci Res* 54:125–136 (1998). For example, postnatal Notch signaling affects the elaboration of different body systems and regulates plasticity of cortical postmitotic neurons. Artavanis-Tsakonas et al., *Science*, 284:770–776 (1999); Redmond et al., *Nat Neurosci*, 3:30–40 (2000); and Sestan et al., *Science*, 286:741–746 (1999).

The last few years have brought the identification and characterization of many new key regulators of vertebrate neurogenesis. Recently, a human homologue of *Drosophila* Neu gene was isolated and its expression in the adult nervous system and in tumors of neuroectodermal origin, such as astrocytomas, was characterized. Nakamura, et al., *Oncogene* 16(8):1009–1019 (1998). Nakamura and others (1998) hypothesized that h-neu1 plays a role in determination of cell fate in the central nervous system and may act as a tumor suppressor which inactivation could be associated with malignant progression of astrocytic tumors. A homology search in human, rat, and mouse EST databases revealed three new mammalian Neu homologs, suggesting that a family of Neu-like proteins exists in mammals.

SUMMARY OF THE INVENTION

The disclosure relates to isolated polynucleotides and purified polypeptides of the Neu family of proteins, which have been shown to demonstrate transcriptional regulatory activity. For example, the purified polynucleotide can encode a Neu polypeptide, wherein the Neu polypeptide comprises at least one neuralized homology repeat domain and a C3HC4 RING-zinc finger domain is disclosed. A purified Neu polypeptide, wherein the Neu polypeptide comprises at least one neuralized homology repeat domain and a C3HC4 RING-zinc finger domain is disclosed. Antibodies capable of specifically binding to the disclosed Neu polypeptides are disclosed. Vectors expressing the disclosed Neu protein coding regions and host cells containing the vectors are disclosed. Methods of making the Neu proteins disclosed are also provided, as are methods of identifying binding partners that interact with a Neu protein family member.

BRIEF DESCRIPTION OF THE DRAWINGS

FIG. 12 shows alignment of neuralized homology repeat domains of human Neu1, Neu2, and Neu3 proteins.

DETAILED DESCRIPTION OF THE PREFERRED EMBODIMENTS

Figure 1:
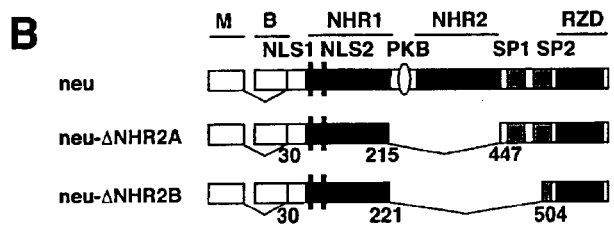
FIG. 1 shows (A) the amino acid sequences of neu1 proteins in mouse, rat, Drosophila and human, and (B) the primary structure of neu1 protein isoforms in mouse and rat.

The invention described herein relates to the identification of members of the Neuralized (neu) family of genes and their respective proteins, and aspects of their structure and function as transcriptional regulators. The invention relates to the characteristics of mammalian neu gene family's conserved structural motifs, related function as transcriptional regulators, and functional features of the family relating to expression patterns and potential interactions with interaction-partners, providing tools with which to explore the Neu-related regulatory cascades that operate in neurons and other cell types.

Structure

The invention described herein relates to the neuralized (Neu) family of transcriptional regulators that contain a C-terminal C3HC4 RING zinc finger and at least one neuralized homology repeat domain. The term "neuralized" (or "Neu"), as used herein, includes all members of the Neu family such as Neu1, Neu2, Neu3, Neu4 coding sequences and proteins. These proteins belong to a family of proteins that share C-terminal C3HC4 RING zinc finger and at least one neuralized homology repeat domain. Neuralized homology repeat domains represent a novel class of transcription repression domains that regulate transcription of a large number of genes.

The C3HC4 RING-zinc finger motif is a cystine-rich amino acid sequence motif found in the sequence of the human RING gene. Freemont, et al., *Biochem J*, 278:1–23 (1991); Freemont, *Ann NY Acad Sci*, 684:174–192 (1993). The motif can be described as C—$X_2$—C—$X_{(9-27)}$—C—$X_{(1-3)}$—H—$X_2$—C—$X_2$—C—$X_{(4-48)}$—C—$X_2$—C, where C is a cysteine, H is a histamine, and X can be any amino acid. This family includes genes that are involved in the regulation of development, differentiation, apoptosis, oncogenesis, and membrane trafficking.

Several isolated and characterized RING-zinc finger proteins have proposed roles in gene regulation. Although the precise function of the RING-zinc finger domain is unknown, indirect data demonstrates that the RING-zinc finger domain could function as a DNA-binding or protein-protein interaction domain. These two functions are related. Several transcriptional repressors which act as dimers have been characterized. Their structures comprise both dimerization and DNA-binding surfaces. For example, well known transcriptional regulators that contain RING-zinc finger domains are BRCA1 (Miki et al., *Science*, 266(5182):66–71 (1994)) and MEL18 (Kanno et al., *EMBO J*. 15;14(22):5672–8 (1995)), a polycomb group-related transcriptional regulator.

Function and Interactions

Neu Function as a Transcriptional Regulator

Mammalian Neu1 acts as a powerful transcriptional repressor in transient expression assays and silences both TATA-containing and TATA-less promoters, including the promoters of the nerve growth factor (NGF), brain-derived neurotrophic factor, neurofilament light chain, and growth-associated protein-43 genes. Neuralized homology repeat domains (NHRs) function as transcription repression domains, suggesting that NHR-containing proteins represent a novel class of transcriptional repressors. It is likely that mammalian Neu1 mediates transcriptional repression through protein-protein interactions. Like several known repressors, mammalian Neu1 could function through interaction with co-repressors such as dCtBP or mammalian homologues of Groucho, and general repressor complexes, such as NC2, Mot1, or Not to interfere with the function of Pol II complex. See Maldonado et el., *Cell*, 99:455–458 (1999) and Mannervik et el., *Science*, 284:606–609 (1999). Alternatively, repression could be achieved through chromatin remodeling by recruiting the histone deacetylase complexes (HDACs). See Glass and Rosenfeld, *Endocr Rev*, 21:447 (2000); Knoepfler and Eisenman, *Cell*, 99:447–450 (1999); and Torchia et al., *Curr Opin Cell Biol*, 10:373–383 (1998). Current data suggest that the mechanism of Neu1 repression does not include a HDAC complex in neuroblastoma Neuro2A cells, as the HDAC inhibitor trichostatinA did not relieve m-Neu1-mediated repression in these cells.

Neu is a Shuttling Protein with Dominant Cytoplasmic Localization as a Result of a Nuclear Import Combined with an Efficient Export A putative nuclear localization signal (NLS) has been identified in the N-terminus of d-Neu, however, the NLS sequence identified in d-Neu is not conserved in mouse, rat and human Neu proteins. See Boulianne et al., *EMBO J*. 10:2975–2983 (1991) and Price et al., *EMBO J*, 12:2411–2418 (1993). The weak NLS sequences (HKAVKR (SEQ ID NO: 43), RLKITKK (SEQ ID NO: 44)), that were identified in mammalian Neu1 proteins, have been suggested to regulate nuclear import of a fraction of the synthesized protein. See Boulikas, *J Cell Biochem*, 60:61–82 (1996). Indeed, m-Neu1 resides both in the cytoplasm and in the nucleus, revealing that it is the subject of regulated nuclear import. Recent studies have shown that importin-α family members are involved in the formation of the NLS receptor complexes that govern the protein transport to the nucleus. See Ullman et al., *Cell*, 90:967–970 (1997); and Izaurralde and Adam, *RNA*, 4:351–364 (1998). Interestingly, importin-α3 was identified here as one of the m-Neu interacting proteins by yeast two-hybrid screening. Furthermore, the results discussed herein also demonstrate that the CRM1/exportin1-related export pathway controls the nucleocytoplasmic shuttling of Neu1, since the nuclear export of a tagged-m-Neu1 fusion protein is blocked by LMB. LMB is a microbial metabolite that inactivates the nuclear export by interfering with the binding of CRM1/exportin1 to the nuclear export signals. See Fornerod et al., *Cell*, 90:1051–1060 (1997); Kudo et al., *Exp Cell Res*, 242:540–547 (1998); Kudo et al., *Proc Natl Acad Sci USA*, 96:9112–9117 (1999); Fukuda et al., *Nature*, 390:308–311 (1997); and Nishi et al., *J Biol Chem*, 269:6320–6324 (1994). These data reveal that mammalian Neu1 function is additionally regulated by nucleocytoplasmic shuttling.

Neu Function as a Calcium-Signal Transducer

Transcriptional activity of Neu is controlled by calcium ($Ca^{2+}$) signaling that regulates Neu translocation into the nucleus where Neu acts as a transcriptional repressor. It has been long known that intracellular calcium controls a variety of brain- and muscle cell functions. Since $Ca^{2+}$ levels regulate nucleocytoplasmic shuttling of transcription factors (Crabtree, *Cell*, 96:611–614 (1999)), Neu proteins could function as mediators of calcium signaling to the nucleus to regulate gene expression. There is evidence that in *Drosophila* and also in vertebrates, ligand activated Notch is subjected to proteolytic cleavage and transported to the nucleus where it acts as a transcriptional regulator (Jarriault et al 1995; Ohtsuka et al., 1999). Interestingly, recently it was shown that d-neu protein is associated primarily with the plasma membrane (Yeh et al., 2000). This, however, does not exclude the possibility that Neu1, like Notch, may be localized also within the nucleus. Based on current knowledge it is hypothesized that Neu1 functions as a mediator of an extracellular signal from the plasma membrane to the nucleus to regulate gene expression. According to one possible scenario, Neu1 is posttranslationally modified in a signal ($Ca^{2+}$)-dependent fashion and subsequently translocated into the nucleus, where it functions as a transcriptional regulator.

Neurogenic Function of Neu.

*Drosophila* neuralized (d-neu) and h-neu1 genes encode homologous (~40%) proteins with a C-terminal C3HC4 RING zinc finger domain (RZD) and one or two neuralized homology repeat (NHR) domains. Boulianne et al., *EMBO J*, 10:2975–2983 (1991) and Price et al., *EMBO J*, 12:2411–2418 (1993). d-neu is expressed in the ectoderm at the time when cell fate is determined, implying the role of Neu in neurogenesis. Boulianne et al., *EMBO J*, 10:2975–2983 (1991).

In *Drosophila*, d-neu expression has been detected earliest in the ectoderm continuing later in neuroblasts. Boulianne et al., *EMBO J*, 10:2975–2983 (1991). Since developing mouse CNS can be divided into regions that express either high or low levels of neu1, and as neu1 is not expressed in proliferating regions of the nervous system, it suggests that other neu-related genes function in a fashion complementary to neu1. Indeed, based on the recent findings we could argue that neu1 defines a new gene and protein family consisting of at least two *Drosophila* and four mammalian genes.neu2, second member of mammalian neu family of genes, is expressed at high levels in the embryonic brain, whereas the expression levels decrease during postnatal development. Recent studies of the brain development in *Drosophila* and vertebrates, indicate that many basic molecular and genetic mechanisms involved in neurogenesis are highly conserved. Lewis, *J Curr Opin Neurobiol*, 6:3–10 (1996); Kageyama et al., *Int J Biochem Cell Biol*, 29:1389–1399 (1997); and Beatus & Lendahl, *J Neurosci Res*, 54:125–136 (1998). For example, postnatal Notch signaling affects the elaboration of different body systems and regulates plasticity of cortical postmitotic neurons. Artavanis-Tsakonas et al., *Science*, 284:770–776 (1999); Redmond et al., *Nat Neurosci*, 3:30–40 (2000); and Sestan et al., *Science*, 741–746 (1999).

Earlier genetic studies in *Drosophila* suggested that delta, mastermind, big brain, and neuralized refine a signal upstream of notch and that mastermind functions upstream of all the other neurogenic genes. Carnpos-Ortega and Jan, *Annu Rev Neurosci*, 14:399–420 (1991); and Lieber, *Genes Dev*, 7:1949–1965 (1993). Therefore, if the function of the mammalian Neu family of proteins is conserved in conjunction with other neurogenic factors, mammalian neu genes refine the signal upstream of mammalian homologues of notch and downstream of mastermind in tissues where neu genes are expressed, particularly in developing nervous system. Given that mammalian neu mRNAs encode different protein isoforms, complex regulatory circuits implicating various Neu family members are expected in different tissues. The transcription repression activities of mammalian Neu could well-explain its function as a neurogenic gene.

Neu Role in Cell Signalling and Synaptogenesis

Suppression of gene expression plays an important role in the maintenance and stability of a mature nervous system. It is essential to suppress neurite growth and extensive formation of new axons and dendrites in the adult functional nervous system and to maintain neurons in their differentiated state. Transcriptional repressors are involved and play a crucial role in the silencing of the neurite growth program.

Mammalian neu1 shows most prominent expression in the postnatal central nervous system, revealing its function in postnatal development. neu1 mRNA expression levels increase significantly during the early postnatal development when active synaptogenesis takes place, to reach the peak levels in the adult animal. In the adult mammalian CNS, the highest expression levels of neu1 assign to the neurons of hippocampus, cerebral cortex, striatum, and amygdala. Whereas several brain regions such as thalamus/hypothalamus, midbrain, medulla, and also the spinal cord exhibit low expression. This indicates to the independent regulation of neu1 expression in various brain regions by specific signaling mechanisms as well as to the requirement of Neu function for different cell-cell signaling systems.

neu1 mRNA expression studies in adult rat brain revealed that in several brain regions, particularly in the granular cells of dentate gyrus of hippocampus, neu1 mRNA is localized in the dendrites, suggesting that synthesis of Neu1 protein also occurs in dendrites. Several data indicate that proteins locally translated from dendritic mRNAs at activated synapses provide basis for activity-dependent regulation of synaptic modulation (reviewed in Steward et al., *Neuron*, 21:741–51 (1997); Kuhl and Skehel, *Curr Opin Neurobiol*, 8(5):600–6 (1998); Schuman, *Neuron*, 23:645–8 (1999); Tiedge et al., *Science*, 283:186–7 (1999); Kiebler and DesGroseillers, *Neuron*, 25:19–28 (2000)). Accordingly, Neu could be involved in the regulation of neuritogenesis and/or synaptogenesis, affecting the generation of the precise pattern of neuronal connectivity. Recent molecular perturbation experiments suggested that Notch1 signalling in cortical neurons promotes dendritic branching and inhibits neurite growth (Redmond et al., 2000; Sestan et al., 1999). Suggesting that the function of neu1 to refine a signal upstream of Notch in *Drosophila* is evolutionary conserved in mammalian nervous system, it is possible, that Neu and Notch pathways act in an interrelated manner to confer developmental plasticity to adult neurons. The possible similarities in the molecular mechanisms of function of two genes, Notch and neu1, that were first discovered as neurogenic, are appealingly apparent.

Neu Role Related to Repair and Regeneration After Injury to the CNS

A specific temporal order of events at the cellular and molecular level occurs in response to injury to the brain. Injury-compromised neurons degenerate while surviving neurons undergo neuritogenesis and synaptogenesis to establish neuronal connectivity destroyed in the injury. In the brain, after kainate-induced change in neuronal activity (a neurotoxic, excitotoxic or ischemic insult), it was observed that a consistent down-regulation of neu1 mRNA in the hippocampal formation with a strong reduction in the molecular layer where granule cell dendrites were present. It is suggested, that after injury of the CNS, down-regulation of neu1 mRNA expression leads to reduced levels of Neu1 protein that is essential for derepression of the transcription of its target genes related to repair and regeneration, such as growth factors and synaptic proteins.

Neu Role in Memory and Learning

Another function of the Neu family of transcription factors is mediation of $Ca^{2+}$ signaling in a variety of neural processes including learning and memory. A member of Homer family of proteins, Homer2a, is referred to as an interactor of human Neu1 (GenBank Acc. No. AF081530). Homer proteins are enriched in excitatory synapses, bind group I metabotropic glutamate receptors (mGluR), and NMDA receptor interacting Shank proteins and thus can link NMDA and group I mGluR signaling pathways (reviewed in Xiao et al., Curr Opin Neurobiol, 10:370–74 (2000)). Given that Homer2a and Neu1 are co-expressed in various brain structures, it is highly conceivable that Neu1 participates in the regulation of glutamate receptor signalling in the adult brain. Glutamate receptor signaling has been implicated in several forms of activity-dependent synaptic plasticity, neurodegenerative diseases, cortical development and addiction. Consequently, if Neu is involved in glutamate receptor signaling, then the change in Neu structure, expression or function could lead to various developmental disorders and mental diseases.

Thus, it is highly conceivable that neu1 mRNA expression is regulated by physiological neuronal synaptic activity leading to reduced levels of Neu1 protein and derepression of the transcription of its target genes in the processes involving memory and learning. This function of the Neu family transcription factors makes them a good target for a variety of drugs that control different processes in the brain, during development and in disease. Manipulating this function of Neu can be used to control a variety of diseases including depression, pain, anxiety, and neurodegenerative diseases.

Neu Role in Tumorigenesis

Also, this invention relates to the role of the Neu family of factors in the development of tumors, since the human neu1 gene has been mapped to chromosome 10 within a region which is frequently deleted in gliomas. neu1 is expressed at varying levels in different neural and neuroendocrine tumors, including neuroblastomas, carcinoids, non-small cell lung cancers, and gliomas, suggesting that expression of Neu family of proteins is applicable as tumor-specific markers in clinical tumor diagnostics. Since over-expression of Neu1 blocks DNA synthesis in neuroblastoma and glioma cells, Neu family of proteins may function also as tumor suppressor genes.

Neu Role in Myogenesis and Development of Other Organ Systems.

The described herein, especially in the Examples below, show that expression of neu1 and neu2 is found to be high in at late embryonic and adult stages of development, also in developing heart and testes. neu3 was found to be widely expressed, with highest levels in immune tissues spleen and thymus and in lung. Expression of neu4 was detected only in muscle and heart. Since Neu proteins are expressed at various levels in many different body systems, the role of Neu family of proteins in several developmental pathways is apparent. Studies of $neu^{mut}$ flies have reported the overproduction of nautilus (nau) expressing cells in embryonic and muscle defects in adult stages of development. Corbin et al., Cell, 67:311–323 (1991); Hartenstein et al., Development, 116:1203–1220 (1992). nau is a myogenic bHLH factor that plays a role in the differentiation of muscle progenitors in Drosophila. Keller et al., Dev Biol, 181:197–212 (1997); Keller et al., Dev Biol, 202:157–171 (1998). Notch signaling has been shown to inhibit MyoD expression and block myogenesis in mouse. Kuroda et al., J Biol Chem, 274:7238–7244 (1999). It is possible that during mammalian myogenesis Neu refines Notch signaling by regulating expression of nau mammalian homologues (MyoD, myf5, myogenin and MRF4).

Another function of the Neu family of transcription factors is mediation of $Ca^{2+}$ signaling in muscle and other tissues. This function of the Neu family transcription factors makes them a good target for a variety of drugs that control different processes in the muscle, and in those tissues where Neu is expressed. Manipulating Neu expression and function can be used to control a variety of diseases including cancer, and muscle-degenerative diseases, dystrophinopathies, Brody's disease, and malignant hyperthermia (the last three are caused by the functional alterations of Ca(2+) signaling).

Neu Interactions with Neurogenic Genes

Additionally, activity of transcriptional regulators is modulated through interactions with other regulatory factors. Analyses of interactions between Drosophila neurogenic loci has revealed that neu appears to act upstream of notch (N), enhancer of split (E(spl)) and delta (Dl), and downstream of mastermind (mam). Boulianne et al., EMBO J. 10(10), 2975–2983 (1991). Interaction between neu and E(spl) is observed in the dominant mutation E(spl)D1, which is a mutation that enhances the phenotype of split whereas split is a mutation in the N gene. Enhancement of the split phenotype increases in the presence of additional copies of neu gene, but decreases in heterozygotes for neu mutations. Molecular interactions between these Drosophila neurogenic genes are unknown. Expression of rat SHARP1 gene (Rossner, et al., Mol Cell Neurosci, 10(3–4):460–475 (1997)), one of the vertebrate homologues of Drosophila E(spl), is almost identical to the neu1 expression pattern during development and in adult tissues. The similarity in expression patterns between neu1 and SHARP1 suggests that products of these genes could reciprocally affect the function of the other as it occurs in Drosophila between neu and E(spl) genes.

Neu Interactions with Proteins Implicated in Nuclear Transport

The nucleocytoplasmic transport of functional molecules is mediated bidirectionally through the nuclear pore complex (NPC), which spans the double membranes of the nuclear envelope. It has recently been shown that signaling between the nucleus and the cytoplasm plays a key role in coordinating the cellular processes such as the cell cycle and cell differentiation (Yoneda, Cell Struct Funct 25:205–206. 2000). The weak NLS sequences (HKAVKR (SEQ ID NO: 43), RLKITKK (SEQ ID NO: 44)), that were identified in mammalian Neu1 proteins, are indeed, implicated in the regulated nuclear import of Neu1. Importin-α family members are involved in the formation of the NLS receptor complexes that govern the protein transport to the nucleus. Ullman et al., *Cell,* 90:967–970 (1997); and Izaurralde and Adam, *RNA,* 4:351–364 (1998). We have identified importin-α3 as one of the m-Neu interacting proteins by yeast two-hybrid screening.

Neu Interactions with Miz1/GBP/PIAS Family of Proteins

Yeast two hybrid screening revealed that Neu1 interacts with NeuI-1 which is a new splice variant of Miz1/PIASX zinc finger transcription factor. Miz1 is a sequence specific DNA binding protein that functions as a positive-acting transcription factor and interacts directly with homeobox transcription factor Msx2. Wu et al., 1997 *Mech Dev,* 65(1–2):3–17 (1997). Msx1 and Msx2, members of the Msx family of homeobox genes, were found to be important in inductive tissue interactions. Whereas Msx3 was expressed exclusively in the developing nervous system. Wang, et al., *Mech Dev,* 58(1–2):203–15 (1996). Members of the PIAS family, however, regulated DNA binding of STAT transcription factors thereby interfering with the signaling of a variety of cytokines. Chuang, et al., *Biochem Biophys Res Commun,* 18;235(2):317–20 (1997) and Liu et al., *Proc Natl Acad Sci USA,* 95(18):10626–31 (1998).

Sequence analyses revealed that PIAS1 is identical to Gu/RNA helicase II (Gu/RH-II) binding protein GBP. Valdez et al., *Biochem Biophys Res Commun,* 234(2):335–40 (1997). The GBP regulates proteolytic cleavage of Gu/RH-II which could alter its functions or enzymatic activities or lead to its destruction. These data indicate that the Neu family of proteins could be involved, perhaps through its interactions with various proteins, such as the NeuI-1 protein. Such interactions may be involved in several biologically important regulatory processes including inductive tissue interactions (Miz1), cytokine signaling (PIAS), and RNA processing (GBP).

Neu Interactions with ZNF127 Zinc Finger Family of Proteins

Yeast two hybrid screening revealed that Neu1 interacts with NeuI-2. This protein is a new member of the ZNF127 zinc finger family of proteins. The ZNF127 gene is localized in Angelman/Prader-Willi region. Disruption of this gene causes a genetic defect related to mental retardation. ZNF127, as well as other genes in this region, were subjected to genomic imprinting (Mowery-Rushton et al., DNA methylation patterns in human tissues of uniparental origin using a zinc-finger gene (ZNF127) from the Angelman/Prader-Willi region *Am J Med Genet,* 61(2):140–6 (1996)). The role of ZNF127 in the development of Angelman/Prader-Willi syndrome, as well as its molecular function, is unknown. The ZNF127 family proteins, however, contain the zinc finger motif, Cx(8)Cx(5)Cx(3)-H, which is characteristic for viral and early immediate genes such as TIS11, ERF-2 (Tabara et al., 1999 pos-1 encodes a cytoplasmic zinc-finger protein essential for germline specification in *C. elegans Development,* 126(1): 1–11); and also to RNA binding proteins (Carballo et al. *Science,* 281:1001–1005 (1998)).

Neu Interactions with Parkin-Like Proteins

The NeuI-3 protein is another interactor with Neu1 and was found to be similar to the recently described human gene parkin (Kitada, et al., *Nature* 392(6676):605–8 (1998)).

Mutations in the parkin gene have been shown to result in autosomal recessive juvenile parkinsonism. The molecular function of the parkin encoded protein is unknown. Phylogenetic analysis reveals that ari and parkin are distant members of a common progeny.

Neu Interactions with Androgen Receptor Coregulator ARA54

NeuI-4, another Neu interactor, is identical to ARA54, an androgen receptor coregulator (Kang et al., J. Biol. Chem. 274, 8570–8576; 1999). Furthermore, the RING-zinc finger domain of NeuI-4 has high similarity to *Drosophila* protein ariadne (ari) that could be involved in axonal path-finding. Aguilera, et al., *Genetics* 155(3):1231–44 (1996). Two mammalian homologues of ari have been identified, however, no information is available about molecular mechanisms of the functioning of the ari family of proteins.

Neu Function Based on the Nature of Neu Interactors

Based on the nature of Neu1 interactors, it is hypothesized that Neu has the potential to interfere with inductive tissue interactions (NeuI-1/Miz), cytokine signalling (NeuI-1/PIAS), RNA processing (NeuI-1/GBP), early immediate responses (NeuI-2/ZNF127), death of specific cell populations (NeuI-3/parkin), and nuclear hormone receptor signaling and axonal path-finding (NeuI-4/ariadne).

Nucleic Acids

Having identified a number of potential functions for the Neu family of proteins, the described invention seeks to utilize this knowledge to manipulate the various developmental pathways in which Neu functions. As a preliminary step, representative members of the Neu family of proteins have been isolated and purified. Polynucleotide molecules encoding the proteins of the Neu family were then isolated and their sequences are provided below.

Representative polynucleotide molecules encoding members of the Neu family include sequences comprising SEQ ID NO: SEQ ID NO:1, 3, 5, 7, 9, 11, 13, 15, 17, 19, 21, 23, 25, 27, 29, 31, and 33. Polynucleotide molecules encoding Neu family members include those sequences resulting in minor genetic polymorphisms, differences between species, and those that contain amino acid substitutions, additions, and/or deletions.

In some instances, one can employ such changes in the sequence of a recombinant Neu to substantially decrease or even increase the biological activity of Neu relative to the wild-type Neu activity. Such changes can also be directed towards endogenous neu sequences using, for example, gene therapy methods to alter the gene product. Advantageously, the disclosed sequences can be used to identify and isolate neu polynucleotide encoding molecules from suitable vertebrate host cells. Thus, in another embodiment, a method of identifying neu polynucleotide molecules is provided.

The nucleotide sequences encoding the neuralized homology repeat domain can be used to identify polynucleotide molecules encoding other proteins of the Neu family. Complementary DNA molecules encoding Neu family members can be obtained by constructing a cDNA library from mRNA of, for example, brain or muscle tissues that are at different developmental stages. DNA molecules encoding Neu family members can be isolated from such a library using the disclosed sequences in standard hybridization techniques or by amplification of sequences using polymerase chain reaction (PCR) amplification.

In a similar manner, genomic DNA encoding Neu can be obtained using probes designed from the sequences disclosed herein. Suitable probes for use in identifying Neu family sequences can be obtained from Neu-specific sequences that are highly conserved regions between mammalian coding sequences. Primers, for example, from the neuralized homology motif domains 1 and 2 are suitable for use in designing PCR primers. Alternatively, oligonucleotides containing specific DNA sequences from a neu family coding region can be used to identify related human neu genomic and cDNA clones. One of skill in the art will appreciate that upstream regulatory regions of the neu family of genes can be obtained using similar methods.

neu family polynucleotide molecules can be isolated using standard hybridization techniques with probes of at least about 7 nucleotides in length and up to and including the full coding sequence. Other members of the neu family can be identified using degenerate oligonucleotides capable of hybridization based on the sequences disclosed herein for use PCR amplification or by hybridization at moderate or greater stringency. The term, "capable of hybridization" as used herein means that the subject nucleic acid molecules (whether DNA or RNA) anneal to an oligonucleotide of 15 or more contiguous nucleotides of SEQ ID NO:1, 3, 5, 7, 9, 11, 13, 15, 17, 19, 21, 23, 25, 27, 29, 31, or 33.

The choice of hybridization conditions will be evident to one skilled in the art and will generally be guided by the purpose of the hybridization, the type of hybridization (DNA-DNA or DNA-RNA), and the level of desired relatedness between the sequences. Methods for hybridization are well established in the literature. One of ordinary skill in the art realizes that the stability of nucleic acid duplexes will decrease with an increased number and location of mismatched bases; thus, the stringency of hybridization can be used to maximize or minimize the stability of such duplexes. Hybridization stringency can be altered by: adjusting the temperature of hybridization; adjusting the percentage of helix-destabilizing agents, such as formamide, in the hybridization mix; and adjusting the temperature and salt concentration of the wash solutions. In general, the stringency of hybridization is adjusted during the post-hybridization washes by varying the salt concentration and/or the temperature, resulting in progressively higher stringency conditions.

An example of progressively higher stringency conditions is as follows: 2×SSC/0.1% SDS at about room temperature (hybridization conditions); 0.2×SSC/0.1% SDS at about room temperature (low stringency conditions); 0.2×SSC/0.1% SDS at about 42° C. (moderate stringency conditions); and 0.1×SSC at about 68° C. (high stringency conditions). Washing can be carried out using only one of these conditions, e.g., high stringency conditions, or each of the conditions can be used, e.g., for 10–15 minutes each, in the order listed above, repeating any or all of the steps listed. However, as mentioned above, optimal conditions will vary, depending on the particular hybridization reaction involved, and can be determined empirically. In general, conditions of high stringency are used for the hybridization of the probe of interest.

Alternatively, polynucleotides having substantially the same nucleotide sequence set forth in SEQ ID NO:1, 3, 5, 7, 9, 11, 13, 15, 17, 19, 21, 23, 25, 27, 29, 31, and 33 or functional fragments thereof, or nucleotide sequences that are substantially identical to SEQ ID NO:1, 3, 5, 7, 9, 11, 13, 15, 17, 19,21, 23, 25, 27, 29, 31, and 33, can represent members of the Neu family of proteins. By "substantially the same" or "substantially identical" is meant a nucleic acid or polypeptide exhibiting at least 80%, 85%, 90%, 95% or 100% homology to a reference nucleic acid. For nucleotide sequences, the length of comparison sequences will generally be at least 10 to 500 nucleotides in length. More specifically, the length of comparison will be at least 50 nucleotides, at least 60 nucleotides, at least 75 nucleotides, and at least 110 nucleotides in length.

One embodiment of the invention provides isolated and purified polynucleotide molecules encoding Neu proteins, wherein the polynucleotide molecules that are capable of hybridizing under moderate to stringent conditions to an oligonucleotide of 15 or more contiguous nucleotides of SEQ ID NO: 1, 3, 5, 7, 9, 11, 13, 15, 17, 19, 21, 23, 25, 27, 29, 31, or 33, including complementary strands thereto.

DNA sequences of the invention can be obtained by several methods. For example, the DNA can be isolated using hybridization or computer-based techniques which are well known in the art. Such techniques include, but are not limited to: 1) hybridization of genomic or cDNA libraries with probes to detect homologous nucleotide sequences; 2) antibody screening of expression libraries to detect cloned DNA fragments with shared structural features; 3) polymerase chain reaction (PCR) on genomic DNA or cDNA using primers capable of annealing to the DNA sequence of interest; 4) computer searches of sequence databases for similar sequences; and 5) differential screening of a subtracted DNA library.

Screening procedures which rely on nucleic acid hybridization make it possible to isolate any gene sequence from any organism, provided the appropriate probe is available. Oligonucleotide probes, which correspond to a part of the neu family of sequences provided herein and encoding a Neu protein family member, can be synthesized chemically. This requires that short, oligo-peptide stretches of the amino acid sequence be known. The DNA sequence encoding the protein can be deduced from the genetic code, however, the degeneracy of the code must be taken into account. It is possible to perform a mixed addition reaction when the sequence is degenerate. This includes a heterogeneous mixture of denatured double-stranded DNA. For such screening, hybridization is preferably performed on either single-stranded DNA or denatured double-stranded DNA. Hybridization is particularly useful in the detection of cDNA clones derived from sources where an extremely low amount of mRNA sequences relating to the polypeptide of interest are present. In other words, by using stringent hybridization conditions directed to avoid non-specific binding, it is possible, for example, to allow the autoradiographic visualization of a specific cDNA clone by the hybridization of the target DNA to that single probe in the mixture which is its complete complement. (Wallace, et al., *Nucl. Acid Res.*, 9:879, 1981). Alternatively, a subtractive library is useful for elimination of non-specific cDNA clones.

Among the standard procedures for isolating cDNA sequences of interest is the formation of plasmid- or phage-carrying cDNA libraries which are derived from reverse transcription of mRNA which is abundant in donor cells that have a high level of gene expression. When used in combination with polymerase chain reaction technology, even rare expression products can be cloned. In those cases where significant portions of the amino acid sequence of the polypeptide are known, the production of labeled single or double-stranded DNA or RNA probe sequences duplicating a sequence putatively present in the target cDNA can be employed in DNA/DNA hybridization procedures which are carried out on cloned copies of the cDNA which have been denatured into a single-stranded form (Jay, et al., *Nucl. Acid Res.*, 11:2325, 1983).

The nucleotide sequences of the present invention have a myriad of applications. Representative uses of the nucleotide sequences of the invention include the construction of cDNA and oligonucleotide probes useful in Northern, Southern, and dot-blot assays for identifying and quantifying the level of expression of Neu family proteins in a cell. Lack of expression of a Neu protein in tumors, diseased cells or tissues can indicate that measuring the level of Neu expression can provide prognostic markers for assessing the growth rate and invasiveness of a tumor.

In addition, considering the important role of Neu in development and $Ca^{2+}$ signaling, it is thought highly likely that birth defects, degenerative, and psychiatric diseases can result from expression of an abnormal Neu protein. In this case, the Neu protein family can prove highly useful in prenatal screening of mothers and/or for in utero testing of fetuses. Also, early diagnosis of degenerative and neurological diseases can be based on the analyses of changes in Neu expression and mutations in the neu genes.

Similarly, the nucleotide sequences can be employed for the construction of recombinant cell lines, ova, and transgenic embryos and animals including dominant-negative and "knock-out" recombinant cell lines in which the regulatory activity of Neu protein is down-regulated or eliminated. Such cells can contain altered Neu coding sequences that result in the expression of a Neu protein that is not capable of enhancing, suppressing or activating transcription of the target gene. The subject cell lines and animals find use in screening for candidate therapeutic agents capable of either substituting for a function performed by Neu or correcting the cellular defect caused by a defective Neu.

The Neu family of proteins presents an attractive set of diagnostic and therapeutic targets, considering the important regulatory role this family of proteins plays in the development function of adult organisms. This important role is reflected by the effects one or defects in a mutant Neu protein can inflict upon an organism. Moreover, with the advances in art of gene therapy progresses, these defects can be correctable in utero or in early post-natal life or alternatively through the use of compounds identified in screening assays using Neu proteins. In addition, neu polynucleotide molecules can be joined to reporter genes, such as beta-galactosidase, luciferase, or green fluorescent proteins (GFP) and inserted into the genome of a suitable host cell such as an embryonic or tissue specific stem cell by, for example, homologous recombination. Cells expressing neu can then be obtained by subjecting the differentiating cells to cell sorting, leading to the purification of a population of neu expressing cells. These cells can be useful for studying specific activity of isolated cell populations. Also, these cells can be used to study sensitivity to growth factors or chemotherapeutic agents.

In yet another application of the nucleotide sequence discovery, the technology can be useful in the construction of gene transfer vectors (e.g., retroviral vectors, and the like). In these vectors, the neu sequence is often inserted into the coding region of the vector under the control of a promoter. neu gene therapy can be used to correct neurological and movement diseases and cancer. For these therapies, gene transfer vectors can either be injected directly at the site of diseased cells, or the vectors can be used to construct transformed host cells that are then injected at the site of disease.

In one embodiment, a vector comprising a DNA molecule coding a Neu protein is provided. Preferably, a DNA molecule coding a Neu protein is inserted into a suitable expression vector, which is in turn used to transfect or transform a suitable host cell. Exemplary expression vectors for use in carrying out the present invention include a promoter capable of directing the transcription of a polynucleotide molecule of interest in a host cell. Representative expression vectors include both plasmid and/or viral vector sequences. Suitable vectors include retroviral vectors, vaccinia viral vectors, CMV viral vectors, BLUESCRIPT (Stratagene, San Diego, Calif.) vectors, baculovirus vectors, and the like. In another embodiment, promoters capable of directing the transcription of a cloned gene or cDNA can be inducible or constitutive promoters and include viral and cellular promoters. In particularly preferred embodiments, viral vectors are employed for use in expressing Neu proteins in mammalian cells particularly if neu is used for gene therapy.

In some embodiments, it can be preferable to use a selectable marker to identify cells that contain the cloned DNA. Selectable markers are generally introduced into the cells along with the cloned DNA molecules and include genes that confer resistance to drugs, such as neomycin, hygromycin, and methotrexate. Selectable markers can also complement auxotrophies in the host cell. Other selectable markers provide detectable signals, such as beta-galactosidase to identify cells containing the cloned DNA molecules. Advantageously, the selectable markers are amplifiable. Such amplifiable selectable markers can be used to amplify the number of sequences integrated into the host genome.

Antisense

Antisense neu nucleotide sequences can be used to block expression of mutant neu expression in a variety of cell types. Suitable antisense oligonucleotides are at least 11 nucleotides in length and can include untranslated (upstream or intron) and associated coding sequences. As will be evident to one skilled in the art, the optimal length of an anti sense oligonucleotide depends on the strength of the interaction between the antisense oligonucleotide and the complementary mRNA, the temperature and ionic environment in which translation takes place, the base sequence of the antisense oligonucleotide, and the presence of secondary and tertiary structure in the mRNA and/or in the antisense oligonucleotide. Suitable target sequences for antisense oligonucleotides include intron-exon junctions (to prevent proper splicing), regions in which DNA/RNA hybrids will prevent transport of mRNA from the nucleus to the cytoplasm, initiation factor binding sites, ribosome binding sites, and sites that interfere with ribosome progression.

Antisense oligonucleotides can be prepared, for example, by the insertion of a DNA molecule containing the target DNA sequence into a suitable expression vector such that the DNA molecule is inserted downstream of a promoter in a reverse orientation as compared to the gene itself. The expression vector can then be transduced, transformed or transfected into a suitable cell resulting in the expression of antisense oligonucleotides. Alternatively, antisense oligonucleotides can be synthesized using standard manual or automated synthesis techniques. Synthesized oligonucleotides are introduced into suitable cells by a variety of means including electroporation, calcium phosphate precipitation, or microinjection. The selection of a suitable antisense oligonucleotide administration method will be evident to one skilled in the art. With respect to synthesized oligonucleotides, the stability of antisense oligonucleotide-mRNA hybrids are advantageously increased by the addition of stabilizing agents to the oligonucleotide. Stabilizing agents include intercalating agents that are covalently attached to either or both ends of the oligonucleotide. In preferred embodiments, the oligonucleotides are made resistant to nucleases by, for example, modifications to the phosphodiester backbone by the introduction of phosphotriesters, phosphonates, phosphorothioates, phosphoroselenoates, phosphoramidates, phosphorodithioates, or morpholino rings.

Protein Production

As would be evident to one skilled in the art, the polynucleotide molecules of the present invention can be expressed in a variety of prokaryotic and eucaryotic organisms. For example, the Neu family of proteins can be expressed in to, *Saccharomyces cerevisiae,* filamentous fungi, and bacteria, such as *E. coli* to produce Neu proteins. Similarly, one can express the protein of the described invention in other host cells such as avian, insect, and plant cells using regulatory sequences, vectors, and methods well established in the literature.

Neu proteins produced according to the present invention can be purified using a number of established methods such as affinity chromatography using anti-Neu antibodies coupled to a solid support. Fusion proteins of antigenic tag and Neu can be purified using antibodies to the tag. Optionally, additional purification is achieved using conventional purification means such as liquid chromatography, gradient centrifugation, and gel electrophoresis, among others. Methods of protein purification are known in the art and can be applied to the purification of recombinant Neu described herein.

Amino Acids

In one embodiment, the identification of mammalian Neu genes is provided. Preferably, the mammalian Neu genes have highly conserved sequences across the neuralized homology motif domains at the amino acid level (Neu1, Neu 2, Neu3, and Neu 4). The following Neu polypeptides or proteins have been identified: human neural Neu1 protein of SEQ. ID. NO.: 2, human muscle Neu1 protein SEQ. ID. NO.: 4; human Neu1 alternatively spliced form (h-neu1ΔNHR1) of SEQ. ID. NO.: 6; mouse neural Neu1 protein of SEQ. ID. NO.: 8; mouse muscle Neu1 protein SEQ. ID. NO.: 10; mouse Neu1 alternatively spliced form (m-neu1ΔNHR2A) of SEQ. ID. NO.: 12; mouse Neu1 alternatively spliced form (m-neu1ΔNHR2B) of SEQ. ID. NO.: 14; rat Neu 1 protein SEQ. ID. NO.: 16; rat Neu1 alternatively spliced form (r-neu1ΔNHR2A) of SEQ. ID. NO.: 18; rat Neu1 alternatively spliced form (r-neu1ΔNHR2B) of SEQ. ID. NO.: 20; human Neu2 protein of SEQ. ID. NO.: 22; human Neu2 alternatively spliced form (h-neu2ΔNHR1) of SEQ. ID. NO.: 24; human Neu2 alternatively spliced form (h-neu2ΔNHR2) of SEQ. ID. NO.: 26; rat Neu 2 protein SEQ. ID. NO.: 28; human Neu3 protein of SEQ. ID. NO.: 30; mouse Neu3 protein of SEQ. ID. NO.: 32; and human Neu4 protein (partial) of SEQ. ID. NO.: 34.

The described invention encompasses Neu variants that, for example, are modified in a manner that results in Neu proteins capable of translocating into the nucleus but unable to repress transcription. Fragments of Neu proteins that are capable of transcriptional repression but are incapable of translocating into the nucleus are also encompassed by the present description. Proteins retrieved from naturally occurring materials and closely related, functionally similar proteins retrieved by antisera specific to Neu, and recombinantly expressed proteins encoded by genetic materials (DNA, RNA, cDNA) retrieved on the basis of their similarity to the unique regions in the neu family of genes, are also encompassed by the present description.

According to the present description, polynucleotide molecules encoding Neu encompass those molecules that encode Neu proteins or peptides that share identity with the sequences shown in SEQ ID NO: 2, 4, 6, 8, 10, 12, 14, 16, 18, 20, 22, 24, 26, 28, 30, 32, and 34. Such molecules preferably share greater than 30% identity at the amino acid level with the disclosed sequences in Neu. In preferred embodiments, the polynucleotide molecules can share greater identity at the amino acid level across highly conserved regions such as the neuralized homology repeat domains and the RING-zinc finger domains.

It is contemplated that amino acid sequences substantially the same as the sequences set forth in SEQ ID NO: 2, 4, 6, 8, 10, 12, 14, 16, 18, 20, 22, 24, 26, 28, 30, 32, and 34, are encompassed by the described invention. A preferred embodiment includes polypeptides having substantially the same sequence of amino acids as the amino acid sequence set forth in SEQ ID NO: 2, 4, 6, 8, 10,12, 14, 16, 18, 20, 22, 24, 26, 28, 30, 32, and 34, or functional fragments thereof, or amino acid sequences that are substantially identical to SEQ ID NO: 2, 4, 6, 8, 10, 12, 14, 16, 18, 20, 22, 24, 26, 28, 30, 32, and 34. By "substantially the same" or "substantially identical" is meant a polypeptide exhibiting at least 80%, preferably 85%, more preferably 90%, and most preferably 95% homology to a reference amino acid sequence. For polypeptides, the length of comparison sequences will generally be at least 16 amino acids, preferably at least 20 amino acids, more preferably at least 25 amino acids, and most preferably 35 amino acids.

Homology is often measured using sequence analysis software (e.g., Sequence Analysis Software Package of the Genetics Computer Group, University of Wisconsin Biotechnology Center, 1710 University Avenue, Madison, Wis. 53705). Such software matches similar sequences by assigning degrees of homology to various substitutions, deletions, substitutions, and other modifications.

The term "functional fragments" includes those fragments of SEQ ID NO: 2, 4, 6, 8. 10, 12, 14, 16, 18, 20, 22, 24, 26, 28, 30, 32, and 34, or other Neu family members, that retain the function or activity of a Neu transcriptional regulator. One of skill in the art can screen for the functionality of a fragment by using the examples provided herein, where full-length Neu transcriptional factors are described. It is also envisioned that fragments of various Neu proteins that inhibit or promote transcription can be identified in a similar manner. Neu transcriptional activity can also be assayed by standard transcription assays.

By "substantially identical" is also meant an amino acid sequence which differs only by conservative amino acid substitutions, for example, substitution of one amino acid for another of the same class (e.g., valine for glycine, arginine for lysine, etc.) or by one or more non-conservative substitutions, deletions, or insertions located at positions of the amino acid sequence which do not destroy the function of the protein assayed, (e.g., as described herein). Preferably, such a sequence is at least 85%, more preferably identical at the amino acid level to SEQ ID NO:2, 4, 6, 8, 10, 12, 14, 16, 18, 20, 22, 24, 26, 28, 30, 32, and 34.

By a "substantially pure polypeptide" is meant a Neu protein that has been separated from components which naturally accompany it. Typically, the polypeptide is substantially pure when it is at least 60%, by weight, free from the proteins and naturally occurring organic molecules with which it is typically associated. Preferably, the preparation is at least 75%, more preferably at least 90%, and most preferably at least 99%, by weight, Neu protein. A substantially pure Neu polypeptide can be obtained, for example, by extraction from a natural source; by expression of a recombinant nucleic acid encoding a Neu polypeptide; or by chemically synthesizing the protein. Purity can be measured by any appropriate method, e.g., column chromatography, polyacrylamide gel electrophoresis, or by HPLC analysis.

A protein is substantially free of naturally associated components when it is separated from those contaminants that accompany it in its natural state. Thus, a protein that is chemically synthesized or produced in a cellular system different from the cell from which it naturally originates will be substantially free from its naturally associated components. Accordingly, substantially pure polypeptides include those derived from eukaryotic organisms but synthesized in *E. coli* or other prokaryotes.

As would be evident to one skilled in the art, the polynucleotide molecules of the present disclosure can be expressed in a variety of prokaryotic and eucaryotic cells using regulatory sequences, vectors, and methods well established in the literature.

Neu proteins produced according to the present invention can be purified using a number of established methods such as affinity chromatography using anti-Neu antibodies coupled to a solid support. Fusion proteins of antigenic tag and Neu can be purified using antibodies to the tag. Optionally, additional purification is achieved using conventional purification means such as liquid chromatography, gradient centrifugation, and gel electrophoresis, among others. Methods of protein purification are known in the art and can be applied to the purification of recombinant Neu described herein.

Construction of interspecies hybrid Neu proteins and hybrid Neu proteins containing one or more domains from another Neu family member are also contemplated. Such hybrid proteins facilitate structure-function analyses. Similarly, hybrid proteins allow for the alteration of Neu activity by increasing or decreasing the transcriptional regulation of target genes. Hybrid proteins of the present invention contain the replacement of one or more contiguous amino acids of the native Neu with the analogous amino acid(s) of Neu from another species or other protein of the Neu family. Such interspecies or interfamily hybrid proteins include hybrids having whole or partial domain replacements. Such hybrid proteins are obtained using recombinant DNA techniques well known by one of skill in the art. Briefly, DNA molecules encoding the hybrid Neu proteins of interest are prepared using generally available methods such as PCR mutagenesis, site-directed mutagenesis, and/or restriction digestion and ligation. The hybrid DNA is then inserted into expression vectors and introduced into suitable host cells.

One embodiment of the present invention involves the isolation of proteins that interact with Neu proteins and regulate Neu protein function or are regulated by Neu. Neu proteins can be used in immunoprecipitation to isolate interacting factors or used for the screening of interactors using different methods of two hybrid screening. Isolated interactors of Neu can be used to modify Neu activity or Neu can be used to modify the activity of interactors. Two hybrid screening has resulted in the isolation of several types of interactors. Sequence analyses showed that all interactors are novel proteins and contain RING-zinc finger domain located in the C-terminus of the protein. Neu-1 (4 clones) is a novel splice variant (SEQ ID NO: 35, 36) of zinc finger protein Miz1/PIASXα/ARIP3 (GenBank accession numbers NM_008602; AF077953; AF077954; AF044058). Neu-2 (3 clones) is a fourth homolog (SEQ ID NO: 37, 38; GenBank accession numbers AF277171; AF302084) of zinc finger protein ZNF127 (GenBank accession numbers U19106; U19107). Neu-3 (9 clones) has highest homology to a human hypothetical protein (GenBank accession number AK001459) and to a *Drosophila* hypothetical protein (AAF56052.2) produced from CG4813 gene of a genomic scaffold (GenBank accession number AE003740) (SEQ ID NO: 39, 40). Neu-4 (12 clones) is the homolog of the androgen receptor coactivator ARA54 (SEQ. ID. NO.: 32; GenBank accession number AF060544) (SEQ. ID. NO.: 41, 42).

In still another embodiment, synthetic peptides, recombinantly derived peptides, fusion proteins, chiral proteins (stereochemical isomers, racemates, enantiomers, and D-isomers) and the like are provided which include a portion of Neu or the entire protein. The subject peptides have an amino acid sequence encoded by a nucleic acid which hybridizes under stringent conditions with an oligonucleotide of 15 or more contiguous nucleotides of SEQ ID NO: 1, 3, 5, 7, 9, 11, 13, 15, 17, 19, 21, 23, 25, 27, 29, 31 or 33 Representative amino acid sequences of the subject peptides are disclosed in SEQ ID NO: 2, 4, 6, 8, 10, 12, 14, 16, 18, 20, 22, 24, 26, 28, 30, 32, and 34. The subject peptides find a variety of uses, including preparation of specific antibodies and preparation of antagonists of Neu activity.

Antibodies

As noted above, the described teachings provide antibodies that bind to Neu. The production of non-human antisera or monoclonal antibodies (e.g., murine, lagomorph, porcine, equine) is well known and can be accomplished by, for example, immunizing an animal with Neu protein or peptides. Additionally, catalytic antibodies to nuclear isoforms of the Neu family of proteins or Neu protein metabolic intermediates that are transported into and out of the nucleus can be generated. For the production of monoclonal antibodies, antibody producing cells are obtained from immunized animals, immortalized and screened, or screened first for the production of the antibody that binds to the Neu protein or peptides and then immortalized. It can be desirable to transfer the antigen binding regions (e.g., $F(ab')_2$ or hypervariable regions) of non-human antibodies into the framework of a human antibody by recombinant DNA techniques to produce a substantially human molecule.

Following synthesis or expression and isolation or purification of a Neu protein or a portion thereof, the isolated or purified protein can be used to generate antibodies and tools for identifying agents that interact with the Neu protein and fragments of the Neu protein. Depending on the context, the term "antibodies" can encompass polyclonal, monoclonal, chimeric, single chain, Fab fragments and fragments produced by a Fab expression library. Antibodies that recognize Neu proteins and fragments of Neu proteins have many uses including, but not limited to, biotechnological applications, therapeutic/prophylactic applications, and diagnostic applications.

For the production of antibodies, various hosts including goats, rabbits, rats, mice, etc. can be immunized by injection with Neu proteins or any portion, fragment or oligopeptide that retains immunogenic properties. Depending on the host species, various adjuvants can be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. BCG (*Bacillus* Calmette-Guerin) and *Corynebacterium parvum* are also potentially useful adjuvants.

Peptides used to induce specific antibodies can have an amino acid sequence consisting of at least three amino acids, and preferably at least 10 to 15 amino acids. Preferably, short stretches of amino acids encoding fragments of Neu proteins are fused with those of another protein such as keyhole limpet hemocyanin such that an antibody is produced against the chimeric molecule. While antibodies capable of specifically recognizing Neu proteins can be generated by injecting synthetic 3-mer, 10-mer, and 15-mer peptides that correspond to a protein sequence of Neu proteins into mice, a more diverse set of antibodies can be generated by using recombinant Neu proteins, purified Neu proteins, or fragments of Neu proteins.

To generate antibodies to Neu proteins and fragments of Neu proteins, a substantially pure Neu protein or a fragment of Neu protein is isolated from a transfected or transformed cell. The concentration of the polypeptide in the final preparation is adjusted, for example, by concentration on an Amicon filter device, to the level of a few micrograms/ml. Monoclonal or polyclonal antibody to the polypeptide of interest can then be prepared as follows:

Monoclonal antibodies to Neu proteins or a fragment of Neu proteins can be prepared using any technique that provides for the production of antibody molecules by continuous cell lines in culture. These include, but are not limited to, the hybridoma technique originally described by Koehler and Milstein (*Nature* 256:495–497 (1975), the human B-cell hybridoma technique (Kosbor et al. *Immunol Today* 4:72 (1983); Cote et al *Proc Natl Acad Sci* 80:2026–2030 (1983), and the EBV-hybridoma technique Cole et al. *Monoclonal Antibodies and Cancer Therapy,* Alan R. Liss Inc, New York N.Y., pp 77–96 (1985). In addition, techniques developed for the production of "chimeric antibodies", the splicing of mouse antibody genes to human antibody genes to obtain a molecule with appropriate antigen specificity and biological activity can be used. (Morrison et al. *Proc Natl Acad Sci* 81:6851–6855 (1984); Neuberger et al. *Nature* 312:604–608(1984); Takeda et al. *Nature* 314:452–454(1985). Alternatively, techniques described for the production of single chain antibodies (U.S. Pat. No. 4,946,778) can be adapted to produce Neu protein-specific single chain antibodies. Antibodies can also be produced by inducing in vivo production in the lymphocyte population or by screening recombinant immunoglobulin libraries or panels of highly specific binding reagents as disclosed in Orlandi et al., *Proc Natl Acad Sci* 86: 3833–3837 (1989), and Winter G. and Milstein C; *Nature* 349:293–299 (1991).

Antibody fragments that contain specific binding sites for Neu proteins can also be generated. For example, such fragments include, but are not limited to, the F(ab')$_2$ fragments that can be produced by pepsin digestion of the antibody molecule and the Fab fragments that can be generated by reducing the disulfide bridges of the F(ab')$_2$ fragments. Alternatively, Fab expression libraries can be constructed to allow rapid and easy identification of monoclonal Fab fragments with the desired specificity. (Huse W. D. et al. *Science* 256:1275–1281 (1989)).

By one approach, monoclonal antibodies to Neu proteins or fragments thereof are made as follows. Briefly, a mouse is repetitively inoculated with a few micrograms of the selected protein or peptides derived therefrom over a period of a few weeks. The mouse is then sacrificed, and the antibody producing cells of the spleen isolated. The spleen cells are fused in the presence of polyethylene glycol with mouse myeloma cells, and the excess unfused cells destroyed by growth of the system on selective media comprising aminopterin (HAT media). The successfully fused cells are diluted and aliquots of the dilution placed in wells of a microtiter plate where growth of the culture is continued. Antibody-producing clones are identified by detection of antibody in the supernatant fluid of the wells by immunoassay procedures, such as ELISA, as originally described by Engvall, E., *Meth. Enzymol.* 70:419 (1980), and derivative methods thereof. Selected positive clones can be expanded and their monoclonal antibody product harvested for use. Detailed procedures for monoclonal antibody production are described in Davis, L. et al. *Basic Methods in Molecular Biology* Elsevier, N.Y. Section 21-2.

Polyclonal antiserum containing antibodies to heterogenous epitopes of a single protein can be prepared by immunizing suitable animals with the expressed protein or peptides derived therefrom described above, which can be unmodified or modified to enhance immunogenicity. Effective polyclonal antibody production is affected by many factors related both to the antigen and the host species. For example, small molecules tend to be less immunogenic than others and can require the use of carriers and adjuvant. Also, host animals vary in response to site of inoculations and dose, with both inadequate or excessive doses of antigen resulting in low titer antisera. Small doses (ng level) of antigen administered at multiple intradermal sites appears to be most reliable. An effective immunization protocol for rabbits can be found in Vaitukaitis, J. et al. *J. Clin. Endocrinol. Metab.* 33:988–991 (1971).

Booster injections can be given at regular intervals, and antiserum harvested when antibody titer thereof, as determined semi-quantitatively, for example, by double immunodiffusion in agar against known concentrations of the antigen, begins to fall. See, for example, Ouchterlony, O. et al., Chap. 19 in: *Handbook of Experimental Immunology* D. Wier (ed) Blackwell (1973). Plateau concentration of antibody is usually in the range of 0.1 to 0.2 mg/ml of serum (about 12 $\mu$M). Affinity of the antisera for the antigen is determined by preparing competitive binding curves, as described, for example, by Fisher, D., Chap. 42 in: *Manual of Clinical Immunology,* 2d Ed. (Rose and Friedman, Eds.) Amer. Soc. For Microbiol., Washington, D.C. (1980). Antibody preparations prepared according to either protocol are useful in quantitative immunoassays that determine concentrations of antigen-bearing substances in biological samples; they are also used semi-quantitatively or qualitatively (e.g., in diagnostic embodiments that identify the presence of a Neu protein in biological samples). It is also contemplated that various methods of molecular modeling and rational drug design can be applied to identify additional Neu protein family members, compounds that resemble a Neu protein or fragment or derivative thereof, and molecules that interact with Neu proteins and, thereby modulate their function.

Additional Applications

The Neu family of proteins presents an attractive set of diagnostic and therapeutic targets, considering the important regulatory role this family of proteins plays in the development function of adult organisms. This important role is reflected by the effects one or more defects in a mutant Neu protein can inflict upon an organism. Moreover, with the advances in the art of gene therapy, these defects can be corrected in utero or in early post-natal life or alternatively through the use of compounds identified in screening assays using Neu proteins.

In some instances, cancer cells, or diseased cells or tissue, can contain a non-functional Neu protein or can contain no Neu protein due to a genetic mutation or somatic mutations such that these cells fail to stop proliferating and differentiate. For cancers of this type, the cancer cells can be treated in a manner to cause the over-expression of wild-type Neu protein to force differentiation and cease proliferation of the cancer cells. Accordingly, a method of treating cancer is similarly provided.

It is also contemplated that because neu family genes control cell proliferation and $Ca^{2+}$ signaling induced transcriptional processes, that manipulating Neu expression and function may be useful in controlling a variety of diseases, a few examples of which include depression, pain, anxiety, neurodegenerative diseases, and cancer.

The practice of the described invention is illustrated in the following non-limiting examples. The examples are provided below are not intended to limit the invention in any way.

EXAMPLE 1

Characterization of neu1 Transcripts

A mouse cDNA library of postnatal day (P) 1 brain (Stratagene, San Diego, Calif.) was screened with a mouse 0.7 kb EST (GenBank #AA518339) cDNA clone corresponding to a region ranging from about the translation initiation codon to the end of the first neuralized homology repeat domain (NHR1) of h-neu1 (Nakamura et al., 1998).

Sequence analyses, the results of which are shown in FIG. 1, revealed that the isolated cDNA clones differed in their 5' regions encoding muscle- and brain-specific m-Neu1 proteins with different N-termini (FIG. 1). In the figure, "A" shows an amino acid sequence comparison of Drosophila, human, rat and mouse neu1 proteins. Various domain regions of the proteins are illustrated. The regions Brain-N, relating to the neural-specific N-terminal region, and Muscle-N, the muscle-specific N-terminal of mammalian neu proteins, are boxed. The NHR1 and NHR2 regions, neuralized homology repeat domains 1 and 2; RZD, RING zinc finger domain are underlined. NLS1 and NLS2, nuclear localization signal sequences, are also shown.

RT-PCR analyses of RNA from mouse and rat brain and skeletal muscle resulted in identification of 6 different Neu1 transcripts in both species (FIG. 1): 1) brain- and muscle-specific transcripts encoding Neu1 with the intact NHR2 domain (574 and 557 amino acids, respectively); 2) brain- and muscle-specific transcripts encoding Neu1 protein isoforms that lack the region between NHR1 and NHR2, the entire NHR2 region and different parts of the linker region preceding the RZD (Neu1-ΔNHR2A, 342 and 325 amino acids and Neu1-ΔNHR2B, 291 and 274 amino acids).

Turning again to FIG. 1, the region between asterisks is absent in the splice isoform neu1-ΔNHR2A; the region between the open circles is absent in the splice isoform neu1-ΔNHR2B; the pKB consensus sequence between NHR1 and NHR2; LRS, two putative leucine rich sequences in the end of both the NHR; and SP, the serine and proline rich repeats between the NHR2 and RZD are boxed. "B" is a schematic representation of the domain structure of different mouse and rat Neu1 isoforms. Structures of the full length Neu1 protein (neu, 574 amino acids) and of two Neu1 isoforms (neu-ΔNHR2A, 342 amino acids, neu-ΔNHR2B, 291 amino acids) are shown. Lines indicate to the alternative splicing resulting in the cDNAs encoding neu-ΔNHR2A and neu-ΔNHR2B isoforms. The numbers below the neu-ΔNHR2A and neu-ΔNHR2B correspond to the amino acids of the full length Neu1 protein.

Sequence analyses revealed that alternative splicing in the NHR2 and RZD linker region occurs in-frame and does not affect the intactness of the RING zinc finger structure. Accordingly, both m-neu1 and r-neu1 genes encode protein isoforms with one or two NHRs followed by the C3HC4-type RZD in the C-terminus. To date no proteins other than Neu1 proteins have been identified that contain NHR-like domains and the function of the NHR-like domains has not been previously identified. The RING zinc finger motifs are present in many regulatory proteins and have been shown to mediate protein-protein interactions. Saurin et al., Trends Biochem Sci, 21:208–214 (1996).

Like h-Neu, m-Neu1 and r-Neu do not have sequences that are similar to the Lys-rich nuclear localization signal (NLS) in d-Neu. However, two smaller clusters of Arg and Lys rich amino acids (HKAVKAR (SEQ ID NO: 43) at 80–85 and RLKITKK (SEQ ID NO: 44) at 107–113) are present in the NHR1 of mouse, rat, and human Neu1 that resemble the phosphorylation consensus sequence of NLS, m-Neu1, r-Neu, and h-Neu proteins, which are rich in Ser and Thr residues. The presence of these regions suggests that Neu1 is regulated by phosphorylation. The region between NHR1 and NHR2 contains also a putative protein kinase B/AKT phosphorylation site RPRSFT (SEQ ID NO: 45) which is similar to the respective consensus sequence RXRXXS/T (SEQ ID NO: 46). Datta, et al., Genes and Dev, 13:2905–27 (1999).

The region between NHR2 and RZD of m-Neu1, r-Neu, and h-Neu contains two imperfect repeats of Pro, Ser, and Thr residues with the consensus sequence S/TXPXSPXSXPXSPXXXGXXX(X)SD (SEQ ID NO: 47) where X denotes any amino acid. It is interesting to note that this SP repeat of mammalian Neu1 proteins is not similar to any known protein motifs.

EXAMPLE 2

Figure 2:
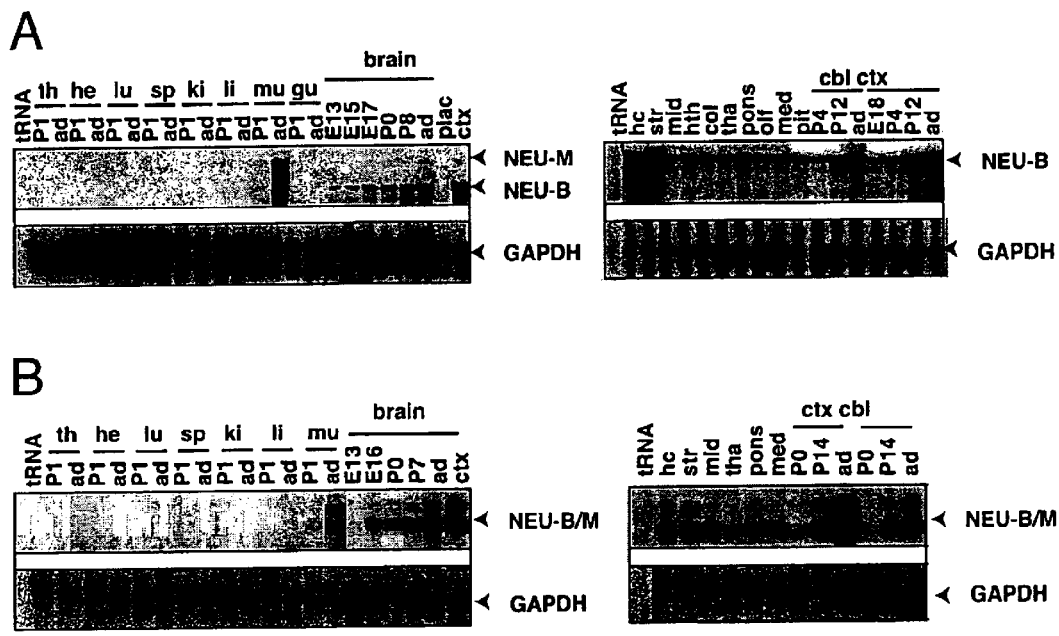
FIG. 2 is an analysis of neu1 mRNA expression by RNase protection assay in mouse (A) and rat (B).

Developmentally Regulated Expression of neu1 mRNA in the Mouse and Rat Skeletal Muscle and Brain An RNase protection analyses (RPA) was used to determine the levels of m-neu1 and r-neu1 mRNAs in the developing and adult brain and non-neural tissues (FIG. 2).

Total RNA was isolated from the mouse and rat brain regions, which are indicated (A) and (B) respectively in FIG. 2, and non-neural tissues. Levels of neu1 transcripts were analyzed by RNase protection assays. The cRNA probes used for detection of m-neu1 transcripts were complementary to a region encoding the muscle-specific (FIG. 2, left panel) or the brain-specific (FIG. 2, right panel) N-terminus and first half NHR1 of m-neu1. For r-neu1, the cRNA probe was complementary to a region encoding the second half of NHR2 up to the stop codon. Specific protected fragments are indicated on the right of each panel.

Bottom panels of FIG. 2 show the levels of GAPDH mRNA in the RNA samples. The nomenclature used to identify each sample is as follows: neu-M, indicates a muscle-specific m-neu1 transcript; neuB, indicates a brain-specific m-neu1 transcript; neu-B/M indicates the total pool of muscle- and brain-specific r-neu1 transcripts. Further, E, denotes "Embryonic day"; P, denotes "postnatal day"; ad, denotes "adult"; th, denotes "thymus"; he, denotes "heart"; lu, denotes "lung"; sp, denotes "spleen"; ki, denotes "kidney"; li, denotes "liver"; mu, denotes "skeletal muscle"; gu, denotes "gut"; plac, denotes "placenta"; ctx, denotes "cerebral cortex"; cbl, denotes "cerebellum"; hc, denotes "hippocampus"; str, denotes "striatum"; mid, denotes "ventral midbrain"; hth, denotes "hypothalamus"; col, denotes "colliculi"; thal, denotes "thalamus"; pons, denotes "pons"; of, denotes "olfactory bulb"; med, denotes "medulla"; pit, denotes "pituitary"; and tRNA, denotes "yeast tRNA", which was used as a negative control.

The overall highest expression levels of neu1 mRNA were seen in the adult skeletal muscle and brain. In the skeletal muscle, neu1 mRNA levels were undetectable during embryonic development, low at birth and upregulated during postnatal development reaching the highest levels in the adult. Other non-neural tissues (heart, kidney, liver, lung, thymus, and spleen) except for the adult heart and testis did not express neu1 transcripts or the levels were below the detection limit of the RPA. In the brain, low levels of neu1 mRNA were detected at embryonic day (E) 13 and the expression increased progressively reaching the highest levels in the adult. neu1 expression levels were high in the cerebral cortex, hippocampus, and striatum and substantially lower in the olfactory system, thalamus/hypothalamus, midbrain, cerebellum, pons, and medulla.

neu1 expression levels were specifically analyzed during postnatal development of cerebral cortex and cerebellum. In both of these brain regions, low levels of neu1 mRNA were observed in postnatal day (P) 1 whereas by two weeks after birth the expression levels increased significantly reaching the peak levels in the adult animal. High levels of neu1 mRNA expression were also detected in the adult dorsal root ganglia and moderate levels in the adult spinal cord. In all the tissues predominant neu1 transcripts contained intact NHR2 domain, whereas the levels the neu1 mRNAs lacking the NHR2 (neu1-ΔNHR1A and neu1-ΔNHR1B) were below 5% of all m-neu1 transcripts. Presented data show that neu1 is highly expressed during mouse and rat postnatal development and that the expression is confined to skeletal muscle and the nervous system.

EXAMPLE 3

Neuronal Expression and Dendritic Localization of Mammalian Neuralized mRNA

Figure 3:
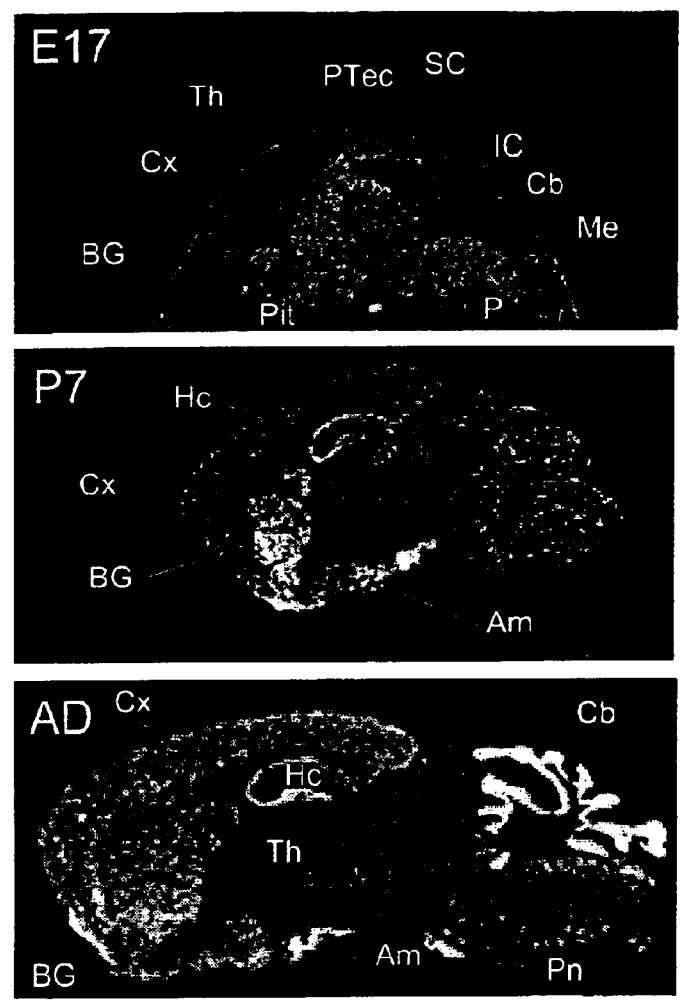
FIG. 3 is an in situ hybridization analysis of neu1 mRNA expression in the developing and adult mouse brain.

In situ hybridization analysis was used to study the cellular localization of neu1 mRNA expression in the embryonic and adult mouse brain. The results are presented in FIG. 3.

Shown are dark-field emulsion autoradiographs obtained after hybridization of coronal sections of mouse brain with the [$^{35}$S]-labeled m-neu1 cRNA probe corresponding to the first neuralized homology region (NHR1) of neu1. m-neu1 mRNA-specific labeling is shown at embryonic day 17 (E17, upper panel), at postnatal day 7 (P7, middle panel) and adult (AD, lower panel) in different brain structures. Exposure time was 3 weeks for adult and P7 sections and 6 weeks for E17 sections. As shown in the figure, BG, denotes "basal ganglia"; Cx, denotes "cerebral cortex"; Th, denotes "thalamus"; PTec, denotes "pretectum"; SC, denotes "superior colliculi"; IC, denotes "inferior colliculi"; Cb, denotes "cerebellum"; Me, denotes "medulla"; Pit, denotes "pituitary"; P, denotes "pons"; Hc, denotes "hippocampus"; Am, denotes "amygdala"; and Pn, denotes "Pontine nuclei".

Results of these analyses supported the conclusions drawn from the RPA studies discussed in Example 2. Neuralized1 mRNA-specific labeling was not detected at E13 and E15 brain, because of very low expression levels. This result was supported by the related data produced from the RPA. At E17, all brain regions, except for the cerebral cortex, hippocampus, and cerebellum, were found to express low levels of m-neu1 mRNA. In the brain, m-neu1 expression was confined to the regions containing postmitotic neurons and was not present in ventricular and subventricular zones that contain proliferating neural stem and progenitor cells.

At P7, the levels of neu1 mRNA increased significantly in the basal ganglia, amygdala, hypothalamus, and hippocampus. Low levels were present in the cerebral cortex and brainstem. In the adult, widespread expression of m-neu1 mRNA was observed throughout the brain particularly in the cerebral cortex, hippocampal formation, the basal ganglia, amygdaloid, hypothalamus, and pontine nuclei and in the cerebellum, while lower levels were seen in the mesencephalon and medulla oblangata. m-neu1 mRNA-specific signal was not detected in most of the thalamic nuclei.

Figure 4:
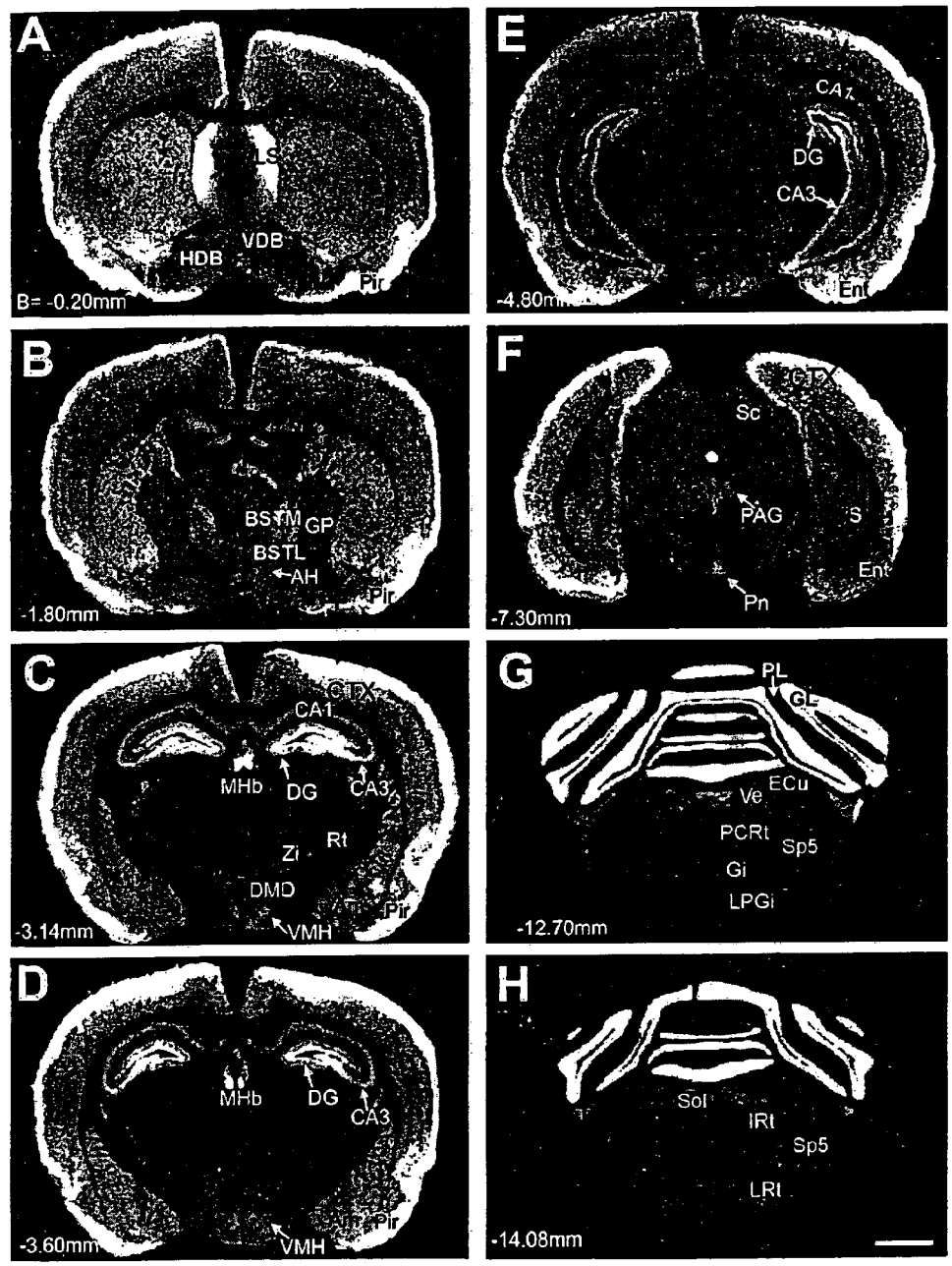
FIG. 4A–H shows an in situ hybridization analysis of neu1 mRNA expression in cerebral cortex (A–F) and in trigeminal, facial, solitary and hypoglossal nuclei (G–H) in adult rat brain. See Example 2.
Figure 5:
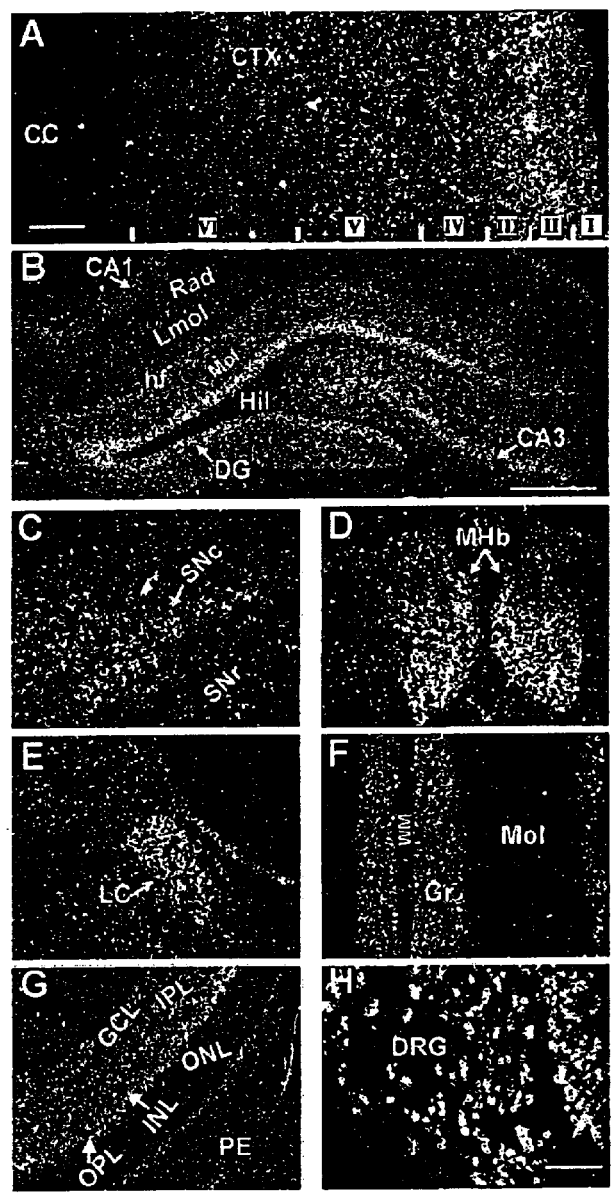
FIG. 5A–H shows an in situ hybridization analysis of neu1 mRNA expression in the adult rat nervous system. See Example 2.
Figure 6:
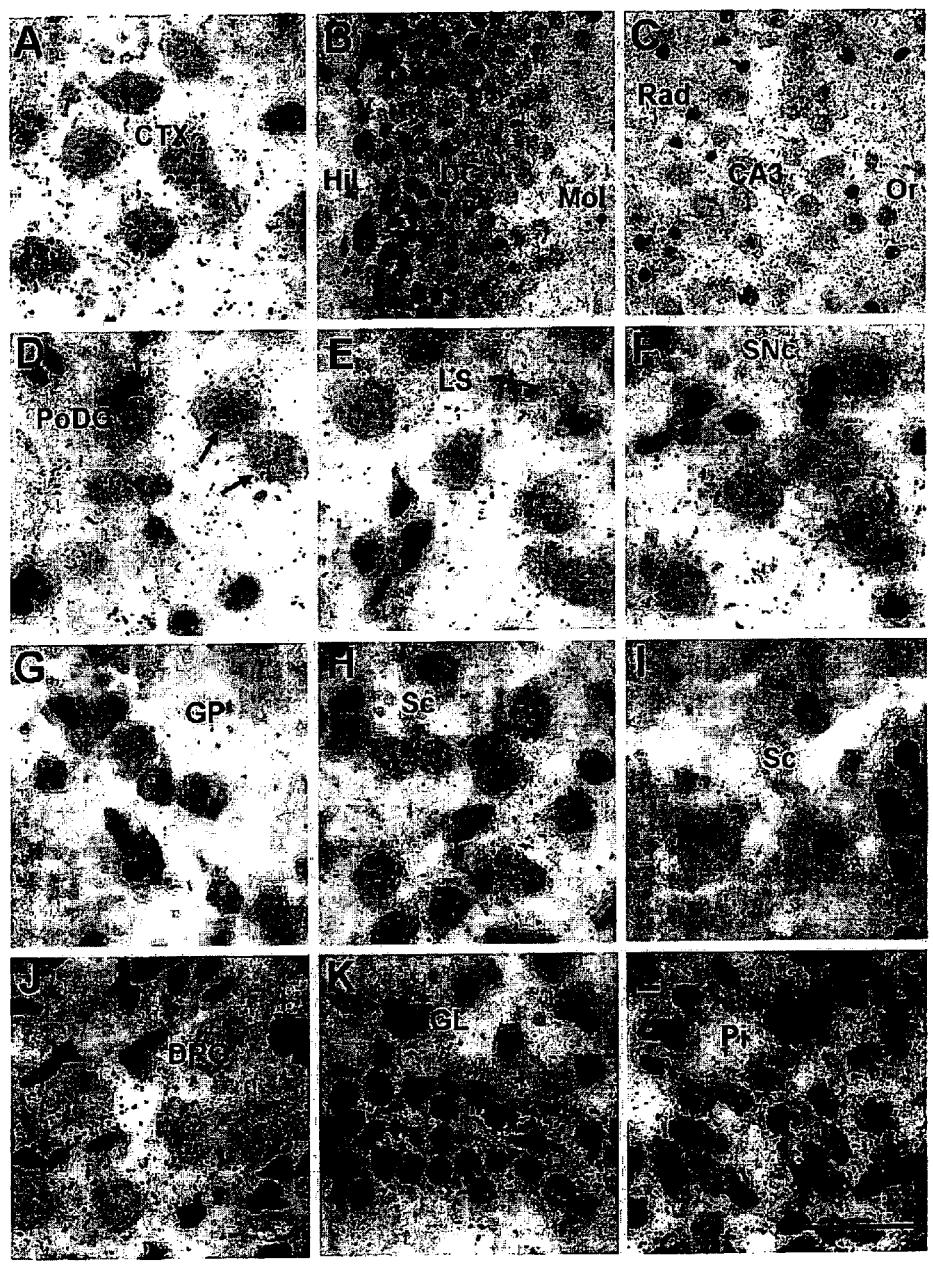
FIG. 6A–L shows an in situ hybridization analysis of the cellular localization of neu1 mRNA in the adult rat nervous system. See Example 2.

A more detailed analysis of neu1 expression was carried out in rat brain and the data is shown in Table 2 and in FIGS. 4, 5, and 6.

FIG. 4 shows the results of an in situ hybridization analysis of neu1 mRNA expression in adult rat brain. The coronal sections (A–H) correspond to the levels from Bregma in the atlas of Paxinos and Watson (Paxinus and Watson, 1986) as indicated by numbers in the left part of the bottom of each autoradiograph. CTX, denotes "cerebral cortex"; CPu, denotes "caudate putamen"; Pir, denotes "piriform cortex"; LS, denotes "lateral septum"; HDB, denotes "nucleus of the horizontal limb of the diagonal band of Broca"; VDB, denotes "nucleus of the vertical limb of the diagonal band of Broca"; GP, denotes "globus pallidus", BSTM and BSTL, denotes "bed nucleus of the stria terminalis, medial and lateral division respectively"; MHb, denotes "medial habenular nucleus"; Rt, denotes "reticular thalamic nucleus"; AH, denotes "anterior hypothalamic area"; Zi, denotes "zona incerta"; Am, denotes "amygdaloid nuclei"; VMH, denotes "ventromedial hypothalamic nucleus"; DMD, denotes "dorsomedial hypothalamic nucleus"; DG, denotes "dentate gyrus"; CA1 and CA3, denotes "pyramidal layers of the hippocampus"; Ent, denotes "entorhinal cortex"; PAG, denotes "periaqueductal gray"; Sc, denotes "superior colliculus"; S, denotes "subiculum"; Pn, denotes "pontine nuclei"; GL, denotes "granular layer of cerebellum"; PL, denotes "Purkinje cell layer of cerebellum"; ECu, denotes "external cuneate nucleus"; Ve, denotes "vestibular nuclei"; Gi, denotes "gigantocellular reticular nucleus"; Sp5, denotes "spinal trigeminal nucleus": PCRt and IRt, denote "parvicellular reticular nuclei" and "intermedial reticular nuclei", respectively; LPGi, denotes "lateral paragigantocellular nucleus"; LRt, denotes "lateral reticular nucleus"; and Sol, denotes "solitary nucleus". The scale bar corresponds to 5 mm in length.

FIG. 5 shows expression of neu1 mRNA in an adult rat nervous system. Dark-field in situ hybridization autoradiographs showing labelling in A, the cerebral cortex; B, CA1–CA3, hippocampal subfields, and in the dentate gyrus (DG) including the strata molecular (Mol), lacunosum molecular (Lmol) and radiatum (Rad); C, substantia nigra compact part (SNc) and reticular part (SNr); D, medial habenular nucleus (MHb); E, locus coeruleus (LC); F, in the molecular (Mol) and granular (Gr) layer of cerebellar cortex; G, in the layers of the retina: ganglion cell layer (GCL), inner plexiform layer (IPL), inner nuclear layer (INL), outer plexiform layer (OPL), outer nuclear layer (ONL), pigmental epitelial (PE); H, dorsal root ganglia (DRG). Roman numbers in A indicate the various layers of cerebral cortex; CC, corpus callosum; Hil, hilus; WM, white matter. The scale bars correspond lengths of 200 μm in A and 400 μm in B–H.

FIG. 6 shows cellular localization of neu1 mRNA in an adult rat nervous system. Bright-field in situ hybridization microphotographs showing labelled cells in A, in the layer II of the cerebral cortex at the level of the somatosensory cortex (CTX); B, dentate gyrus (DG) of hippocampus; C, CA3 layer of the hippocampus; D, polymorph layer of dentate gyrus (PoDG); E, lateral septum (LS); F, substantia nigra compact part (SNc); G, globus pallidus (GP); H and I, spinal cord at L3 level, respectively in the layers 9 and 2–3 (Sc); J, dorsal root ganglia (DRG); K, glia limitans (GL); L, pineal gland (Pi). Note in G, the cells in the globus pallidus (GP) do not express neu1 mRNA. Mol, stratum moleculare; Hil, hilus of the hippocampus; Rad, stratum radiatum; Or, stratum oriens. The scale bar corresponds to 25 μm in length.

Overall, although the neu1-specific labeling was distributed broadly throughout the brain, more predominant expression was confined to forebrain structures and the levels were lower in caudal regions of the brain, with the exception of some nuclei (Table 2). In the olfactory system the anterior olfactory nucleus showed neu1-specific signal. In the cerebral cortex neu1 mRNA expression levels were particularly high (FIGS. 4A–F, 5A, 6A). In the cerebral cortex, highest levels of neu1 mRNA expression were found in layer I–III, whereas expression gradually decreases from layer IV to layer VI. Dense labeling was seen in layers I–III, and in scattered neurons of layer V, moderate levels in layers V and VI, and low levels in layer IV. (FIGS. 5A, 6A) Interestingly, labeling in layer I did not cover diffuse cell bodies, suggesting dendritic localization of neu1 mRNA. Piriform and entorhinal corticies were also labeled with neu1-specific signal.

In the hippocampus, neurons of the granular layer of dentate gyrus and the pyramidal layers CA1–CA3 showed moderate-high labeling (FIGS. 4C–E, 5B, 6B–D). Neurons of the hilus and subiculum expressed low levels of neu1 mRNA. The most interesting observation regarding neu1 mRNA localization in the adult brain was the clear dendritic localization of the transcripts in the hippocampus. The neu1-specific labeling over the molecular layer of the dentate granule cells was uniformly distributed (FIG. 4C–E). Examination of emulsion-dipped sections showed that this labeling did not cover cell bodies and extended up to the hippocampal fissure, showing that neu1 mRNA is localized throughout the entire dendritic tree of dentate granule cell layer (FIGS. 5B, 6B). The strata oriens and radiatum of CA1–CA3 of hippocampus, corresponding to the dendrites of these regions, were also labeled by neu1 cRNA but the levels were significantly lower than in the molecular layer of the dentate gyrus (FIGS. 4C–E, 5B, 6C).

In the basal ganglia, r-neu1 cRNA was detected in caudate putamen and accumbens but not in the globus pallidus (FIGS. 4A, B, 6G). Moderate to high levels of neu1 mRNA were seen in all the amygdaloid nuclei (FIG. 4C–D), the interstitial nucleus of the posterior limb of anterior commissure and the bed of stria terminalis of extended amygdala (FIG. 4B). In the septum, high levels of labeling were seen in the cells of lateral septum (FIGS. 4A; 6E), and very low levels in the vertical and horizontal limb of the diagonal band of Broca. In the hypothalamus, the supraoptic, suprachiasmatic, supramammilary, and ventromedial nuclei expressed moderate levels, and several other nuclei expressed low levels of neu1 mRNA (FIG. 4B–E). In the thalamus, the medial habenula expressed high levels of neu1 mRNA, while moderate levels were observed in the reticular thalamic nucleus and low levels in a few other nuclei of the thalamus, such as the zona incerta, lateral habenula, mediodorsal thalamic nuclei, laterodorsal thalamic nuclei, paraventricular thalamic nucleus, rheuniens, rhomboid thalamic nuclei, and medial pretectal nucleus (Table 1, FIGS. 4C–D, 5D). In the mesencephalon, the neurons of the substantia nigra, colliculi superior, ventral tegmental area, periaqueductal gray, interpeduncular nucleus, oculomotor nucleus, and Raphe nucleus showed low levels of neu1-specific signal (FIGS. 4F, 5C, 6F). The granule cell layer of the cerebellum was strongly labeled, but the Purkinje cells and deep cerebellar nuclei were not (FIGS. 4G, H, 5F). Within myelenchepalon, the locus coeruleus, and the pontine, trapezoid body, facialis, pontine reticular, and rostroventrolateral reticular nuclei were labeled with moderate density with r-neu1 cRNA (Table 1, FIGS. 4F, 5E). Beyond this, there was low-density labeling in the trigeminal, facial, solitary, and hypoglossal nuclei (FIG. 4G, H). In addition, neu1 cRNA labeling was evident at low levels or in association with fewer cells in several other nuclei, such as the vestibular, cochlear, paragigantocellular, and abducens nuclei (Table 1).

In the retina, labeling of neu1 mRNA was strong in the inner nuclear layer, with the highest intensity in the outer border. Diffuse labeling was also seen in the ganglion cell layer and both in the inner and outer plexiform layers (FIG. 5G). Cells in the pineal gland expressed high levels of neu1 mRNA (FIG. 6L). Finally, labeling was relatively low in the cells of the spinal cord (FIG. 6H, I), in contrast to the neurons of dorsal root ganglia, which expressed high levels of neu1 mRNA (FIGS. 5H, 6J).

At the cellular level, m-neu1 mRNA expression was predominant in cells displaying neuronal profile (large cells with weakly stained nuclei) and not in the cells with glial profile (small cells with strongly stained nuclei). In addition, neu1 mRNA expression was not detected in the white matter, where neuronal cells are absent. One of the few exceptions of non-neuronal neu1 mRNA expression was glia limitans that displayed dense labeling (FIG. 6K).

Figure 7:
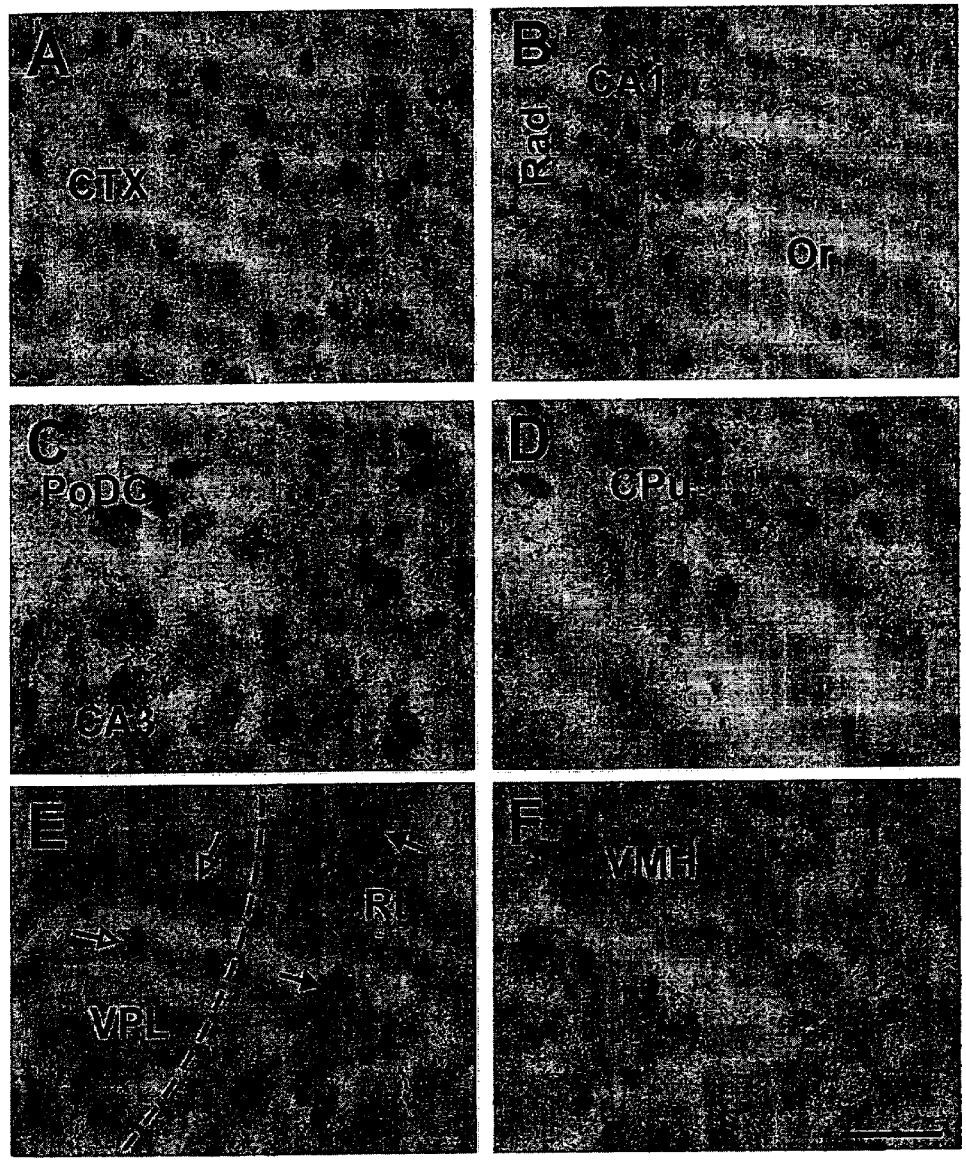
FIG. 7A–F shows the combined analyses of in situ hybridization of neu1 mRNA and immunohistochemistry of the neuronal marker neuN in adult rat brain. See Example 2.

Using in situ hybridization in combination with immunocytochemistry for NeuN, a Neuron-specific protein, we found that clusters of silver grains, reflecting the presence of neu1 mRNA, were located over the perikarya of NeuN-positive cells in all the brain regions examined, such as cerebral cortex, hippocampal formation, striatum, hypothalamus nuclei, amygdaloid complex, and cerebellum. FIG. 7 shows the results of neuronal expression studies of neu1 mRNA levels in adult rat brain. In the figure, neu1 mRNA was visualized as autoradiographic grains whereas NeuN was shown as peroxidase staining resulting in a yellow color. The two labelings co-localized with all the cells. As shown in the figure: A, layer II of cerebral cortex (CTX); B, CA1 layer of the hippocampus; C, polymorph layer of the dentate gyrus (PoDG) and CA3 layer of the hippocampus; D, caudate putamen (CPu); E, reticular thalamic nucleus (Rt); and F, ventromedial hypothalamic nucleus (VMH), were studied. Note that neurons (NeuN-positive cells) of the ventral posterolateral thalamic nucleus (VPL) in E do not express neu1 mRNA.

By evaluation the proportion of cells positive for both neu1 mRNA and NeuN out of the total number of NeuN-containing neurons, it was found that all the neurons in the layers II and III of the cerebral cortex expressed neu1 mRNA. In the layer IV eighty percent and layers V–VI about ninety percent of neurons expressed neu1 mRNA. In several other brain regions examined, such as hippocampal formation, striatum, reticular thalamic nucleus, hypothalamic nuclei, showing that the majority of the neuronal cells express neu1 mRNA. In contrast, neurons in the globus pallidus and in several thalamic nuclei, such as ventral posterolateral and posteromedial nuclei, did not express neu1 mRNA (FIG. 7).

Figure 8:
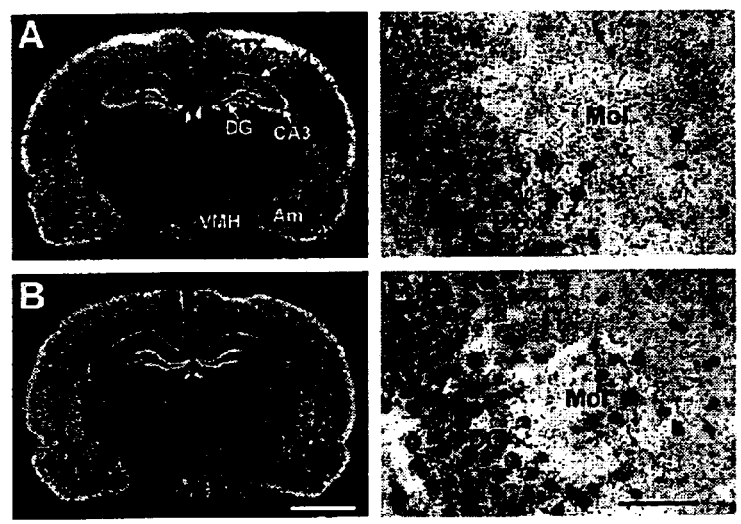
FIG. 8 shows neu1 mRNA expression in the hippocampus of adult rat brain after kainic acid treatment panels A and A1 are control brains; and panels B and B1 are the brains treated with kainic acid.

Neuronal activity has been shown to regulate the dendritic localization of the immediate-early gene arc mRNA. Steward et al., Neuron, 21:741–51 (1998); Guzovsky et al., Nat Neurosci, 2:1120–1124 (1999). To examine if neu1 mRNA dendritic localization is regulated by neuronal activity, the effect of kainate-induced seizures on the expression and localization of neu1 mRNA was studied (FIG. 8). At 24 hours after the injection of kainate, neu1 mRNA levels decreased in all the regions of the hippocampus. The levels of neu1 mRNA are significantly downregulated in the granular and molecular layers of dentate gyrus of adult rat brain at 24 hours after the treatment with kainic acid (B and B1), as compared to control brains (A and A1). Regions analyzed are denoted as follows: CTX, cerebral cortex; DG, dentate gyrus; Am, amygdala; Pir, piriform cortex; VMH, ventromedial hypothalamic nucleus; and Mol, for the molecular layer of the hippocampus. Particularly pronounced was the reduction of labeling in the molecular layer of the dentate gyrus. Similarly, but less consistently, a down-regulation of neu1 mRNA was observed in the cerebral cortex.

EXAMPLE 4

Neu1 Protein Isoforms Exhibit Transcriptional Repressor Activities

The ability of m-Neu1 to act as a transcriptional regulator was studied using a chloramphenicol acetyl-transferase (CAT) assay. Several transcriptional regulators, such as the polycomb group-related transcriptional regulator MEL 18, the MDM2 proto-oncogene, breast and ovarian cancer susceptibility gene BRCA1 and MAT1, a subunit of TFIIH basal complex factor contain RING finger motifs. Kanno et al., $EMBO\ J$, 14:5672–5678 (1995); Leveillard and Wasylyk, $J\ Biol\ Chem$, 272:30651–30661 (1997); Pao et al., $Proc\ Natl\ Acad\ Sci\ USA$, 97:1020–1025 (2000); and Fesquet et al., $Oncogene$, 15:1303–1307 (1997). Furthermore, the earlier studies proposed d-Neu to function as a DNA-binding transcription factor. Boulianne et al., $EMBO\ J$, 10:2975–2983 (1991) and Price et al., $EMBO\ J$, 12:2411–2418 (1993).

The effect of m-Neu1 on transcriptional activity was studied using a chloramphenicol acetyl-transferase (CAT) assay and the following promoters: 1) TATA-box containing: 1.0 kb BDNF-I-CAT, 0.3 kb BDNF-11-CAT, 0,7 kb BDNF-IV CAT, 0.4 kb NF-L, 1.0 kb GAP-43, 2) TATA-less promoters with putative initiators (Inr): 0.4 kb BDNF-III-CAT, 0.4 kb LNGFR-CAT, and 0.3 kb MEL-CAT. Timmusk et al., $Neuron$, 10:475–489 (1993); Reeben et al., $J\ Neurosci\ Res$, 40:177–188 (1995); Chiaramello et al., $J\ Biol\ Chem$, 271:22035–22043 (1996); Metsis et al., $Gene$, 121:247–254 (1992); and Shain et al., $Nucleic\ Acids\ Res$, 23:1696–1703 (1995). Data from the study is shown in FIG. 9.

Figure 9:
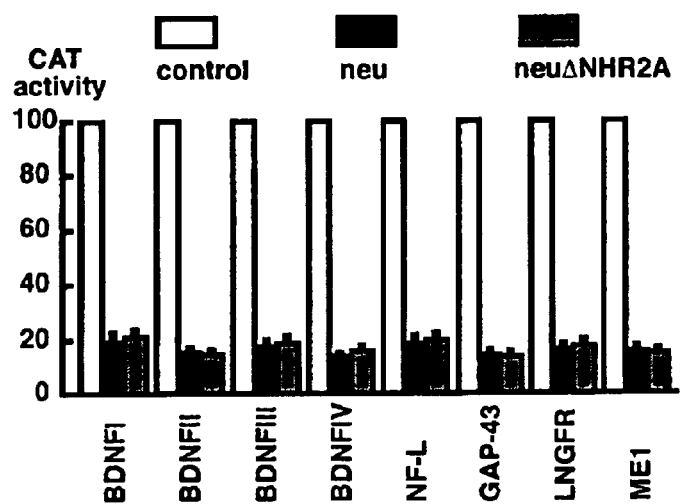
FIG. 9 shows transcriptional analysis from various promoters in transient expression assays.

FIG. 9 show that Neu1 represses transcription from various promoters in transient expression assays. The data for this figure was gathered from Neuro2A cells that were co-transfected with 0.5 μg of various reporter plasmids containing different promoters driving the epression of CAT and pRcCMV expression plasmid (1.0 μg) without any cDNA sequence (control) or containing m-neu1 cDNAs encoding the full length protein (neu-FL) or the m-Neu-1-ΔNHR2A (neuΔNHR2A) isoform lacking the region between NHR1 and RZD, using FuGENE-6 transfection system. The pON260 expression plasmid (0.1 μg) encoding β-galactosidase was included in the transfections to normalize the transfection efficiencies. The CAT activity is defined as 100 for each reporter when cotransfected with the pRc-CMV parental expression plasmid. When cotransfected with expression plasmids containing m-neu1 cDNAs, the CAT activities are expressed relative to the value obtained by cotransfection of each reporter plasmid and the parental pRcCMV expression plasmid. The data shown are representative of at least three independent experiments. Error bars represent the S.E. BDNF-I, 1.0 kb BDNF promoter I, BDNF II, 0.3 kb BDNF promoter II; BDNF III, 0.4 kb BDNF promoter III; BDNF IV, 0.7 kb BDNF promoter IV; NF-L, 0.4 kb NF-L promoter; GAP-43, 1.0 kb GAP-43-promoter, LNGFR, 0.4 kb LNGFR promoter; ME1, 0.3 kb ME1 promoter.

The full-length and the isoform of m-Neu1-ΔNHR2A significantly reduced the activity of all of these promoters in Neuro-2A cells (FIG. 9). CAT assays performed in other cell types (mouse teratocarcinoma PCC7, rat astrocytoma C6, human breast ductal carcinoma BT-549, human primary osteogenic sarcoma Saos2, human cervix carcinoma C-33A) or using a different reporter (RARβ promoter driven lac Z) gave similar results (data not shown), suggesting that the transcriptional repressor activity of m-Neu1 does not depend on the reporter and cellular context.

Following the identification of m-Neu1's activity as a transcriptional regulator, identification of the repression domains of m-Neu1 was performed. Expression plasmids were generated encoding full-length m-Neu1 or individual domains of m-Neu1 fused to Gal4 DNA-binding domain and tested their activities by CAT assays. The data is presented in FIG. 10.

Figure 10:
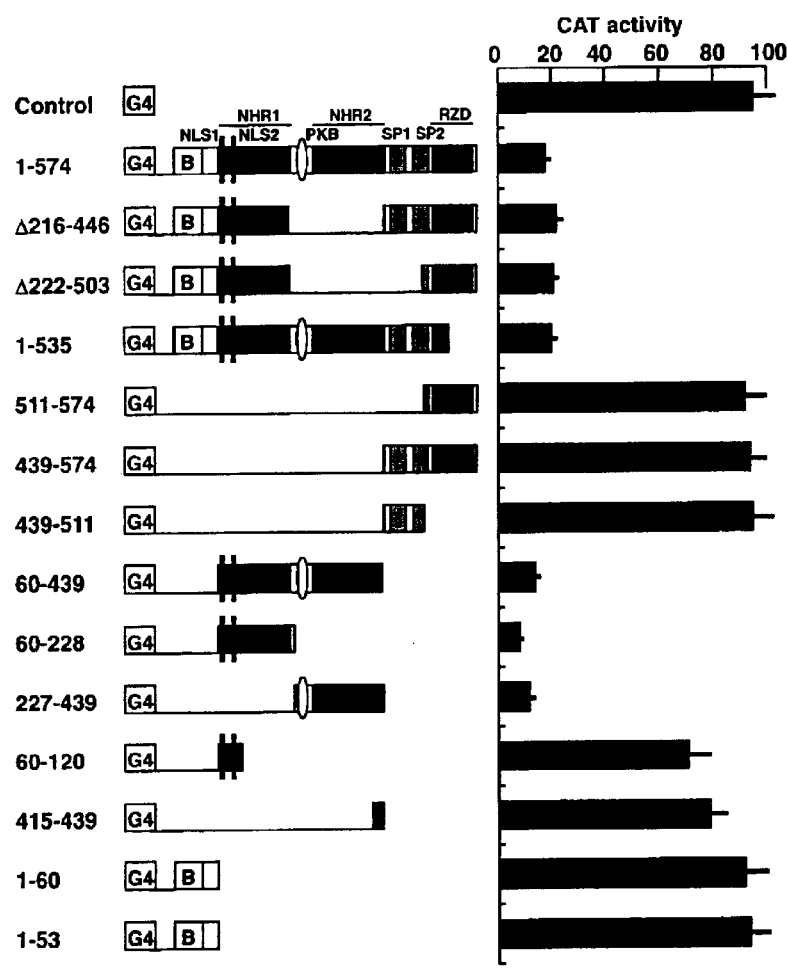
FIG. 10 shows that neuralized homology repeat domains of neu1 mediate the transcriptional repression when fused to the DNA binding domain of Gal4.

FIG. 10 shows that neuralized homology repeat domains of Neu1 mediate the transcriptional repression when fused to the DNA binding domain of Gal4. Neuro2A cells were cotransfected with Gal4TK-CAT reporter plasmid containing five Gal4 binding sites in front of TK promoter driving the expression of CAT (0.5 μg) and pBIND expression plasmid (1.0 μg) without any cDNA sequence (G4) or containing different regions of m-neu1 cDNA fused in-frame to Gal4 DNA-binding domain using FuGENE-6 transfection system. The designations of the constructs are shown on the left of FIG. 10. The CAT activities are expressed relative to the value obtained by cotransfection of the reporter plasmid and the parental pRcCMV expression plasmid which was set 100. The data shown are representative of at least three independent experiments. Error bars represent the S.E.

The co-transfection of full-length m-Neu1 fused to Gal4 (Gal4-m-Neu1) with the Gal4-TK-CAT resulted in a concentration-dependent repression of the CAT activity (FIG. 10). m-Neu1 isoforms that lack the NHR2 and the region preceding the RZD also displayed transcriptional repressor activities when fused to Gal4 DBD (FIG. 10). Extensive deletion analyses showed that NHR1 and NHR2 domains possess transcriptional repressor activity, whereas neural and muscle-specific N-termini (amino acids 1–60), RZD (amino acids 509–574) and the serine-proline rich linker region joining RZD to NHR2 (amino acids 439–510) did not affect transcription (FIG. 10). Interestingly, individual NHR1 and NHR2 displayed even stronger repressor activities than the full-length m-Neu1. These data show that m-Neu1 acts as a transcriptional repressor when tethered to a promoter via a heterologous DNA binding domain (DBD). To summarize, m-Neu1 represses the activity of both TATA and TATA-less promoters in transient expression assays.

EXAMPLE 5

Nucleocytoplasmic Shuttling of Neu1 Protein

The function of Neu1 as a transcriptional repressor implies its nuclear localization. A putative lysine rich nuclear localization signal (NLS) that is present in d-Neu protein (d-NLS) is not conserved in mammals. Boulianne et al., $EMBO\ J$, 10:2975–2983 (1991) and Price et al., $EMBO\ J$, 12:2411–2418 (1993). To study the subcellular localization of m-Neu1 protein expression constructs were generated encoding tagged m-Neu-fusion proteins. The expression of these vectors was analyzed in Neuro2A cells.

Figure 11:
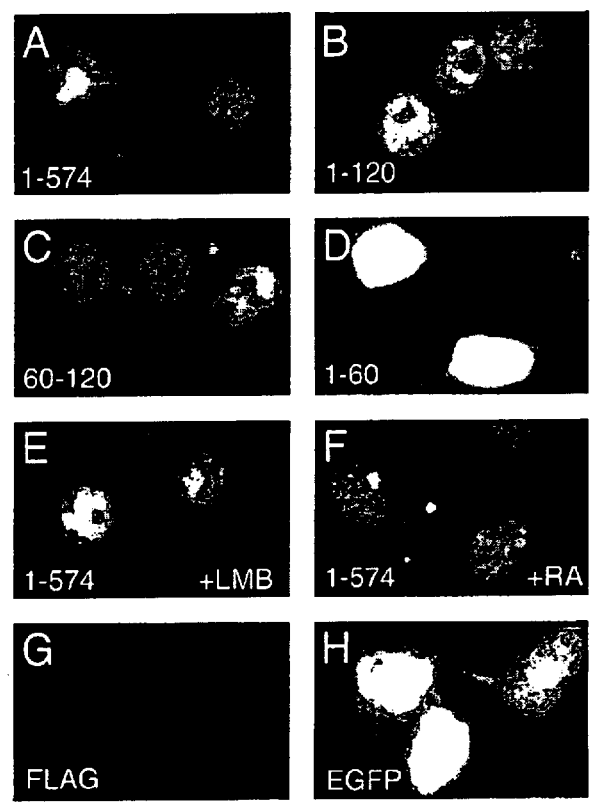
FIG. 11 shows the subcellular localization of neu-FLAG and neu-EGFP fusion proteins in Neuro2A cells, using FLAG immunofluorescence using anti-FLAG antibody (A, E, F, G) and direct fluorescence of EGFP fusion proteins (B, C, D, H).

The results from this work is shown in FIG. 11. This figure shows the subcellular localization of m-Neu1-FLAG and m-Neu1-EGFP fusion proteins in Neuro2A cells. Neuro2A cells were transfected expression plasmids encoding m-Neu1-FLAG (A, E, F) and different m-Neu1-EGFP (B, C, D) fusion proteins or with parental pFLAG (G) and pEGFP-C3 (H) expression plasmids. Numbers indicate the amino acids of Neu1 fused to the C-terminal of FLAG and EGFP. Presented are images of FLAG immunofluorescence using anti-FLAG antibody (A, E, F, G) and direct fluorescence of EGFP fusion proteins (B, C, D, H).

More specifically, A, shows the Neu1-FLAG fusion protein is localized either in the cytoplasm or in the nucleus; B, shows that Neu1/120-EGFP fusion protein containing amino acids 1–120 of Neu1 exhibits constitutive nuclear localization in all cells; C, shows that the Neu1-60/120-EGFP fusion protein is seen exclusively in the nucleus revealing that the first 60 amino acids of NHR1 are sufficient for nuclear localization of Neu1; in D, the Neu1-1/60-EGFP fusion protein containing the N-terminal 60 amino acids of the brain-specific isoform of m-Neu1 shows localization that is identical to H, localization of EGFP synthesized from the parental pEGFP-C3 expression plasmid; E, inhibition of nuclear export of Neu1-FLAG fusion protein by treatment of Neuro2A cells with leptomycin B (10 ng/ml) for 12 hours or F, 2 days of RA and dBcAMP mediated differentiation leads to predominant nuclear localization of Neu1-FLAG fusion protein; G, FLAG synthesized from parental plasmid is distributed evenly in the cell.

The fusion protein m-Neu1-FLAG comprised of the full-length m-Neu1 with N-terminal FLAG tag showed either predominantly nuclear (~40% of the positive cells) or predominantly cytoplasmic (~60% of the positive cells) distribution. If localized in the cytoplasm, m-Neu1-FLAG fusion protein was observed in the form of granular speckles in the perinuclear area, in the vicinity of plasma membrane and in neurites (FIG. 11A).

m-Neu1 does not have sequences that are similar to the lysine-rich d-NLS, however, two smaller clusters of arginine and lysine rich amino acids (HKAVKAR (SEQ ID NO: 43) at 80–85 and RLKITKK (SEQ ID NO: 44) at 107–113) are present in the NHR1 of m-Neu1 (FIG. 1). To investigate whether these putative NLSs are functional, the subcellular localization of m-Neu1 deletion mutants fused to the C-terminus of EGFP were analyzed in living cells. Neu-1/120-EGFP fusion protein containing the first 120 amino acids of m-Neu1 displayed nuclear localization in virtually all the cells (100%) (FIG. 11B). Deletion of the first 60 amino acids from the N-terminal region of m-Neu1 up to the NHR1 domain (Neu-60/120-EGFP) did not change the predominant nuclear localization of the Neu-1/120-EGFP fusion protein (FIG. 11C). The N-terminal region of Neu1 fused to EGFP (Neu1/120-EGFP) displayed overall cellular distribution of the fusion protein (FIG. 11D) which was identical to the localization of EGFP (FIG. 11H). These results showed that the region containing the first 60 amino acids of NHR1 (amino acids 60–120) including two putative NLS domains are sufficient for nuclear import of m-Neu1.

Localization of m-Neu1 fusion proteins in the nucleus and cytoplasm suggest that m-Neu1 transport could be the subject of regulation. Various proteins have been shown to be exported from the nucleus by the CRM1/exportin1-related export pathway that is blocked by the antibiotic leptomycin B (LMB), a specific inhibitor of nuclear export mediated by leucine-rich nuclear export signals (NES). Hood and Silver, Curr Opin Cell Biol, 11:241–247 (1999); Izaurralde and Adam, RNA, 4(:351–364 (1998); Ullman et al., Cell, 90:967–970 (1997); Weiss (1998); Fornerod et al., Cell, 90:1051–1060 (1997); Fukuda et al., Nature, 390:308–311 (1997); Kudo et al., Exp Cell Res, 242:540–547 (1998); Kudo et al., Proc Natl Acad Sci USA, 96:9112–9117 (1999); and Nishi et al., J Biol Chem, 269:6320–6324 (1994). m-Neu1 protein contains two putative leucine-rich sequences, one in the end of each of the NHR (FIG. 1), that are similar to the identified NES in different proteins. Kogerman et al., Nat Cell Bio, 1:312–319 (1999); Taagepera et al., Proc Natl Acad Sci USA, 95:7457–7462 (1998); Ullman et al., Cell, 90:967–970 (1997); and Yamaga et al., J Biol Chem, 274:28537–28541 (1999). In view of these results, the effect of LMB on the localization of m-Neu-FLAG in Neuro2A cells was next studied.

Treatment of Neuro2A cells transfected with m-Neu1-FLAG expression construct with LMB (10 ng/ml) resulted in exclusively nuclear localization of m-Neu1-FLAG at 12 hours post-treatment in virtually all the cells (FIG. 11E). These results suggest that m-Neu1 protein shuttles between nucleus and cytoplasm, and that the CRM1/exportin1-related pathway is involved in nuclear export.

Interestingly, the number of cells with nuclear localization of m-Neu1-tagged protein increased substantially (from 45% to 80%) 12 hs after the RA- and cAMP-mediated neuronal differentiation (FIG. 11F). It suggests that neuronal differentiation changes the mechanisms that are responsible for the translocation of m-Neu1 protein in Neuro2A cells.

EXAMPLE 6

Characterization of Neu1 Homologs Neu2, Neu3 and Neu4

Screening of cDNA libraries and RT-PCR amplification has resulted in isolation of several homologs of mammalian neu1 genes. Polynucleotide sequences of the following homologs are presented as SEQ. ID. NOS.: human neu2 cDNA of SEQ. ID. NO.:21; human neu2 alternatively spliced form h-neu2-ΔNHR1 of SEQ. ID. NO.:23; human neu2 alternatively spliced form h-neu2-ΔNHR2 of SEQ. ID. NO.:25; rat neu2 cDNA SEQ. ID. NO.: 27; human neu3 cDNA of SEQ. ID. NO.: 29; mouse neu3 cDNA of SEQ. ID. NO.: 31; and human neu4 cDNA (partial) of SEQ. ID. NO.: 33. Corresponding peptide sequences are presented as SEQ. ID. NOs: human Neu2 protein of SEQ. ID. NO.: 22; human Neu2 alternatively spliced form h-neu2-ΔNHR1 of SEQ. ID. NO.:24;; human Neu2 alternatively spliced form h-neu2-ΔNHR2 of SEQ. ID. NO.:26; rat Neu2 protein SEQ. ID. NO.: 28; human Neu3 protein of SEQ. ID. NO.: 30; mouse Neu3 protein of SEQ. ID. NO.: 32; and human Neu4 protein (partial) of SEQ. ID. NO.: 34. All the mammalian Neu proteins show significant homology in the NHR and Ring zinc finger domains.

Alignment of neuralized homology motifs of human Neu1, Neu2, and Neu3 proteins is shown in FIG. 12. Amino acid sequence comparison of the neuralized homology regions (NHR) of Drosophila neu and human neu1, neu2 and neu3 proteins is shown in FIG. 12. Amino acids that are identical in human and Drosophila neu proteins are highlighted in white on black background. Amino acids that are similar in human and Drosophila neu proteins are boxed and highlighted on grey background. h1I, NHR1 of human neu1; h2I, NHR1 of human neu2; h3, NHR of human neu3; dI, NHR1 of Drosophila neu; dII, NHR2 of d-neu; h1II, NHR2 of human neu1; h2II, NHR2 of human neu2.

Figure 13:
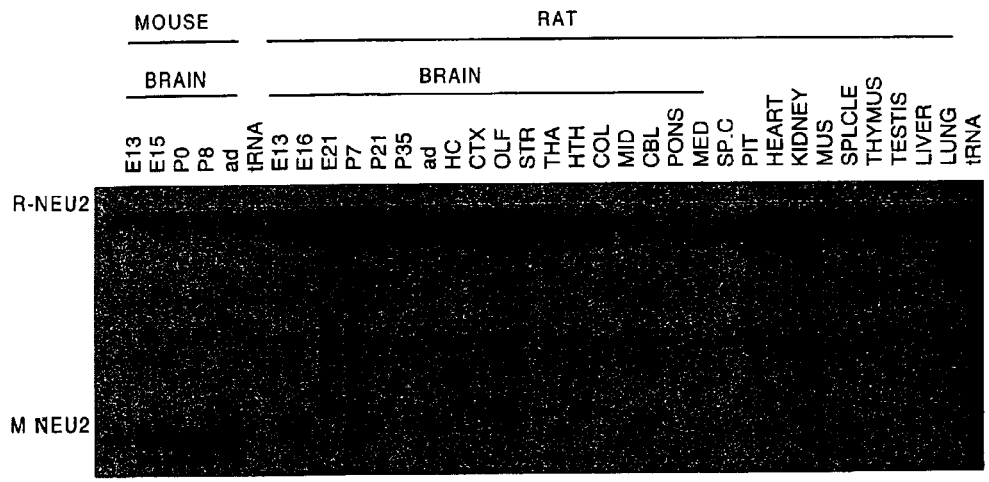
FIG. 13 shows the analysis of neu2 mRNA expression by RNase protection assay in mouse and rat.
Figure 14:
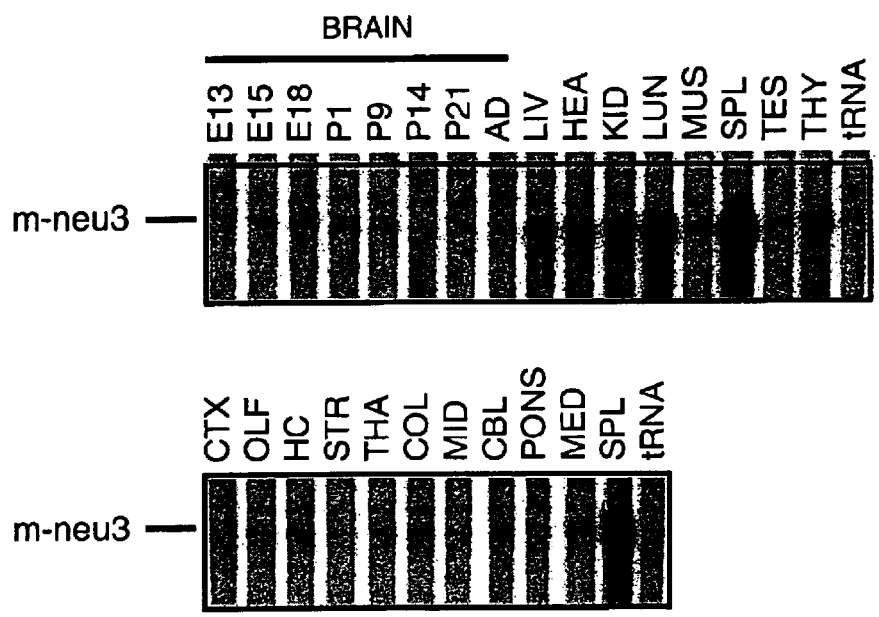
FIG. 14 shows the analysis of neu3 mRNA expression by RNase protection in mouse.

Expression of neu1 mRNA is highest in adult, mature neurons (FIGS. 2–7). neu2, in contrast to neu1, is expressed at high levels already in the embryonic brain and the expression levels decrease during postnatal development (FIG. 13). Total RNA was isolated from the indicated mouse and rat brain regions and non-neural tissues and the levels of neu2 transcripts were analyzed by RNase protection assays. cRNA probes that were used for detection of neu2 transcripts covered the region encoding the NHR1 of rat neu2. Specific protected fragments are indicated on the left of the panel. R-NEU2, rat neu2 transcript; M-NEU2, mouse neu2 transcript. E, Embryonic day; P, postnatal day; ad, adult; HC, hippocampus; CTX, cerebral cortex; OLF, olfactory bulb; STR, striatum; THA, thalamus; HTH, hypothalamus; COL, colliculi; MID, ventral midbrain; CBL, cerebellum; PONS, pons; MED, medulla; SP. C, spinalcord; PIT, pituitary; MUS, muscle; SPLCE, spleen tRNA, yeast tRNA as a negative control.

neu3 is widely expressed, with highest levels in immune tissues spleen and thymus, and in the lung (FIG. 14). Total RNA was isolated from the indicated mouse brain regions and non-neural tissues and the levels of neu3 transcripts were analyzed by RNase protection assays. cRNA probes that were used for detection of neu3 transcripts covered the region encoding the NHR of mouse neu3. Specific protected fragments are indicated on the left of the panel. E, Embryonic day; P, postnatal day; AD, adult; HC, hippocampus; CTX, cerebral cortex; OLF, olfactory bulb; STR, striatum; THA, thalamus; COL, colliculi; MID, midbrain; CBL, cerebellum; PONS, pons; MED, medulla; LIV, liver; HEA, heart; KID, kidney; LUN, lung; MUS, muscle; SPL, spleen; TES, testis; THY, thymus; tRNA, yeast tRNA as a negative control.

Expression of neu4 was detected only in muscle and heart.

EXAMPLE 7

Isolation and Characterization of Factors Interacting with Neu1

An adult rat brain library was screened using a yeast two hybrid system with a mouse Neu1 protein as a ligand with which to isolate and identify proteins that interact with Neu1. Fifty-three (53) clones were isolated. cDNAs that yielded more than 1 clone were sequenced and identified as four interactors: NeuI-1, NeuI-2, NeuI-3, and NeuI-4.

Sequence analyses showed that all interactors were novel proteins and contain RING finger domain located in the C-terminus of the protein. NeuI-1 (4 clones) is a novel splice variant (SEQ. ID. NO.: 29) of zinc finger protein Miz1/PIASX/ARIP3 (GenBank accession number NM_008602; AF077953; AF077954; AF044058). NeuI-2 (3 clones) is a fourth homologue (SEQ. ID. NO.: 30; GenBank accession number AF277171; AF302084) of zinc finger protein ZNF127 (GenBank accession number U19106; U19107), NeuI-3 (9 clones) has highest homology to a human hypothetical protein (GenBank accession number AK001459) and to a Drosophila hypothetical protein (AAF56052.2) produced from CG4813 gene of a genomic scaffold (GenBank accession number AE003740) (SEQ. ID. NO.: 31), and NeuI-4 (12 clones) is the homologue of the androgen receptor co-activator ARA54 (SEQ. ID. NO.: 32; GenBank accession number AF060544).

Figure 15:
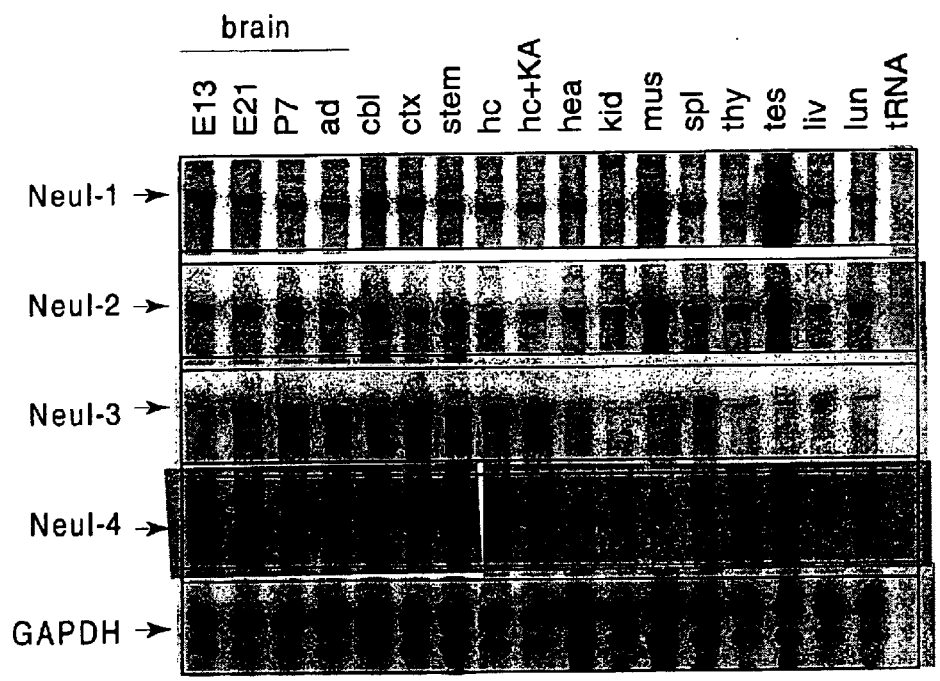
FIG. 15 is an analysis of the expression of rat Neu1 interactors by RNase protection assay.

Expression of neuI-1-neuI-4 mRNAs was analyzed in developing and adult rat brain and non-neural tissues (FIG. 15). Total RNA was isolated from the indicated rat tissues and the levels of transcripts were analyzed by RNase protection assays with cRNA probes specific for NeuI-1, NeuI-2, NeuI-3 and NeuI-4 transcripts. Specific protected fragments are indicated on the left of each panel. Bottom panel shows the levels of GAPDH mRNA in the RNA samples. E, Embryonic day; P, postnatal day; ad, adult; cbl, cerebellum; ctx, cerebral cortex; stem, brainstem; hc, hippocampus; hc+KA, hippocampus from rats treated for 4 h with the glutamate receptor agonist kainic acid; hea, heart; kid, kidney; mus, skeletal muscle; spl, spleen; thy, thymus; tes, testis; li, liver; lu, lung; tRNA, yeast tRNA as a negative control.

All the identified Neu1 interactors were expressed in the brain and skeletal muscle, tissues where neu1 mRNA is predominantly expressed. This suggests that neuI-1-neuI-4 interact with Neu 1 protein and modify its activity in vivo.

EXAMPLE 8

Neu1 Affects the Activation of Immediate Early Genes (IEGs)

The function of Neu1 as a calcium-dependent transcriptional repressor was studied by transfecting Neuro2A cells with m-neu1-CMV expression vector. This system was used to examiner whether or not Neu1 could suppress transcription of IEGs in response to the simultaneous stimulation of cells with calcium, ionophore A23187, and forskolin. As a combination of forskolin with calcium, ionophores leads to increased c-fos mRNA levels in Swiss 3T3 cells (Mehmet H, 1990). Because the induction of immediate early genes by $Ca^{2+}$ influx requires cAMP-dependent protein kinase in PC12 cells (Ginty DD, 1991), it was decided to apply the forskolin and ionophore co-treatment to Neuro-2A cells.

Upon transient transfection of m-Neu1 into Neuro2A cells, activation of transcription of several IEGs (c-fos, junB, junD, c-jun, fra-1, and fra-2) from their endogenous promoters was significantly reduced in response to the raised intracellular $Ca^{2+}$ (Ca ionophore) and cAMP activity (forskolin) levels. Neu1 elevated levels affected the amplitude of the IEG mRNA induction, however, had no effect on the time course of induction. This finding couples Neu1 to stimulus (calcium)-dependent transcriptional regulation.

EXAMPLE 9

Interaction with TBP

Because m-Neu1 affects a variety of target gene promoters in transient transfection assays, it was hypothesized that m-Neu1 functions by interfering directly with the function of Pol II complex, particularly suppressing the TBP transcriptional activity. To examine this possibility, m-Neu-CMV expression constructs were cotransfected together with m-TBP-CMV. The effect of this procedure on thymidine kinase (tk) promoter was examined. Increasing amounts of Neu-CMV while mTBP-CMV amounts were kept constant (and vice versa) resulted in the decreased activity of the reporter gene in Neuro2A cells. These results suggested that m-Neu1 could repress transcription by direct interaction with TBP.

EXAMPLE 10

Neoplastic Diagnostic Assay Using Genomic DNA

A biopsy is obtained from a subject possibly suffering from a neoplastic disease, such as an astrocytoma. Following excision of the sample, the tissue is immediately minced and quickly frozen in liquid nitrogen. A sample 1 gram sample of tissue is then ground with a prechilled mortar and pestle for suspension. The ground tissue is then suspended in approximately 1.2 ml of digestions buffer (100 mM NaCl, 10 mM Tris-Cl, pH 8.0, 25 mM EDTA, pH 8.0, 0.5% (w/v) SDS, and 0.1 mg/ml proteinase K, which is added fresh for each use). Samples are shaken and incubated for 12 to 18 hours at 50° C.

Following the incubation period, the samples are extracted with an equal volume of phenol/chloroform/isoamyl alcohol, to remove proteinatious material. Centrifuge the mixture for 10 minutes at 1700×g. If phases do not resolve well, add another volume of digestion buffer, omitting proteinase K, and repeat centrifugation. Repeat the extraction until no thick white material appears at the interface. Transfer the top aqueous layer to a new tube.

To this tube is added ½ volume of 7.5 M ammonium acetate and 2 volumes of 100% ethanol. This mixture is centrifuged for 2 minutes at 1700×g. Following the centrifugation, the resulting pellet is washed with 70% ethanol, and then air dried and will be resuspended in Tris-EDTA buffer at approximately 1 mg/ml.

To prevent shearing of high molecular weight DNA it may be advisable to remove organic solvents and salt by two dialyses against 100 volumes of Tris-EDTA buffer for more than 24 hours. If this step is performed, the pellet is not resuspended in Tris-EDTA buffer.

The purified DNA is analyzed for the presence or mutation of a wild type copy of a neu family gene using Southern Blotting and sequencing. The absence or mutation of such in the subject indicates the presence of a malignancy.

EXAMPLE 11

Neoplastic Diagnostic Assay Using RNA Analysis

A tissue sample is obtained from a subject possibly suffering from a neoplastic disease. The biopsy is removed and cut into less than 2 gram pieces. These pieces are quick-frozen in liquid nitrogen. Twenty (20 ml) of tissue guanidinium solution is used to process 2 grams of tissue. The tissue guanidinium solution is prepared by dissolving 590.8 grams of guanadinium isothiocyanate in approximately 400 ml DEPC-treated $H_2O$. To this is added 25 ml of 2M Tris-Cl, pH 7.5 (0.05 M final) and 20 ml of 0.5 M $Na_2EDTA$, pH 8.0 (0.01 M final). Stir overnight, adjust the volume to 950 ml, and filter. Finally, add 50 ml 2-mercaptoethanol (2-ME).

Once the tissue guanidinium solution is added to the tissue, the sample is immediately ground in a tissuemizer with two or three ten second bursts. Following disruption, the solution is subjected to centrifugation for 10 minutes at 12,000×g in a SS-34 rotor, at 12° C. To the supernatant is added 0.1 volumes of 20% Sarkosyl. This mixture is then subjected to heat at 65° C., for 2 minutes.

To this heated solution is added 0.1 grams of CsCl/ml of solution, which is mixed until it dissolves. The sample is next layered over 9 ml of 5.7M CsCl in silanized and autoclaved SW-28 tubes. These tubes are centrifuged overnight at 113,000×g in a SW-28 rotor at 22° C.

Following the centrifugation step, the supernatant is removed and the tubes are inverted to drain. The bottom of each tube is removed and the RNA pelleted contained therein is placed in a 50-ml plastic tube. Three (3) ml of tissue resuspension buffer and allow pellet to resuspend overnight or longer at 4° C. Extract solution sequestially with 25:24:1 phenol/chloroform/isoamyl alcohol, then with 24:1 chloroform/isoamyl alcohol. Add 0.1 volume of 3 M sodium acetate, pH 5.2, and 2.5 volume of 100% ethanol, precipitate, and resuspend RNA in water. The sample is quantitated and analyzed for the expression of the neu family of genes. Samples with aberent expression levels indicate the presence of neoplastic cells.

EXAMPLE 12

Ex Vivo Exogenous Gene Expression

Cells are isolated from a subject to be transfected with a construct encoding Neu protein (Neu construct). The Neu construct is transfected using DEAE-dextran. The cells are seeded in 6-well tissue culture plates and are transfected with a total of 1–2 µg of total DNA containing the Neu contruct. After 5 hours, 1 ml of DMEM containing 20% fetal bovine serum is added and the cells are allowed to incubate overnight.

Expression of Neu is then determined using immunoprecipitation with an antibody-agarose conjugate (8 µg) plus 25 µl of a 50% slurry of Protein A-agarose. Immune complexes are washed in a wash buffer (20 mM Hepes, pH 7.4, 10 mM $MgCl_2$, and 1 mM DTT). The immune complexes are placed in a denaturing protein sample buffer that separated the antibody from any bound antigen. The protein samples are then run on SDS-polyacrylamide gel electrophoresis to detect the expression of a target Neu protein.

The foregoing description details certain embodiments of the invention. It will be appreciated, however, that no matter how detailed the foregoing appears in the text, the invention can be practised in many ways. Although this invention has been described in terms of certain preferred embodiments, other embodiments which will be apparent to those of ordinary skill in the art in view of the disclosure herein are also within the scope of this invention. As is also stated above, it should be noted that the use of particular terminology when describing certain features or aspects of the invention should not be taken to imply that the terminology is being re-defined herein to be restricted to include any specific characteristics of the features or aspects of the invention with which that terminology is associated. Accordingly, the scope of the invention should therefore be construed in accordance with the appended claims and any equivalents thereof.

What is claimed is:

1. A purified polynucleotide encoding a neuralized (Neu) polypeptide is capable of suppressing transcription and comprises at least one neuralized homology repeat domain an C3HC4 RING-zinc finger domain, and wherein said polynucleotide has at least 90% sequence identity to SEQ ID NO: 21.

2. The purified polynucleotide of claim 1, wherein said polynucleotide has at least 95% sequence identity to SEQ ID NO: 21.

3. The purified polynucleotide of claim 1, wherein said polynucleotide comprises SEQ ID NO: 21.

4. An expression vector comprising a polynucleotide according to claim 1.

5. The expression vector of claim 4, wherein the vector is a plasmid.

6. A host cell containing the expression vector of claim 4.

7. A method of making a Neu protein, comprising: obtaining a polynucleotide comprising a nucleotide sequence encoding a Neu protein, inserting said polynucleotide into an expression vector such that said nucleotide sequence is operably linked to a promoter, and introducing said expression vector into a host cell, wherein said nucleotide sequence has at least 90% sequence identity to a SEQ ID NO: 21, and whereby said host cell produces said Neu protein encoded by said nucleotide sequence.

8. The method of claim 7, wherein said nucleotide sequence SEQ ID NO: 21.

9. The method of claim 7, further comprising isolating said Neu protein.

10. A vector comprising a nucleotide sequence, wherein said nucleotide sequence encodes a Neu polypeptide, wherein said nucleotide sequence is operably associated with a promoter, and where said nucleotide sequence has at least 90% sequence identity to SEQ ID NO: 21.

11. The vector of claim 10, wherein said nucleotide sequence comprises SEQ ID NO: 21.

12. A method of constructing a transformed host cell that expresses a Neu protein, comprising: providing a polynucleotide that comprises a nucleotide sequence encoding a Neu protein, and transforming said host cell with said polynucleotide, wherein said polynucleotide is capable of expressing said encoded Neu protein in said transformed lost cell, and wherein said nucleotide sequence has at least 90% sequence identity to a SEQ ID NO: 21.

13. A purified polynucleotide encoding a Neu polypeptide, wherein said Neu polypeptide comprises at least one neuralized homology repeat domain and a C3HC4 RING-zinc finger domain, and wherein said Neu polypetide has at least 90% sequence identity to SEQ ID NO: 22.

14. The purified polynucleotide of claim 13, wherein said Neu polypeptide comprises SEQ ID NO: 22.

15. The method of claim 12, wherein said nucleotide sequence comprises SEQ ID NO: 21.

* * * * *

UNITED STATES PATENT AND TRADEMARK OFFICE
CERTIFICATE OF CORRECTION

PATENT NO.       : 6,962,985 B2                                          Page 1 of 1
APPLICATION NO.  : 09/808387
DATED            : November 8, 2005
INVENTOR(S)      : Palm et al.

It is certified that error appears in the above-identified patent and that said Letters Patent is hereby corrected as shown below:

Claim 1, Col. 109, line 29, after "polypeptide" add - -, wherein said Neu- -.

Claim 8, Col. 109, line 54, after "sequence" add - -comprises- -.

Claim 10, Col. 110, line 32, change "where" to - -wherein- -.

Claim 12, Col. 110, line 41, change "lost" to - -host- -.

Signed and Sealed this

Twenty-second Day of August, 2006

JON W. DUDAS
*Director of the United States Patent and Trademark Office*

SEQUENCE LISTING

<160> NUMBER OF SEQ ID NOS: 48

<210> SEQ ID NO 1
<211> LENGTH: 1725
<212> TYPE: DNA
<213> ORGANISM: Homo sapien -continued

```
<400> SEQUENCE: 1
atgggtaaca acttctccag tatccctcg ctgccccgag gaaacccgag ccgcgcgccg      60
cggggccacc cccagaacct caaagactct atcgggggcc ccttccccgt cacttctcac    120
cgatgccacc acaagcagaa gcactgtccg gcagtgctgc ccagcggggg gctcccagcc    180
acgccgctgc tcttccaccc gcacaccaag ggctcccaga tcctcatgga cctcagccac    240
aaggctgtca gaggcaggc cagcttctgc aacgccatca ccttcagcaa ccgcccggtc    300
ctcatctacg agcaagtcag gctgaagatc accaagaagc agtgctgctg gagcggggcc    360
ctgcggctgg gcttcaccag caaggacccg tcccgcatcc accctgactc gctgcccaag    420
tacgcctgcc ccgacctggt gtcccagagt ggcttctggg ccaaggcgct gcctgaggag    480
tttgccaatg agggcaacat catcgcattc tgggtggaca gaagggccg tgtcttccac    540
cgcatcaacg actcggctgt tatgctgttc ttcagcgggg tccgcacggc cgacccgctc    600
tgggccctgg tggacgtcta cggcctcacg cggggcgtcc agctgcttga tagcgagctg    660
gtgctcccgg actgtctgcg gccgcgctcc ttcaccgccc tgcggcggcc gtcgctgcgg    720
cgcgaggcgg acgacgcgcg cctctcggtg agcctatgcg acctcaacgt gccgggcgcg    780
gacggcgacg aggccgcgcc ggccgccggc tgccccatcc gcagaactc actcaactcg    840
cagcacagcc gcgcgctgcc ggcgcagctc gacggcgacc tgcgtttcca cgccctgcgc    900
gccggcgcgc acgtccgcat cctcgacgag cagacggtgg cgcgcgtgga gcacgggcgc    960
gacgagcgcg cgctcgtctt caccagccgg cccgtgcgcg tggccgagac catcttcgtc   1020
aaggtcacgc gctcgggtgg cgcgcggccc ggcgcgctgt cgttcggcgt caccacgtgc   1080
gaccccggca cgctgcggcc ggccgacctg cctttcagcc ctgaggccct ggtgaccgc    1140
aaggaattct gggccgtgtg ccgcgtgccc gggcccctgc acagcggcga catcctgggc   1200
ctggtggtca cgccgacgg cgagctgcac ctcagccaca atggcgcggc cgccggcatg   1260
cagctgtgcg tggacgcctc gcagccgctt tggatgctct tcggcctgca cgggaccatc   1320
acgcagatcc gcatcctcgg ctccactatc ctggccgagc ggggtatccc gtcactcccc   1380
tgctcccctg cctccacgcc aacctcgccc agtgccctgg gcagccgcct gtctgacccc   1440
ttgctcagca cgtgcagctc tggccctctg ggtagctctg ctggtgggac agcccccaat   1500
tcgccagtga gcctgcccga gtcgccagtg accccaggtc tgggccagtg gagcgatgag   1560
tgcaccattt gctatgaaca cgcggtggac acggtcatct acacatgtgg ccacatgtgc   1620
ctctgctacg cctgtggcct gcgcctcaag aaggctctgc acgcctgctg ccccatctgc   1680
cgccgcccca tcaaggacat catcaagacc taccgcagct cctag                   1725
```

<210> SEQ ID NO 2
<211> LENGTH: 574
<212> TYPE: PRT
<213> ORGANISM: Homo sapien

<400> SEQUENCE: 2

```
Met Gly Asn Asn Phe Ser Ser Ile Pro Ser Leu Pro Arg Gly Asn Pro
  1               5                  10                  15

Ser Arg Ala Pro Arg Gly His Pro Gln Asn Leu Lys Asp Ser Ile Gly
             20                  25                  30

Gly Pro Phe Pro Val Thr Ser His Arg Cys His His Lys Gln Lys His
         35                  40                  45

Cys Pro Ala Val Leu Pro Ser Gly Gly Leu Pro Ala Thr Pro Leu Leu
     50                  55                  60
```

-continued

```
Phe His Pro His Thr Lys Gly Ser Gln Ile Leu Met Asp Leu Ser His
 65                  70                  75                  80

Lys Ala Val Lys Arg Gln Ala Ser Phe Cys Asn Ala Ile Thr Phe Ser
                 85                  90                  95

Asn Arg Pro Val Leu Ile Tyr Glu Gln Val Arg Leu Lys Ile Thr Lys
            100                 105                 110

Lys Gln Cys Cys Trp Ser Gly Ala Leu Arg Leu Gly Phe Thr Ser Lys
        115                 120                 125

Asp Pro Ser Arg Ile His Pro Asp Ser Leu Pro Lys Tyr Ala Cys Pro
130                 135                 140

Asp Leu Val Ser Gln Ser Gly Phe Trp Ala Lys Ala Leu Pro Glu Glu
145                 150                 155                 160

Phe Ala Asn Glu Gly Asn Ile Ile Ala Phe Trp Val Asp Lys Lys Gly
                165                 170                 175

Arg Val Phe His Arg Ile Asn Asp Ser Ala Val Met Leu Phe Phe Ser
            180                 185                 190

Gly Val Arg Thr Ala Asp Pro Leu Trp Ala Leu Val Asp Val Tyr Gly
        195                 200                 205

Leu Thr Arg Gly Val Gln Leu Leu Asp Ser Glu Leu Val Leu Pro Asp
210                 215                 220

Cys Leu Arg Pro Arg Ser Phe Thr Ala Leu Arg Arg Pro Ser Leu Arg
225                 230                 235                 240

Arg Glu Ala Asp Asp Ala Arg Leu Ser Val Ser Leu Cys Asp Leu Asn
                245                 250                 255

Val Pro Gly Ala Asp Gly Asp Glu Ala Ala Pro Ala Ala Gly Cys Pro
            260                 265                 270

Ile Pro Gln Asn Ser Leu Asn Ser Gln His Ser Arg Ala Leu Pro Ala
        275                 280                 285

Gln Leu Asp Gly Asp Leu Arg Phe His Ala Leu Arg Ala Gly Ala His
290                 295                 300

Val Arg Ile Leu Asp Glu Gln Thr Val Ala Arg Val Glu His Gly Arg
305                 310                 315                 320

Asp Glu Arg Ala Leu Val Phe Thr Ser Arg Pro Val Arg Val Ala Glu
                325                 330                 335

Thr Ile Phe Val Lys Val Thr Arg Ser Gly Ala Arg Pro Gly Ala
            340                 345                 350

Leu Ser Phe Gly Val Thr Thr Cys Asp Pro Gly Thr Leu Arg Pro Ala
        355                 360                 365

Asp Leu Pro Phe Ser Pro Glu Ala Leu Val Asp Arg Lys Glu Phe Trp
370                 375                 380

Ala Val Cys Arg Val Pro Gly Pro Leu His Ser Gly Asp Ile Leu Gly
385                 390                 395                 400

Leu Val Val Asn Ala Asp Gly Glu Leu His Leu Ser His Asn Gly Ala
                405                 410                 415

Ala Ala Gly Met Gln Leu Cys Val Asp Ala Ser Gln Pro Leu Trp Met
            420                 425                 430

Leu Phe Gly Leu His Gly Thr Ile Thr Gln Ile Arg Ile Leu Gly Ser
        435                 440                 445

Thr Ile Leu Ala Glu Arg Gly Ile Pro Ser Leu Pro Cys Ser Pro Ala
450                 455                 460

Ser Thr Pro Thr Ser Pro Ser Ala Leu Gly Ser Arg Leu Ser Asp Pro
465                 470                 475                 480
```

-continued

```
Leu Leu Ser Thr Cys Ser Ser Gly Pro Leu Gly Ser Ser Ala Gly Gly
            485                 490                 495

Thr Ala Pro Asn Ser Pro Val Ser Leu Pro Glu Ser Pro Val Thr Pro
            500                 505                 510

Gly Leu Gly Gln Trp Ser Asp Glu Cys Thr Ile Cys Tyr Glu His Ala
            515                 520                 525

Val Asp Thr Val Ile Tyr Thr Cys Gly His Met Cys Leu Cys Tyr Ala
            530                 535                 540

Cys Gly Leu Arg Leu Lys Lys Ala Leu His Ala Cys Cys Pro Ile Cys
545                 550                 555                 560

Arg Arg Pro Ile Lys Asp Ile Ile Lys Thr Tyr Arg Ser Ser
            565                 570
```

<210> SEQ ID NO 3
<211> LENGTH: 1674
<212> TYPE: DNA
<213> ORGANISM: Homo sapien

<400> SEQUENCE: 3

| | |
|---|---|
| atgggggac agatcacccg gagcactctc cacgactcta tcggggcccc cttcccccgtc | 60 |
| acttctcacc gatgccacca caagcagaag cactgtccgg cagtgctgcc cagcgggggg | 120 |
| ctcccagcca cgccgctgct cttccacccg cacaccaagg ctcccagat cctcatggac | 180 |
| ctcagccaca aggctgtcaa gaggcaggcc agcttctgca acgccatcac cttcagcaac | 240 |
| cgcccggtcc tcatctacga gcaagtcagg ctgaagatca ccaagaagca gtgctgctgg | 300 |
| agcggggccc tgcggctggg cttcaccagc aaggacccgt cccgcatcca ccctgactcg | 360 |
| ctgcccaagt acgcctgccc cgacctggtg tcccagagtg gcttctgggc caaggcgctg | 420 |
| cctgaggagt ttgccaatga gggcaacatc atcgcattct gggtggacaa gaagggccgt | 480 |
| gtcttccacc gcatcaacga ctcggctgtt atgctgttct tcagcggggt ccgcacggcc | 540 |
| gacccgctct gggccctggt ggacgtctac ggcctcacgc ggggcgtcca gctgcttgat | 600 |
| agcgagctgg tgctcccgga ctgtctgcgg ccgcgctcct tcaccgccct gcggcggccg | 660 |
| tcgctgcggc gcgaggcgga cgacgcgcgc ctctcggtga gcctatgcga cctcaacgtg | 720 |
| ccgggcgcgg acggcgacga ggccgcgccg ccgccggct gccccatccc gcagaactca | 780 |
| ctcaactcgc agcacagccg cgcgctgccg gcgcagctcg acggcgacct gcgtttccac | 840 |
| gccctgcgcg ccggcgcgca cgtccgcatc ctcgacgagc agacggtggc gcgcgtggag | 900 |
| cacgggcgcg acgagcgcgc gctcgtcttc accagccggc ccgtgcgcgt ggccgagacc | 960 |
| atcttcgtca aggtcacgcg ctcgggtggc gcgcggcccg gcgcgctgtc gttcggcgtc | 1020 |
| accacgtgcg accccggcac gctgcggccg gccgacctgc ctttcagccc tgaggccctg | 1080 |
| gtggaccgca aggaattctg ggccgtgtgc cgcgtgcccg gcccctgca cagcggcgac | 1140 |
| atcctgggcc tggtggtcaa cgccgacggc gagctgcacc tcagccacaa tggcgcggcc | 1200 |
| gccggcatgc agctgtgcgt ggacgcctcg cagccgcttt ggatgctctt cggcctgcac | 1260 |
| gggaccatca cgcagatccg catcctcggc tccactatcc tggccgagcg gggtatcccg | 1320 |
| tcactcccct gctcccctgc ctccacgcca acctcgccca gtgccctggg cagccgcctg | 1380 |
| tctgaccccct tgctcagcac gtgcagctct ggcctctgg gtagctctgc tggtgggaca | 1440 |
| gcccccaatt cgccagtgag cctgcccgag tcgccagtga ccccaggtct gggccagtgg | 1500 |
| agcgatgagt gcaccatttg ctatgaacac gcggtggaca cggtcatcta cacatgtggc | 1560 |

```
cacatgtgcc tctgctacgc ctgtggcctg cgcctcaaga aggctctgca cgcctgctgc    1620
cccatctgcc gccgccccat caaggacatc atcaagacct accgcagctc ctag          1674
```

<210> SEQ ID NO 4
<211> LENGTH: 557
<212> TYPE: PRT
<213> ORGANISM: Homo sapien

<400> SEQUENCE: 4

```
Met Gly Gly Gln Ile Thr Arg Ser Thr Leu His Asp Ser Ile Gly Gly
 1               5                  10                  15

Pro Phe Pro Val Thr Ser His Arg Cys His His Lys Gln Lys His Cys
             20                  25                  30

Pro Ala Val Leu Pro Ser Gly Gly Leu Pro Ala Thr Pro Leu Leu Phe
         35                  40                  45

His Pro His Thr Lys Gly Ser Gln Ile Leu Met Asp Leu Ser His Lys
     50                  55                  60

Ala Val Lys Arg Gln Ala Ser Phe Cys Asn Ala Ile Thr Phe Ser Asn
 65                  70                  75                  80

Arg Pro Val Leu Ile Tyr Glu Gln Val Arg Leu Lys Ile Thr Lys Lys
                 85                  90                  95

Gln Cys Cys Trp Ser Gly Ala Leu Arg Leu Gly Phe Thr Ser Lys Asp
            100                 105                 110

Pro Ser Arg Ile His Pro Asp Ser Leu Pro Lys Tyr Ala Cys Pro Asp
        115                 120                 125

Leu Val Ser Gln Ser Gly Phe Trp Ala Lys Ala Leu Pro Glu Glu Phe
    130                 135                 140

Ala Asn Glu Gly Asn Ile Ile Ala Phe Trp Val Asp Lys Lys Gly Arg
145                 150                 155                 160

Val Phe His Arg Ile Asn Asp Ser Ala Val Met Leu Phe Phe Ser Gly
                165                 170                 175

Val Arg Thr Ala Asp Pro Leu Trp Ala Leu Val Asp Val Tyr Gly Leu
            180                 185                 190

Thr Arg Gly Val Gln Leu Leu Asp Ser Glu Leu Val Leu Pro Asp Cys
        195                 200                 205

Leu Arg Pro Arg Ser Phe Thr Ala Leu Arg Arg Pro Ser Leu Arg Arg
    210                 215                 220

Glu Ala Asp Asp Ala Arg Leu Ser Val Ser Leu Cys Asp Leu Asn Val
225                 230                 235                 240

Pro Gly Ala Asp Gly Asp Glu Ala Ala Pro Ala Ala Gly Cys Pro Ile
                245                 250                 255

Pro Gln Asn Ser Leu Asn Ser Gln His Ser Arg Ala Leu Pro Ala Gln
            260                 265                 270

Leu Asp Gly Asp Leu Arg Phe His Ala Leu Arg Ala Gly Ala His Val
        275                 280                 285

Arg Ile Leu Asp Glu Gln Thr Val Ala Arg Val Glu His Gly Arg Asp
    290                 295                 300

Glu Arg Ala Leu Val Phe Thr Ser Arg Pro Val Arg Val Ala Glu Thr
305                 310                 315                 320

Ile Phe Val Lys Val Thr Arg Ser Gly Gly Ala Arg Pro Gly Ala Leu
                325                 330                 335

Ser Phe Gly Val Thr Thr Cys Asp Pro Gly Thr Leu Arg Pro Ala Asp
            340                 345                 350
```

-continued

```
Leu Pro Phe Ser Pro Glu Ala Leu Val Asp Arg Lys Glu Phe Trp Ala
            355                 360                 365
Val Cys Arg Val Pro Gly Pro Leu His Ser Gly Asp Ile Leu Gly Leu
        370                 375                 380
Val Val Asn Ala Asp Gly Glu Leu His Leu Ser His Asn Gly Ala Ala
385                 390                 395                 400
Ala Gly Met Gln Leu Cys Val Asp Ala Ser Gln Pro Leu Trp Met Leu
                405                 410                 415
Phe Gly Leu His Gly Thr Ile Thr Gln Ile Arg Ile Leu Gly Ser Thr
            420                 425                 430
Ile Leu Ala Glu Arg Gly Ile Pro Ser Leu Pro Cys Ser Pro Ala Ser
        435                 440                 445
Thr Pro Thr Ser Pro Ser Ala Leu Gly Ser Arg Leu Ser Asp Pro Leu
    450                 455                 460
Leu Ser Thr Cys Ser Ser Gly Pro Leu Gly Ser Ser Ala Gly Gly Thr
465                 470                 475                 480
Ala Pro Asn Ser Pro Val Ser Leu Pro Glu Ser Pro Val Thr Pro Gly
                485                 490                 495
Leu Gly Gln Trp Ser Asp Glu Cys Thr Ile Cys Tyr Glu His Ala Val
            500                 505                 510
Asp Thr Val Ile Tyr Thr Cys Gly His Met Cys Leu Cys Tyr Ala Cys
        515                 520                 525
Gly Leu Arg Leu Lys Lys Ala Leu His Ala Cys Cys Pro Ile Cys Arg
    530                 535                 540
Arg Pro Ile Lys Asp Ile Ile Lys Thr Tyr Arg Ser Ser
545                 550                 555
```

```
<210> SEQ ID NO 5
<211> LENGTH: 1161
<212> TYPE: DNA
<213> ORGANISM: Homo sapien

<400> SEQUENCE: 5
atgggtaaca acttctccag tatccctcg ctgccccgag gaaacccgag ccgcgcgccg      60
cggggccacc cccagaacct caaagatagc gagctggtgc tcccggactg tctgcggccg    120
cgctccttca ccgccctgcg gcggccgtcc ctgcggcgcg aggcggacga cgcgcgcctc    180
tcggtgagcc tatgcgacct caacgtgccg ggcgcggacg cgacgaggc cgcgccggcc     240 gccggctgcc ccatcccgca gaactcactc aactcgcagc acagccgcgc gctgccggcg    300
cagctcgacg gcgacctgcg tttccacgcc ctgcgcgccg cgcgcacgt ccgcatcctc     360 gacgagcaga cggtggcgcg cgtggagcac gggcgcgacg agcgcgcgct cgtcttcacc    420
agccggcccg tgcgcgtggc cgagaccatc ttcgtcaagg tcacgcgctc gggtggcgcg    480
cggcccggcg cgctgtcgtt cggcgtcacc acgtgcgacc ccggcacgct gcggccggcc    540
gacctgcctt tcagccctga ggccctggtg accgcaagg aattctgggc cgtgtgccgc     600
gtgcccgggc ccctgcacag cggcgacatc ctgggcctgg tggtcaacgc cgacggcgag    660
ctgcacctca gccacaatgg cgcggccgcc ggcatgcagc tgtgcgtgga cgcctcgcag    720
ccgctttgga tgctcttcgg cctgcacggg accatcacgc agatccgcat cctcggctcc    780
actatcctgg ccgagcgggg tatcccgtca ctccctgct cccctgcctc cacgccaacc    840
tcgcccagtg ccctgggcag ccgcctgtct gaccccttgc tcagcacgtg cagctctggc    900
cctctgggta gctctgctgg tggacagcc cccaattcgc cagtgagcct gcccgagtcg     960
```

```
ccagtgaccc caggtctggg ccagtggagc gatgagtgca ccatttgcta tgaacacgcg    1020
gtggacacgg tcatctacac atgtggccac atgtgcctct gctacgcctg tggcctgcgc    1080
ctcaagaagg ctctgcacgc ctgctgcccc atctgccgcc gccccatcaa ggacatcatc    1140
aagacctacc gcagctccta g                                              1161
```

<210> SEQ ID NO 6
<211> LENGTH: 386
<212> TYPE: PRT
<213> ORGANISM: Homo sapien

<400> SEQUENCE: 6

```
Met Gly Asn Asn Phe Ser Ser Ile Pro Ser Leu Pro Arg Gly Asn Pro
1               5                   10                  15

Ser Arg Ala Pro Arg Gly His Pro Gln Asn Leu Lys Asp Ser Glu Leu
            20                  25                  30

Val Leu Pro Asp Cys Leu Arg Pro Arg Ser Phe Thr Ala Leu Arg Arg
        35                  40                  45

Pro Ser Leu Arg Arg Glu Ala Asp Ala Arg Leu Ser Val Ser Leu
    50                  55                  60

Cys Asp Leu Asn Val Pro Gly Ala Asp Gly Asp Glu Ala Ala Pro Ala
65                  70                  75                  80

Ala Gly Cys Pro Ile Pro Gln Asn Ser Leu Asn Ser Gln His Ser Arg
                85                  90                  95

Ala Leu Pro Ala Gln Leu Asp Gly Asp Leu Arg Phe His Ala Leu Arg
            100                 105                 110

Ala Gly Ala His Val Arg Ile Leu Asp Glu Gln Thr Val Ala Arg Val
        115                 120                 125

Glu His Gly Arg Asp Glu Arg Ala Leu Val Phe Thr Ser Arg Pro Val
    130                 135                 140

Arg Val Ala Glu Thr Ile Phe Val Lys Val Thr Arg Ser Gly Gly Ala
145                 150                 155                 160

Arg Pro Gly Ala Leu Ser Phe Gly Val Thr Thr Cys Asp Pro Gly Thr
                165                 170                 175

Leu Arg Pro Ala Asp Leu Pro Phe Ser Pro Glu Ala Leu Val Asp Arg
            180                 185                 190

Lys Glu Phe Trp Ala Val Cys Arg Val Pro Gly Pro Leu His Ser Gly
        195                 200                 205

Asp Ile Leu Gly Leu Val Val Asn Ala Asp Gly Glu Leu His Leu Ser
    210                 215                 220

His Asn Gly Ala Ala Ala Gly Met Gln Leu Cys Val Asp Ala Ser Gln
225                 230                 235                 240

Pro Leu Trp Met Leu Phe Gly Leu His Gly Thr Ile Thr Gln Ile Arg
                245                 250                 255

Ile Leu Gly Ser Thr Ile Leu Ala Glu Arg Gly Ile Pro Ser Leu Pro
            260                 265                 270

Cys Ser Pro Ala Ser Thr Pro Thr Ser Pro Ala Leu Gly Ser Arg
        275                 280                 285

Leu Ser Asp Pro Leu Leu Ser Thr Cys Ser Ser Gly Pro Leu Gly Ser
    290                 295                 300

Ser Ala Gly Gly Thr Ala Pro Asn Ser Pro Val Ser Leu Pro Glu Ser
305                 310                 315                 320

Pro Val Thr Pro Gly Leu Gly Gln Trp Ser Asp Glu Cys Thr Ile Cys
                325                 330                 335
```

```
Tyr Glu His Ala Val Asp Thr Val Ile Tyr Thr Cys Gly His Met Cys
                340                 345                 350

Leu Cys Tyr Ala Cys Gly Leu Arg Leu Lys Lys Ala Leu His Ala Cys
            355                 360                 365

Cys Pro Ile Cys Arg Arg Pro Ile Lys Asp Ile Ile Lys Thr Tyr Arg
        370                 375                 380

Ser Ser
385

<210> SEQ ID NO 7
<211> LENGTH: 1749
<212> TYPE: DNA
<213> ORGANISM: mouse

<400> SEQUENCE: 7
```

| | | | | | |
|---|---|---|---|---|---|
| atgggtaaca | acttctccag | tgtctcctct | ctgcagcgag | gaaacccgag | ccgcgcgtcg | 60 |
| cggggccacc | cccagaacct | caaagaatcc | atcgggggct | ccttcccggt | gccctctcac | 120 |
| cgatgccatc | acaagcagaa | gcattgcccg | cctacgctgt | caggtggggg | gctcccggcc | 180 |
| acgccgctgc | tcttccaccc | ccacactaag | ggctcccaga | tcctcatgga | cctcagccac | 240 |
| aaggccgtca | gaggcaggc | cagcttctgc | aatgccatca | ccttcagtaa | ccgcccggtg | 300 |
| ctcatctacg | agcaagtcag | gctgaagatc | accaagaagc | aatgctgctg | agcggggcc | 360 |
| ctgcgacttg | gcttcaccag | caaggaccct | tcccgcatcc | accccgactc | gctgcccaag | 420 |
| tacgcctgcc | ctgacctggt | gtctcagagt | ggcttctggg | ccaaagcatt | gcctgaggag | 480 |
| tttgccaacg | agggcaacat | cattgccttc | tgggtggaca | agaagggccg | cgtcttctac | 540 |
| cggatcaatg | agtcagctgc | tatgcttttc | ttcagtgggg | tccggacggt | ggacccgctc | 600 |
| tgggccctgg | tggacgtcta | cggcctcacg | cggggtgtcc | agctgctaga | cagcgagctg | 660 |
| gtgctgcccg | actgcctgcg | gccgcgctcc | ttcaccgcgc | tgcggcggcc | gtcgctgcgg | 720 |
| tgcgaggcgg | atgaggcgcg | cctgtcggtg | agcctgtgcg | acctcaacgt | gccgggagcc | 780 |
| gacggcgacg | acggcgcacc | gcctgccggc | tgcccgatcc | cgcagaactc | gctcaattct | 840 |
| cagcacagcc | gcgcgctgcc | ggcgcagctc | gacggcgacc | tgcgcttcca | cgcgcttcgc | 900 |
| gccggcgcgc | acgtccgcat | cctggacgag | cagacggtgg | cgcgcctgga | gcacgggcgc | 960 |
| gacgagcgcg | cgctcgtctt | caccagccgg | cctgtgagcg | tggccgagac | catcttcatc | 1020 |
| aaggtcacgc | gctcgggcgg | ggggcgagcg | ggcgcgctgt | ccttcggggt | caccacgtgt | 1080 |
| gaccctggca | cgctgcggcc | cgcggacctg | cccttcagcc | ccgaggccct | ggtggaccgc | 1140 |
| aaggagttct | gggcggtgtg | tcgcgtgccc | gggcctctgc | acagcggcga | catcctgggc | 1200 |
| ctggtggtca | cgcggacgg | agagctgcac | ctgagtcaca | acggcgcggc | ggccggcatg | 1260 |
| cagctgtgcg | tggatgcctc | gcagcccctc | tggatgctct | tcagcctgca | tggcgccatc | 1320 |
| acgcaggtcc | gcatcctcgg | ctccaccatc | atgactgaac | ggggtggccc | atctctcccc | 1380 |
| tgctcacctg | cttccactcc | aacctcaccc | agtgccctgg | gcatccgctt | gtctgacccc | 1440 |
| ttgctcagca | cctgcggttc | tgggccccta | ggtggctctg | ctggagggac | agcccccaat | 1500 |
| tcacctgtga | gcctgcccga | gtcaccggtg | accccaggtc | tgggccagtg | gagtgatgaa | 1560 |
| tgcaccattt | gctatgaaca | cgcagtggat | acagtcatct | acacgtgtgg | ccacatgtgc | 1620 |
| ctgtgctact | cctgtggcct | gcgcctcaag | aaggccctgc | acgcctgctg | cccccatctgc | 1680 |
| cgtcgcccca | tcaaggacat | catcaagacc | taccgcagct | cgtagcccac | tgcagagccc | 1740 |
| cacctgcac | | | | | | 1749 |

-continued

```
<210> SEQ ID NO 8
<211> LENGTH: 574
<212> TYPE: PRT
<213> ORGANISM: mouse

<400> SEQUENCE: 8
```

| | | | | | | | | | | | | | | | |
|---|---|---|---|---|---|---|---|---|---|---|---|---|---|---|---|
| Met | Gly | Asn | Asn | Phe | Ser | Ser | Val | Ser | Ser | Leu | Gln | Arg | Gly | Asn | Pro |
| 1 | | | | 5 | | | | | 10 | | | | | 15 | |
| Ser | Arg | Ala | Ser | Arg | Gly | His | Pro | Gln | Asn | Leu | Lys | Glu | Ser | Ile | Gly |
| | | | 20 | | | | | 25 | | | | | 30 | | |
| Gly | Ser | Phe | Pro | Val | Pro | Ser | His | Arg | Cys | His | His | Lys | Gln | Lys | His |
| | | | 35 | | | | | 40 | | | | | 45 | | |
| Cys | Pro | Pro | Thr | Leu | Ser | Gly | Gly | Leu | Pro | Ala | Thr | Pro | Leu | Leu | |
| 50 | | | | | 55 | | | | | 60 | | | | | |
| Phe | His | Pro | His | Thr | Lys | Gly | Ser | Gln | Ile | Leu | Met | Asp | Leu | Ser | His |
| 65 | | | | | 70 | | | | | 75 | | | | | 80 |
| Lys | Ala | Val | Lys | Arg | Gln | Ala | Ser | Phe | Cys | Asn | Ala | Ile | Thr | Phe | Ser |
| | | | | 85 | | | | | 90 | | | | | 95 | |
| Asn | Arg | Pro | Val | Leu | Ile | Tyr | Glu | Gln | Val | Arg | Leu | Lys | Ile | Thr | Lys |
| | | | | 100 | | | | | 105 | | | | | 110 | |
| Lys | Gln | Cys | Cys | Trp | Ser | Gly | Ala | Leu | Arg | Leu | Gly | Phe | Thr | Ser | Lys |
| | | | | 115 | | | | | 120 | | | | | 125 | |
| Asp | Pro | Ser | Arg | Ile | His | Pro | Asp | Ser | Leu | Pro | Lys | Tyr | Ala | Cys | Pro |
| | 130 | | | | | 135 | | | | | 140 | | | | |
| Asp | Leu | Val | Ser | Gln | Ser | Gly | Phe | Trp | Ala | Lys | Ala | Leu | Pro | Glu | Glu |
| 145 | | | | | 150 | | | | | 155 | | | | | 160 |
| Phe | Ala | Asn | Glu | Gly | Asn | Ile | Ile | Ala | Phe | Trp | Val | Asp | Lys | Lys | Gly |
| | | | | 165 | | | | | 170 | | | | | 175 | |
| Arg | Val | Phe | Tyr | Arg | Ile | Asn | Glu | Ser | Ala | Ala | Met | Leu | Phe | Phe | Ser |
| | | | | 180 | | | | | 185 | | | | | 190 | |
| Gly | Val | Arg | Thr | Val | Asp | Pro | Leu | Trp | Ala | Leu | Val | Asp | Val | Tyr | Gly |
| | | | | 195 | | | | | 200 | | | | | 205 | |
| Leu | Thr | Arg | Gly | Val | Gln | Leu | Leu | Asp | Ser | Glu | Leu | Val | Leu | Pro | Asp |
| | 210 | | | | | 215 | | | | | 220 | | | | |
| Cys | Leu | Arg | Pro | Arg | Ser | Phe | Thr | Ala | Leu | Arg | Arg | Pro | Ser | Leu | Arg |
| 225 | | | | | 230 | | | | | 235 | | | | | 240 |
| Cys | Glu | Ala | Asp | Glu | Ala | Arg | Leu | Ser | Val | Ser | Leu | Cys | Asp | Leu | Asn |
| | | | | 245 | | | | | 250 | | | | | 255 | |
| Val | Pro | Gly | Ala | Asp | Gly | Asp | Gly | Ala | Pro | Pro | Ala | Gly | Cys | Pro | |
| | | | | 260 | | | | | 265 | | | | | 270 | |
| Ile | Pro | Gln | Asn | Ser | Leu | Asn | Ser | Gln | His | Ser | Arg | Ala | Leu | Pro | Ala |
| | | | | 275 | | | | | 280 | | | | | 285 | |
| Gln | Leu | Asp | Gly | Asp | Leu | Arg | Phe | His | Ala | Leu | Arg | Ala | Gly | Ala | His |
| | 290 | | | | | 295 | | | | | 300 | | | | |
| Val | Arg | Ile | Leu | Asp | Glu | Gln | Thr | Val | Ala | Arg | Leu | Glu | His | Gly | Arg |
| 305 | | | | | 310 | | | | | 315 | | | | | 320 |
| Asp | Glu | Arg | Ala | Leu | Val | Phe | Thr | Ser | Arg | Pro | Val | Ser | Val | Ala | Glu |
| | | | | 325 | | | | | 330 | | | | | 335 | |
| Thr | Ile | Phe | Ile | Lys | Val | Thr | Arg | Ser | Gly | Gly | Arg | Ala | Gly | Ala | |
| | | | | 340 | | | | | 345 | | | | | 350 | |
| Leu | Ser | Phe | Gly | Val | Thr | Thr | Cys | Asp | Pro | Gly | Thr | Leu | Arg | Pro | Ala |
| | | | 355 | | | | | 360 | | | | | 365 | | |
| Asp | Leu | Pro | Phe | Ser | Pro | Glu | Ala | Leu | Val | Asp | Arg | Lys | Glu | Phe | Trp |
| | 370 | | | | | 375 | | | | | 380 | | | | |

```
Ala Val Cys Arg Val Pro Gly Pro Leu His Ser Gly Asp Ile Leu Gly
385                 390                 395                 400

Leu Val Val Asn Ala Asp Gly Glu Leu His Leu Ser His Asn Gly Ala
            405                 410                 415

Ala Ala Gly Met Gln Leu Cys Val Asp Ala Ser Gln Pro Leu Trp Met
        420                 425                 430

Leu Phe Ser Leu His Gly Ala Ile Thr Gln Val Arg Ile Leu Gly Ser
            435                 440                 445

Thr Ile Met Thr Glu Arg Gly Gly Pro Ser Leu Pro Cys Ser Pro Ala
        450                 455                 460

Ser Thr Pro Thr Ser Pro Ser Ala Leu Gly Ile Arg Leu Ser Asp Pro
465                 470                 475                 480

Leu Leu Ser Thr Cys Gly Ser Gly Pro Leu Gly Gly Ser Ala Gly Gly
            485                 490                 495

Thr Ala Pro Asn Ser Pro Val Ser Leu Pro Glu Ser Pro Val Thr Pro
            500                 505                 510

Gly Leu Gly Gln Trp Ser Asp Glu Cys Thr Ile Cys Tyr Glu His Ala
        515                 520                 525

Val Asp Thr Val Ile Tyr Thr Cys Gly His Met Cys Leu Cys Tyr Ser
    530                 535                 540

Cys Gly Leu Arg Leu Lys Lys Ala Leu His Ala Cys Cys Pro Ile Cys
545                 550                 555                 560

Arg Arg Pro Ile Lys Asp Ile Ile Lys Thr Tyr Arg Ser Ser
                565                 570

<210> SEQ ID NO 9
<211> LENGTH: 1698
<212> TYPE: DNA
<213> ORGANISM: mouse

<400> SEQUENCE: 9 atgggggac agatcacaag gaacactatc cacgactcca tcggggctc cttcccggtg      60 ccctctcacc gatgccatca caagcagaag cattgcccgc ctacgctgtc aggtgggggg    120
ctcccggcca cgccgctgct cttccacccc cacactaagg gctcccagat cctcatggac    180
ctcagccaca aggccgtcaa gaggcaggcc agcttctgca atgccatcac cttcagtaac    240
cgcccggtgc tcatctacga gcaagtcagg ctgaagatca ccaagaagca atgctgctgg    300 agcgggccc tgcgacttgg cttcaccagc aaggacccu ccgcatcca ccccgactcg       360 ctgcccaagt acgcctgccc tgacctggtg tctcagagtg gcttctgggc aaagcattg    420 cctgaggagt ttgccaacga gggcaacatc attgccttct gggtggacaa gaagggccgc   480
gtcttctacc ggatcaatga gtcagctgct atgcttttct tcagtgggt ccggacggtg    540 gacccgctct gggccctggt ggacgtctac ggcctcacgc ggggtgtcca gctgctagac   600
agcgagctgg tgctgcccga ctgcctgcgg ccgcgctcct tcaccgcgct gcggcggccg   660
tcgctgcggt gcgaggcgga tgaggcgcgc ctgtcggtga gcctgtgcga cctcaacgtg   720
ccgggagccg acggcgacga cggcgcaccg cctgccggct gcccgatccc gcagaactcg   780
ctcaattctc agcacagccg cgcgctgccg gcgcagctcg acggcgacct gcgcttccac   840
gcgcttcgcg ccggcgcgca cgtccgcatc ctggacgagc agacggtggc gcgcctggag   900
cacgggcgcg acgagcgcgc gctcgtcttc accagccggc ctgtgagcgt ggccgagacc   960
atcttcatca aggtcacgcg ctcgggcggg gggcgagcgg gcgcgctgtc cttcggggtc  1020
accacgtgtg accctggcac gctgcggccc gcggacctgc ccttcagccc cgaggccctg  1080
```

-continued

```
gtggaccgca aggagttctg ggcggtgtgt cgcgtgcccg ggcctctgca cagcggcgac      1140
atcctgggcc tggtggtcaa cgcggacgga gagctgcacc tgagtcacaa cggcgcggcg      1200
gccggcatgc agctgtgcgt ggatgcctcg cagcccctct ggatgctctt cagcctgcat      1260
ggcgccatca cgcaggtccg catcctcggc tccaccatca tgactgaacg gggtggccca      1320
tctctcccct gctcacctgc ttccactcca acctcaccca gtgccctggg catccgcttg      1380
tctgacccct tgctcagcac ctgcggttct gggccctag gtggctctgc tggagggaca       1440
gcccccaatt cacctgtgag cctgcccgag tcaccggtga ccccaggtct gggccagtgg      1500
agtgatgaat gcaccatttg ctatgaacac gcagtggata cagtcatcta cgtgtggc       1560
cacatgtgcc tgtgctactc ctgtggcctg cgcctcaaga aggccctgca cgcctgctgc      1620
cccatctgcc gtcgccccat caaggacatc atcaagacct accgcagctc gtagcccact      1680
gcagagcccc acctgcac                                                   1698
```

<210> SEQ ID NO 10
<211> LENGTH: 557
<212> TYPE: PRT
<213> ORGANISM: mouse

<400> SEQUENCE: 10

```
Met Gly Gly Gln Ile Thr Arg Asn Thr Ile His Asp Ser Ile Gly Gly
 1               5                  10                  15
Ser Phe Pro Val Pro Ser His Arg Cys His His Lys Gln Lys His Cys
                20                  25                  30
Pro Pro Thr Leu Ser Gly Gly Leu Pro Ala Thr Pro Leu Leu Phe
            35                  40                  45
His Pro His Thr Lys Gly Ser Gln Ile Leu Met Asp Leu Ser His Lys
    50                  55                  60
Ala Val Lys Arg Gln Ala Ser Phe Cys Asn Ala Ile Thr Phe Ser Asn
65                  70                  75                  80
Arg Pro Val Leu Ile Tyr Glu Gln Val Arg Leu Lys Ile Thr Lys Lys
                85                  90                  95
Gln Cys Cys Trp Ser Gly Ala Leu Arg Leu Gly Phe Thr Ser Lys Asp
            100                 105                 110
Pro Ser Arg Ile His Pro Asp Ser Leu Pro Lys Tyr Ala Cys Pro Asp
        115                 120                 125
Leu Val Ser Gln Ser Gly Phe Trp Ala Lys Ala Leu Pro Glu Glu Phe
    130                 135                 140
Ala Asn Glu Gly Asn Ile Ile Ala Phe Trp Val Asp Lys Lys Gly Arg
145                 150                 155                 160
Val Phe Tyr Arg Ile Asn Glu Ser Ala Ala Met Leu Phe Phe Ser Gly
                165                 170                 175
Val Arg Thr Val Asp Pro Leu Trp Ala Leu Val Asp Val Tyr Gly Leu
            180                 185                 190
Thr Arg Gly Val Gln Leu Leu Asp Ser Glu Leu Val Leu Pro Asp Cys
        195                 200                 205
Leu Arg Pro Arg Ser Phe Thr Ala Leu Arg Arg Pro Ser Leu Arg Cys
    210                 215                 220
Glu Ala Asp Glu Ala Arg Leu Ser Val Ser Leu Cys Asp Leu Asn Val
225                 230                 235                 240
Pro Gly Ala Asp Gly Asp Gly Ala Pro Ala Gly Cys Pro Ile
                245                 250                 255
```

-continued

```
Pro Gln Asn Ser Leu Asn Ser Gln His Ser Arg Ala Leu Pro Ala Gln
            260                 265                 270

Leu Asp Gly Asp Leu Arg Phe His Ala Leu Arg Ala Gly Ala His Val
        275                 280                 285

Arg Ile Leu Asp Glu Gln Thr Val Ala Arg Leu Glu His Gly Arg Asp
    290                 295                 300

Glu Arg Ala Leu Val Phe Thr Ser Arg Pro Val Ser Val Ala Glu Thr
305                 310                 315                 320

Ile Phe Ile Lys Val Thr Arg Ser Gly Gly Arg Ala Gly Ala Leu
                325                 330                 335

Ser Phe Gly Val Thr Thr Cys Asp Pro Gly Thr Leu Arg Pro Ala Asp
            340                 345                 350

Leu Pro Phe Ser Pro Glu Ala Leu Val Asp Arg Lys Glu Phe Trp Ala
        355                 360                 365

Val Cys Arg Val Pro Gly Pro Leu His Ser Gly Asp Ile Leu Gly Leu
    370                 375                 380

Val Val Asn Ala Asp Gly Glu Leu His Leu Ser His Asn Gly Ala Ala
385                 390                 395                 400

Ala Gly Met Gln Leu Cys Val Asp Ala Ser Gln Pro Leu Trp Met Leu
                405                 410                 415

Phe Ser Leu His Gly Ala Ile Thr Gln Val Arg Ile Leu Gly Ser Thr
            420                 425                 430

Ile Met Thr Glu Arg Gly Gly Pro Ser Leu Pro Cys Ser Pro Ala Ser
        435                 440                 445

Thr Pro Thr Ser Pro Ser Ala Leu Gly Ile Arg Leu Ser Asp Pro Leu
    450                 455                 460

Leu Ser Thr Cys Gly Ser Gly Pro Leu Gly Gly Ser Ala Gly Gly Thr
465                 470                 475                 480

Ala Pro Asn Ser Pro Val Ser Leu Pro Glu Ser Pro Val Thr Pro Gly
                485                 490                 495

Leu Gly Gln Trp Ser Asp Glu Cys Thr Ile Cys Tyr Glu His Ala Val
            500                 505                 510

Asp Thr Val Ile Tyr Thr Cys Gly His Met Cys Leu Cys Tyr Ser Cys
        515                 520                 525

Gly Leu Arg Leu Lys Lys Ala Leu His Ala Cys Cys Pro Ile Cys Arg
    530                 535                 540

Arg Pro Ile Lys Asp Ile Ile Lys Thr Tyr Arg Ser Ser
545                 550                 555
```

<210> SEQ ID NO 11
<211> LENGTH: 1035
<212> TYPE: DNA
<213> ORGANISM: mouse

<400> SEQUENCE: 11

```
atgggtaaca acttctccag tgtctcctct ctgcagcgag gaaacccgag ccgcgcgtcg    60
cggggccacc cccagaacct caagaatcc atcgggggct ccttcccggt gccctctcac   120
cgatgccatc acaagcagaa gcattgcccg cctacgctgt caggtggggg gctcccggcc   180
acgccgctgc tcttccaccc ccacactaag ggctcccaga tcctcatgga cctcagccac   240
aaggccgtca agaggcaggc cagcttctgc aatgccatca ccttcagtaa ccgcccggtg   300
ctcatctacg agcaagtcag gctgaagatc accaagaagc aatgctgctg gagcggggcc   360
ctgcgacttg gcttcaccag caaggaccct tcccgcatcc accccgactc gctgcccaag   420
```

-continued

```
tacgcctgcc ctgacctggt gtctcagagt ggcttctggg ccaaagcatt gcctgaggag    480
tttgccaacg agggcaacat cattgccttc tgggtggaca agaagggccg cgtcttctac    540
cggatcaatg agtcagctgc tatgcttttc ttcagtgggg tccggacggt ggacccgctc    600
tgggccctgg tggacgtcta cggcctcacg cggggtgtcc agctgctagg ctccaccatc    660
atgactgaac gggtggccc atctctcccc tgctcacctg cttccactcc aacctcaccc    720
agtgccctgg gcatccgctt gtctgacccc ttgctcagca cctgcggttc tgggccccta    780
ggtggctctg ctggagggac agccccaat tcacctgtga gcctgcccga gtcaccggtg    840
accccaggtc tgggccagtg gagtgatgaa tgcaccattt gctatgaaca cgcagtggat    900
acagtcatct acacgtgtgg ccacatgtgc ctgtgctact cctgtggcct gcgcctcaag    960
aaggccctgc acgcctgctg ccccatctgc cgtcgcccca tcaaggacat catcaagacc   1020
taccgcagct cgtag                                                    1035
```

<210> SEQ ID NO 12
<211> LENGTH: 344
<212> TYPE: PRT
<213> ORGANISM: mouse

<400> SEQUENCE: 12

```
Met Gly Asn Asn Phe Ser Ser Val Ser Leu Gln Arg Gly Asn Pro
 1               5                  10                  15

Ser Arg Ala Ser Arg Gly His Pro Gln Asn Leu Lys Glu Ser Ile Gly
            20                  25                  30

Gly Ser Phe Pro Val Pro Ser His Arg Cys His His Lys Gln Lys His
        35                  40                  45

Cys Pro Pro Thr Leu Ser Gly Gly Leu Pro Ala Thr Pro Leu Leu
    50                  55                  60

Phe His Pro His Thr Lys Gly Ser Gln Ile Leu Met Asp Leu Ser His
65                  70                  75                  80

Lys Ala Val Lys Arg Gln Ala Ser Phe Cys Asn Ala Ile Thr Phe Ser
                85                  90                  95

Asn Arg Pro Val Leu Ile Tyr Glu Gln Val Arg Leu Lys Ile Thr Lys
            100                 105                 110

Lys Gln Cys Cys Trp Ser Gly Ala Leu Arg Leu Gly Phe Thr Ser Lys
        115                 120                 125

Asp Pro Ser Arg Ile His Pro Asp Ser Leu Pro Lys Tyr Ala Cys Pro
    130                 135                 140

Asp Leu Val Ser Gln Ser Gly Phe Trp Ala Lys Ala Leu Pro Glu Glu
145                 150                 155                 160

Phe Ala Asn Glu Gly Asn Ile Ile Ala Phe Trp Val Asp Lys Lys Gly
                165                 170                 175

Arg Val Phe Tyr Arg Ile Asn Glu Ser Ala Ala Met Leu Phe Phe Ser
            180                 185                 190

Gly Val Arg Thr Val Asp Pro Leu Trp Ala Leu Val Asp Val Tyr Gly
        195                 200                 205

Leu Thr Arg Gly Val Gln Leu Leu Gly Ser Thr Ile Met Thr Glu Arg
    210                 215                 220

Gly Gly Pro Ser Leu Pro Cys Ser Pro Ala Ser Thr Pro Thr Ser Pro
225                 230                 235                 240

Ser Ala Leu Gly Ile Arg Leu Ser Asp Pro Leu Leu Ser Thr Cys Gly
                245                 250                 255
```

-continued

```
Ser Gly Pro Leu Gly Gly Ser Ala Gly Thr Ala Pro Asn Ser Pro
            260                 265                 270

Val Ser Leu Pro Glu Ser Pro Val Thr Pro Gly Leu Gly Gln Trp Ser
        275                 280                 285

Asp Glu Cys Thr Ile Cys Tyr Glu His Ala Val Asp Thr Val Ile Tyr
    290                 295                 300

Thr Cys Gly His Met Cys Leu Cys Tyr Ser Cys Gly Leu Arg Leu Lys
305                 310                 315                 320

Lys Ala Leu His Ala Cys Cys Pro Ile Cys Arg Arg Pro Ile Lys Asp
                325                 330                 335

Ile Ile Lys Thr Tyr Arg Ser Ser
            340
```

<210> SEQ ID NO 13
<211> LENGTH: 876
<212> TYPE: DNA
<213> ORGANISM: mouse

<400> SEQUENCE: 13

```
atgggtaaca acttctccag tgtctcctct ctgcagcgag gaaacccgag ccgcgcgtcg     60
cggggccacc cccagaacct caaagaatcc atcgggggct ccttcccggt gccctctcac    120
cgatgccatc acaagcagaa gcattgcccg cctacgctgt caggtggggg gctcccggcc    180
acgccgctgc tcttccaccc ccacactaag ggctcccaga tcctcatgga cctcagccac    240
aaggccgtca gaggcaggc cagcttctgc aatgccatca ccttcagtaa ccgcccggtg    300
ctcatctacg agcaagtcag gctgaagatc accaagaagc aatgctgctg gagcggggcc    360
ctgcgacttg gcttcaccag caaggaccct ccccgcatcc accccgactc gctgcccaag    420
tacgcctgcc ctgacctggt gtctcagagt ggcttctggg ccaaagcatt gcctgaggag    480
tttgccaacg agggcaacat cattgccttc tgggtggaca gaagggccg cgtcttctac    540
cggatcaatg agtcagctgc tatgcttttc ttcagtgggg tccggacggt ggaccccgctc    600
tgggccctgg tggacgtcta cggcctcacg cggggtgtcc agctgctaga cagcgagctg    660
gtgctgcccg agtcaccggt gaccccaggt ctgggccagt ggagtgatga atgcaccatt    720
tgctatgaac acgcagtgga tacagtcatc tacacgtgtg ccacatgtg cctgtgctac    780
tcctgtggcc tgcgcctcaa gaaggccctg cacgcctgct gccccatctg ccgtcgcccc    840
atcaaggaca tcatcaagac ctaccgcagc tcgtag                              876
```

<210> SEQ ID NO 14
<211> LENGTH: 291
<212> TYPE: PRT
<213> ORGANISM: mouse

<400> SEQUENCE: 14

```
Met Gly Asn Asn Phe Ser Ser Val Ser Ser Leu Gln Arg Gly Asn Pro
1               5                   10                  15

Ser Arg Ala Ser Arg Gly His Pro Gln Asn Leu Lys Glu Ser Ile Gly
            20                  25                  30

Gly Ser Phe Pro Val Pro Ser His Arg Cys His His Lys Gln Lys His
        35                  40                  45

Cys Pro Pro Thr Leu Ser Gly Gly Leu Pro Ala Thr Pro Leu Leu
    50                  55                  60

Phe His Pro His Thr Lys Gly Ser Gln Ile Leu Met Asp Leu Ser His
65                  70                  75                  80
```

```
                Lys Ala Val Lys Arg Gln Ala Ser Phe Cys Asn Ala Ile Thr Phe Ser
                                 85                  90                  95

Asn Arg Pro Val Leu Ile Tyr Glu Gln Val Arg Leu Lys Ile Thr Lys
                            100                 105                 110

Lys Gln Cys Cys Trp Ser Gly Ala Leu Arg Leu Gly Phe Thr Ser Lys
                        115                 120                 125

Asp Pro Ser Arg Ile His Pro Asp Ser Leu Pro Lys Tyr Ala Cys Pro
                    130                 135                 140

Asp Leu Val Ser Gln Ser Gly Phe Trp Ala Lys Ala Leu Pro Glu Glu
                145                 150                 155                 160

Phe Ala Asn Glu Gly Asn Ile Ile Ala Phe Trp Val Asp Lys Lys Gly
                                165                 170                 175

Arg Val Phe Tyr Arg Ile Asn Glu Ser Ala Ala Met Leu Phe Phe Ser
                            180                 185                 190

Gly Val Arg Thr Val Asp Pro Leu Trp Ala Leu Val Asp Val Tyr Gly
                        195                 200                 205

Leu Thr Arg Gly Val Gln Leu Leu Asp Ser Glu Leu Val Leu Pro Glu
                    210                 215                 220

Ser Pro Val Thr Pro Gly Leu Gly Gln Trp Ser Asp Glu Cys Thr Ile
                225                 230                 235                 240

Cys Tyr Glu His Ala Val Asp Thr Val Ile Tyr Thr Cys Gly His Met
                                245                 250                 255

Cys Leu Cys Tyr Ser Cys Gly Leu Arg Leu Lys Lys Ala Leu His Ala
                            260                 265                 270

Cys Cys Pro Ile Cys Arg Arg Pro Ile Lys Asp Ile Ile Lys Thr Tyr
                        275                 280                 285

Arg Ser Ser
                    290

<210> SEQ ID NO 15
<211> LENGTH: 1725
<212> TYPE: DNA
<213> ORGANISM: rat

<400> SEQUENCE: 15
atgggtaaca acttctccag tgtctcctct ctgcagcgag gaaaccccag ccgtgcgtcg    60
cggggccacc cccagaacct caaagactcc atcgggagct ccttcccggt ccctctcac   120 cgatgccatc acaagcagaa gcattgcccg cccgcgctgt caggtggggg gctcccggcc   180
acaccgctgc tcttccaccc ccacactaag ggctcccaga tcctcatgga cctcagccac   240
aaggccgtca gaggcaggc cagcttctgt aatgccatca ccttcagcaa ccgcccgtc    300 ctcatctacg agcaagtcag gctgaagatc accaagaagc agtgctgctg gagcgggcc   360 ctgcgacttg gcttcaccag caaggaccct tcccgcatcc accccgactc actgcccaag   420
tacgcctgcc ctgacctggt gtcccagagt ggcttctggg ccaaagcgtt gcctgaggag   480
tttgccaacg agggcaacat cattgccttc tgggtggaca agaagggccg agtcttctac   540
cggatcaatg agtcggctgc catgctgttc ttcagcgggg ttcgaacggc ggacccgctc   600
tgggccctgg tggacgtcta tggcctcaca cggggtgtcc agctgctaga cagcgagctg   660
gtgctgcctg actgcctgag gccgcgctcc ttcaccgcgc tgcggcggcc gtcgctgcgg   720
tgcgaggcgg acgaggcgcg cctgtctgtg agcctgtgcg acctcaacgt gccgggagcc   780
gacggcgagg acggcgcacc gcccgccggc tgcccgatcc cgcagaactc gctcaactct   840
cagcacagcc gcgcgctgcc ggcgcagctc gacggcgacc tgcgcttcca cgtcctgcgc   900
```

```
gcccgcgcgc aagtccgcat cctggacgag cagacggtgg cgcgcctaga gcacgggcgc      960
gacgagcgcg cgctcgtctt caccagccgg ccggtgcgcg tggccgaaac catcttcatc     1020
aaggtcacgc gctcaggcgg tgcgcgacca gaagcgctgt ccttcggggt caccacgtgt     1080
gaccctggca cgctgcggcc cgccgacctg cccttcagcc ccgaggccct ggtggaccgc     1140
aaggagttct gggcggtgtg tcgcgtgcct gggcctctgc acagtggtga catcctgggc     1200
ctggtggtca atgcggacgg aaagctgcac ctaattcaca acggcgcgcc ggccggcatg     1260
cagctatgcg tggacgcctc gcagcccctc tggatgctct tcagcctgca cggcgccatc     1320
acgcaggtcc gcatccttgg ctccaccatc atggctgaac ggggtggccc atctctcccc     1380
tgctcacctg cctccactcc aacctcgccc agtgccctgg gcagccgcct ctctgacccc     1440
ctgctcagca catgcggttc tgggcccctg ggtggctctg ttggcggaac agcccccaac     1500
tcacctgtga gcctgcccga gtcaccagtg accccgggtc tgggccagtg gagcgatgaa     1560
tgcaccattt gctatgaaca cgcagtggat acagtcatct acacgtgtgg ccacatgtgc     1620
ctgtgctact cctgtggcct gcgcctcaag aaggccctgc acgcctgctg ccccatctgc     1680
cgtcgcccca tcaaggacat catcaagacc taccgcagct cctag                    1725
```

<210> SEQ ID NO 16
<211> LENGTH: 574
<212> TYPE: PRT
<213> ORGANISM: rat

<400> SEQUENCE: 16

```
Met Gly Asn Asn Phe Ser Ser Val Ser Ser Leu Gln Arg Gly Asn Pro
 1               5                  10                  15

Ser Arg Ala Ser Arg Gly His Pro Gln Asn Leu Lys Asp Ser Ile Gly
            20                  25                  30

Ser Ser Phe Pro Val Pro Ser His Arg Cys His His Lys Gln Lys His
        35                  40                  45

Cys Pro Pro Ala Leu Ser Gly Gly Leu Pro Ala Thr Pro Leu Leu
    50                  55                  60

Phe His Pro His Thr Lys Gly Ser Gln Ile Leu Met Asp Leu Ser His
65                  70                  75                  80

Lys Ala Val Lys Arg Gln Ala Ser Phe Cys Asn Ala Ile Thr Phe Ser
                85                  90                  95

Asn Arg Pro Val Leu Ile Tyr Glu Gln Val Arg Leu Lys Ile Thr Lys
            100                 105                 110

Lys Gln Cys Cys Trp Ser Gly Ala Leu Arg Leu Gly Phe Thr Ser Lys
        115                 120                 125

Asp Pro Ser Arg Ile His Pro Asp Ser Leu Pro Lys Tyr Ala Cys Pro
    130                 135                 140

Asp Leu Val Ser Gln Ser Gly Phe Trp Ala Lys Ala Leu Pro Glu Glu
145                 150                 155                 160

Phe Ala Asn Glu Gly Asn Ile Ile Ala Phe Trp Val Asp Lys Lys Gly
                165                 170                 175

Arg Val Phe Tyr Arg Ile Asn Glu Ser Ala Ala Met Leu Phe Phe Ser
            180                 185                 190

Gly Val Arg Thr Ala Asp Pro Leu Trp Ala Leu Val Asp Val Tyr Gly
        195                 200                 205

Leu Thr Arg Gly Val Gln Leu Leu Asp Ser Glu Leu Val Leu Pro Asp
    210                 215                 220
```

| | | | | | | | | | | | |
|---|---|---|---|---|---|---|---|---|---|---|---|
|Cys|Leu|Arg|Pro|Arg|Ser|Phe|Thr|Ala|Leu|Arg|Arg|Pro|Ser|Leu|Arg|
|225| | | |230| | | |235| | | |240| | | |

Cys Leu Arg Pro Arg Ser Phe Thr Ala Leu Arg Arg Pro Ser Leu Arg
225                 230                 235                 240

Cys Glu Ala Asp Glu Ala Arg Leu Ser Val Ser Leu Cys Asp Leu Asn
                245                 250                 255

Val Pro Gly Ala Asp Gly Glu Asp Gly Ala Pro Pro Ala Gly Cys Pro
            260                 265                 270

Ile Pro Gln Asn Ser Leu Asn Ser Gln His Ser Arg Ala Leu Pro Ala
        275                 280                 285

Gln Leu Asp Gly Asp Leu Arg Phe His Ala Leu Arg Ala Arg Ala Gln
    290                 295                 300

Val Arg Ile Leu Asp Glu Gln Thr Val Ala Arg Leu Glu His Gly Arg
305                 310                 315                 320

Asp Glu Arg Ala Leu Val Phe Thr Ser Arg Pro Val Arg Val Ala Glu
                325                 330                 335

Thr Ile Phe Ile Lys Val Thr Arg Ser Gly Ala Arg Pro Glu Ala
            340                 345                 350

Leu Ser Phe Gly Val Thr Thr Cys Asp Pro Gly Thr Leu Arg Pro Ala
        355                 360                 365

Asp Leu Pro Phe Ser Pro Glu Ala Leu Val Asp Arg Lys Glu Phe Trp
    370                 375                 380

Ala Val Cys Arg Val Pro Gly Pro Leu His Ser Gly Asp Ile Leu Gly
385                 390                 395                 400

Leu Val Val Asn Ala Asp Gly Lys Leu His Leu Ile His Asn Gly Ala
                405                 410                 415

Pro Ala Gly Met Gln Leu Cys Val Asp Ala Ser Gln Pro Leu Trp Met
            420                 425                 430

Leu Phe Ser Leu His Gly Ala Ile Thr Gln Val Arg Ile Leu Gly Ser
        435                 440                 445

Thr Ile Met Ala Glu Arg Gly Gly Pro Ser Leu Pro Cys Ser Pro Ala
    450                 455                 460

Ser Thr Pro Thr Ser Pro Ser Ala Leu Gly Ser Arg Leu Ser Asp Pro
465                 470                 475                 480

Leu Leu Ser Thr Cys Gly Ser Gly Pro Leu Gly Gly Ser Val Gly Gly
                485                 490                 495

Thr Ala Pro Asn Ser Pro Val Ser Leu Pro Glu Ser Pro Val Thr Pro
            500                 505                 510

Gly Leu Gly Gln Trp Ser Asp Glu Cys Thr Ile Cys Tyr Glu His Ala
        515                 520                 525

Val Asp Thr Val Ile Tyr Thr Cys Gly His Met Cys Leu Cys Tyr Ser
    530                 535                 540

Cys Gly Leu Arg Leu Lys Lys Ala Leu His Ala Cys Cys Pro Ile Cys
545                 550                 555                 560

Arg Arg Pro Ile Lys Asp Ile Ile Lys Thr Tyr Arg Ser Ser
                565                 570

<210> SEQ ID NO 17
<211> LENGTH: 1035
<212> TYPE: DNA
<213> ORGANISM: rat

<400> SEQUENCE: 17
atgggtaaca acttctccag tgtctcctct ctgcagcgag gaaacccag ccgtgcgtcg    60 cggggccacc cccagaacct caaagactcc atcgggagct ccttcccggt cccctctcac   120
cgatgccatc acaagcagaa gcattgcccg ccgcgctgt caggtggggg gctcccggcc   180

-continued

```
acaccgctgc tcttccaccc ccacactaag ggctcccaga tcctcatgga cctcagccac    240
aaggccgtca agaggcaggc cagcttctgt aatgccatca ccttcagcaa ccgcccgtc     300 ctcatctacg agcaagtcag gctgaagatc accaagaagc agtgctgctg gagcggggcc    360
ctgcgacttg gcttcaccag caaggaccct tcccgcatcc accccgactc actgcccaag    420
tacgcctgcc ctgacctggt gtcccagagt ggcttctggg ccaaagcgtt gcctgaggag    480
tttgccaacg agggcaacat cattgccttc tgggtggaca agaagggccg agtcttctac    540
cggatcaatg agtcggctgc catgctgttc ttcagcgggg ttcgaacggc ggacccgctc    600
tgggccctgg tggacgtcta tggcctcaca cggggtgtcc agctgctagg ctccaccatc    660
atggctgaac ggggtggccc atctctcccc tgctcacctg cctccactcc aacctcgccc    720
agtgccctgg gcagccgcct ctctgacccc ctgctcagca catgcggttc tgggcccctg    780
ggtggctctg ttggcggaac agcccccaac tcacctgtga gcctgcccga gtcaccagtg    840
accccgggtc tgggccagtg gagcgatgaa tgcaccattt gctatgaaca cgcagtggat    900
acagtcatct acacgtgtgg ccacatgtgc ctgtgctact cctgtggcct gcgcctcaag    960
aaggccctgc acgcctgctg ccccatctgc cgtcgcccca tcaaggacat catcaagacc   1020
taccgcagct cctag                                                    1035
```

<210> SEQ ID NO 18
<211> LENGTH: 344
<212> TYPE: PRT
<213> ORGANISM: rat

<400> SEQUENCE: 18

```
Met Gly Asn Asn Phe Ser Ser Val Ser Ser Leu Gln Arg Gly Asn Pro
 1               5                  10                  15

Ser Arg Ala Ser Arg Gly His Pro Gln Asn Leu Lys Asp Ser Ile Gly
             20                  25                  30

Ser Ser Phe Pro Val Pro Ser His Arg Cys His His Lys Gln Lys His
         35                  40                  45

Cys Pro Pro Ala Leu Ser Gly Gly Leu Pro Ala Thr Pro Leu Leu
     50                  55                  60

Phe His Pro His Thr Lys Gly Ser Gln Ile Leu Met Asp Leu Ser His
 65                  70                  75                  80

Lys Ala Val Lys Arg Gln Ala Ser Phe Cys Asn Ala Ile Thr Phe Ser
                 85                  90                  95

Asn Arg Pro Val Leu Ile Tyr Glu Gln Val Arg Leu Lys Ile Thr Lys
            100                 105                 110

Lys Gln Cys Cys Trp Ser Gly Ala Leu Arg Leu Gly Phe Thr Ser Lys
        115                 120                 125

Asp Pro Ser Arg Ile His Pro Asp Ser Leu Pro Lys Tyr Ala Cys Pro
    130                 135                 140

Asp Leu Val Ser Gln Ser Gly Phe Trp Ala Lys Ala Leu Pro Glu Glu
145                 150                 155                 160

Phe Ala Asn Glu Gly Asn Ile Ile Ala Phe Trp Val Asp Lys Lys Gly
                165                 170                 175

Arg Val Phe Tyr Arg Ile Asn Glu Ser Ala Ala Met Leu Phe Phe Ser
            180                 185                 190

Gly Val Arg Thr Ala Asp Pro Leu Trp Ala Leu Val Asp Val Tyr Gly
        195                 200                 205

Leu Thr Arg Gly Val Gln Leu Leu Gly Ser Thr Ile Met Ala Glu Arg
    210                 215                 220
```

```
Gly Gly Pro Ser Leu Pro Cys Ser Pro Ala Ser Thr Pro Thr Ser Pro
225                 230                 235                 240

Ser Ala Leu Gly Ser Arg Leu Ser Asp Pro Leu Ser Thr Cys Gly
            245                 250                 255

Ser Gly Pro Leu Gly Gly Ser Val Gly Gly Thr Ala Pro Asn Ser Pro
                260                 265                 270

Val Ser Leu Pro Glu Ser Pro Val Thr Pro Gly Leu Gly Gln Trp Ser
        275                 280                 285

Asp Glu Cys Thr Ile Cys Tyr Glu His Ala Val Asp Thr Val Ile Tyr
        290                 295                 300

Thr Cys Gly His Met Cys Leu Cys Tyr Ser Cys Gly Leu Arg Leu Lys
305                 310                 315                 320

Lys Ala Leu His Ala Cys Cys Pro Ile Cys Arg Arg Pro Ile Lys Asp
                325                 330                 335

Ile Ile Lys Thr Tyr Arg Ser Ser
            340
```

<210> SEQ ID NO 19
<211> LENGTH: 888
<212> TYPE: DNA
<213> ORGANISM: rat

<400> SEQUENCE: 19

```
atgggtaaca acttctccag tgtctcctct ctgcagcgag␣gaaacccag ccgtgcgtcg      60
cggggccacc cccagaacct caaagactcc atcgggagct cc ttcccggt ccc ctctcac   120
cgatgccatc acaagcagaa gcattgcccg cccgcgctgt caggtggggg gctcccggcc    180
acaccgctgc tcttccaccc ccacactaag ggctcccaga tcctcatgga cctcagccac    240
aaggccgtca agaggcaggc cagcttctgt aatgccatca ccttcagcaa ccgccccgtc    300
ctcatctacg agcaagtcag gctgaagatc accaagaagc agtgctgctg gagcggggcc    360
ctgcgacttg gcttcaccag caaggaccct tcccgcatcc accccgactc actgcccaag    420
tacgcctgcc ctgacctggt gtcccagagt ggcttctggg ccaaagcgtt gcctgaggag    480
tttgccaacg agggcaacat cattgccttc tgggtggaca agaagggccg agtcttctac    540
cggatcaatg agtcggctgc catgctgttc ttcagcgggg ttcgaacggc ggacccgctc    600
tgggccctgg tggacgtcta tggcctcaca cggggtgtcc agctgctagg aacagccccc    660
aactcacctg tgagcctgcc cgagtcacca gtgaccccgg gtctgggcca gtggagcgat    720
gaatgcacca tttgctatga acacgcagtg gatacagtca tctacacgtg tggccacatg    780
tgcctgtgct actcctgtgg cctgcgcctc aagaaggccc tgcacgcctg ctgccccatc    840
tgccgtcgcc ccatcaagga catcatcaag acctaccgca gctcctag                 888
```

<210> SEQ ID NO 20
<211> LENGTH: 295
<212> TYPE: PRT
<213> ORGANISM: rat

<400> SEQUENCE: 20

```
Met Gly Asn Asn Phe Ser Ser Val Ser Ser Leu Gln Arg Gly Asn Pro
1               5                   10                  15

Ser Arg Ala Ser Arg Gly His Pro Gln Asn Leu Lys Asp Ser Ile Gly
            20                  25                  30

Ser Ser Phe Pro Val Pro Ser His Arg Cys His His Lys Gln Lys His
        35                  40                  45
```

```
Cys Pro Pro Ala Leu Ser Gly Gly Leu Pro Ala Thr Pro Leu Leu
 50                  55                  60

Phe His Pro His Thr Lys Gly Ser Gln Ile Leu Met Asp Leu Ser His
 65                  70                  75                  80

Lys Ala Val Lys Arg Gln Ala Ser Phe Cys Asn Ala Ile Thr Phe Ser
                 85                  90                  95

Asn Arg Pro Val Leu Ile Tyr Glu Gln Val Arg Leu Lys Ile Thr Lys
            100                 105                 110

Lys Gln Cys Cys Trp Ser Gly Ala Leu Arg Leu Gly Phe Thr Ser Lys
            115                 120                 125

Asp Pro Ser Arg Ile His Pro Asp Ser Leu Pro Lys Tyr Ala Cys Pro
130                 135                 140

Asp Leu Val Ser Gln Ser Gly Phe Trp Ala Lys Ala Leu Pro Glu Glu
145                 150                 155                 160

Phe Ala Asn Glu Gly Asn Ile Ile Ala Phe Trp Val Asp Lys Lys Gly
                165                 170                 175

Arg Val Phe Tyr Arg Ile Asn Glu Ser Ala Ala Met Leu Phe Phe Ser
            180                 185                 190

Gly Val Arg Thr Ala Asp Pro Leu Trp Ala Leu Val Asp Val Tyr Gly
            195                 200                 205

Leu Thr Arg Gly Val Gln Leu Leu Gly Thr Ala Pro Asn Ser Pro Val
210                 215                 220

Ser Leu Pro Glu Ser Pro Val Thr Pro Gly Leu Gly Gln Trp Ser Asp
225                 230                 235                 240

Glu Cys Thr Ile Cys Tyr Glu His Ala Val Asp Thr Val Ile Tyr Thr
                245                 250                 255

Cys Gly His Met Cys Leu Cys Tyr Ser Cys Gly Leu Arg Leu Lys Lys
            260                 265                 270

Ala Leu His Ala Cys Cys Pro Ile Cys Arg Arg Pro Ile Lys Asp Ile
            275                 280                 285

Ile Lys Thr Tyr Arg Ser Ser
290                 295

<210> SEQ ID NO 21
<211> LENGTH: 1675
<212> TYPE: DNA
<213> ORGANISM: Homo sapien

<400> SEQUENCE: 21
atgggcaaca cggtgcaccg gaccctgcca gacccgagcc caccggcgcg cctcctggcc      60
acccggccgt gctgcggccc cggccccgag cgacgcccgg tcctgggcga ggcgccgcgc     120
ttccacgcgc aggccaaagg caagaacgtg cggctggacg ccactcgcg  ccgggccaca     180 cggcgcaaca gcttctgcaa tggcgtcacg ttcacgcagc ggcccatccg gctgtacgag     240
caggtgcggc tgcgcctggt ggccgtgcgc cctggctgga gcggcgcgct cgcttcggc      300 ttcaccgcgc acgatccgtc gctcatgagc gcccaggaca tccccaagta cgcctgcccg     360
gacctggtca gcggccgggc tactgggcc  aaggcactgc ccgagaacct ggcgctgcgc     420
gacacggtgc tggcctactg gccgaccgc  cacggccgcg tgttctacag cgtgaacgac     480
ggcgagccgg tgctcttcca ctgcggcgtg ccgtgggcg  gccgctctg  ggcgctcatt     540 gatgtctacg gcatcaccga cgaggtgcag cttctggaga gcgccttcgc tgacacgctg     600
acgcccgcgc gcctcagcca ggcccgcttc agcgcctgcc tgccgcccag cagccacgac     660
gcggccaact tcgacaacaa cgagctcgag aacaaccagg tggtggccaa gctgggccac     720
```

```
ctggcgctgg gccgcgcccc gggcccaccg ccagccgacg ccgcggccgc cgccattccg    780
tgcgggcccc gtgagcgccc gcggcccgcg tcgtcgccgg cgctactgga ggccgacctg    840
cgcttccacg caacacgcgg gcccgacgtg agcctgtcgg ccgaccgcaa agtggcctgc    900
gcaccgcggc ccgacggcgg ccgcacgctg gtcttctccg agcgcccgct gcggcccggc    960
gagagcctct tcgtggaggt gggccgtccg gggctggcgg cgcccggcgc gctggccttc   1020
ggcatcacgt cgtgcgaccc gggcgtgcta cggcccaacg agctgcccgc cgacccagac   1080
gcgctgctcg accgcaaaga gtactgggtg gtggcgcgcg ccgggcccgt gccgagcggc   1140
ggcgacgcgc tcagcttcac gctgcggccc ggcggcgacg tgctcctggg catcaacggg   1200
cgtccgcgcg ccgcctgct gtgcgtcgac accacgcagg cgctctgggc cttcttcgcc   1260
gtgcgcggcg gcgtcgcggg ccagctgcgt ctcctcggta ccctgcagtc cagccctgcg   1320
accacgactc catcagggtc cctcagcggc tcccaggacg atagtgattc agatatgacc   1380
ttcagtgtca accagtcctc ctcggcatct gagtcatccc tggtgacggc ccccagctcc   1440
ccgctgagcc ccccggtgtc ccccgtgttc tccccaccgg agccggcagg catcaagaat   1500
ggcgagtgca cggtgtgctt cgatggcgag gtggacacgg tcatctacac gtgtggacac   1560
atgtgcctgt gccacagctg cggcctgcgg ctcaagcgac aggcccgggc ctgctgcccc   1620
atctgccggc ggcccatcaa ggacgtcatt aagatctaca ggccatagcc tagcc         1675
```

<210> SEQ ID NO 22
<211> LENGTH: 555
<212> TYPE: PRT
<213> ORGANISM: Homo sapien

<400> SEQUENCE: 22

Met Gly Asn Thr Val His Arg Thr Leu Pro Asp Pro Ser Pro Pro Ala
 1               5                  10                  15

Arg Leu Leu Ala Thr Arg Pro Cys Cys Gly Pro Gly Pro Glu Arg Arg
            20                  25                  30

Pro Val Leu Gly Glu Ala Pro Arg Phe His Ala Gln Ala Lys Gly Lys
        35                  40                  45

Asn Val Arg Leu Asp Gly His Ser Arg Arg Ala Thr Arg Arg Asn Ser
    50                  55                  60

Phe Cys Asn Gly Val Thr Phe Thr Gln Arg Pro Ile Arg Leu Tyr Glu
65                  70                  75                  80

Gln Val Arg Leu Arg Leu Val Ala Val Arg Pro Gly Trp Ser Gly Ala
                85                  90                  95

Leu Arg Phe Gly Phe Thr Ala His Asp Pro Ser Leu Met Ser Ala Gln
            100                 105                 110

Asp Ile Pro Lys Tyr Ala Cys Pro Asp Leu Val Thr Arg Pro Gly Tyr
        115                 120                 125

Trp Ala Lys Ala Leu Pro Glu Asn Leu Ala Leu Arg Asp Thr Val Leu
    130                 135                 140

Ala Tyr Trp Ala Asp Arg His Gly Arg Val Phe Tyr Ser Val Asn Asp
145                 150                 155                 160

Gly Glu Pro Val Leu Phe His Cys Gly Val Ala Val Gly Gly Pro Leu
                165                 170                 175

Trp Ala Leu Ile Asp Val Tyr Gly Ile Thr Asp Glu Val Gln Leu Leu
            180                 185                 190

Glu Ser Ala Phe Ala Asp Thr Leu Thr Pro Ala Arg Leu Ser Gln Ala
        195                 200                 205

```
Arg Phe Ser Ala Cys Leu Pro Pro Ser Ser His Asp Ala Ala Asn Phe
    210                 215                 220

Asp Asn Asn Glu Leu Glu Asn Asn Gln Val Val Ala Lys Leu Gly His
225                 230                 235                 240

Leu Ala Leu Gly Arg Ala Pro Gly Pro Pro Ala Asp Ala Ala Ala
                245                 250                 255

Ala Ala Ile Pro Cys Gly Pro Arg Glu Arg Pro Arg Pro Ala Ser Ser
            260                 265                 270

Pro Ala Leu Leu Glu Ala Asp Leu Arg Phe His Ala Thr Arg Gly Pro
                275                 280                 285

Asp Val Ser Leu Ser Ala Asp Arg Lys Val Ala Cys Ala Pro Arg Pro
    290                 295                 300

Asp Gly Gly Arg Thr Leu Val Phe Ser Glu Arg Pro Leu Arg Pro Gly
305                 310                 315                 320

Glu Ser Leu Phe Val Glu Val Gly Arg Pro Gly Leu Ala Ala Pro Gly
                325                 330                 335

Ala Leu Ala Phe Gly Ile Thr Ser Cys Asp Pro Gly Val Leu Arg Pro
            340                 345                 350

Asn Glu Leu Pro Ala Asp Pro Asp Ala Leu Leu Asp Arg Lys Glu Tyr
                355                 360                 365

Trp Val Val Ala Arg Ala Gly Pro Val Pro Ser Gly Gly Asp Ala Leu
    370                 375                 380

Ser Phe Thr Leu Arg Pro Gly Gly Asp Val Leu Leu Gly Ile Asn Gly
385                 390                 395                 400

Arg Pro Arg Gly Arg Leu Leu Cys Val Asp Thr Thr Gln Ala Leu Trp
                405                 410                 415

Ala Phe Phe Ala Val Arg Gly Gly Val Ala Gly Gln Leu Arg Leu Leu
            420                 425                 430

Gly Thr Leu Gln Ser Ser Pro Ala Thr Thr Thr Pro Ser Gly Ser Leu
                435                 440                 445

Ser Gly Ser Gln Asp Asp Ser Asp Ser Asp Met Thr Phe Ser Val Asn
450                 455                 460

Gln Ser Ser Ser Ala Ser Glu Ser Ser Leu Val Thr Ala Pro Ser Ser
465                 470                 475                 480

Pro Leu Ser Pro Pro Val Ser Pro Val Phe Ser Pro Pro Glu Pro Ala
                485                 490                 495

Gly Ile Lys Asn Gly Glu Cys Thr Val Cys Phe Asp Gly Glu Val Asp
            500                 505                 510

Thr Val Ile Tyr Thr Cys Gly His Met Cys Leu Cys His Ser Cys Gly
    515                 520                 525

Leu Arg Leu Lys Arg Gln Ala Arg Ala Cys Cys Pro Ile Cys Arg Arg
    530                 535                 540

Pro Ile Lys Asp Val Ile Lys Ile Tyr Arg Pro
545                 550                 555

<210> SEQ ID NO 23
<211> LENGTH: 1129
<212> TYPE: DNA
<213> ORGANISM: Homo sapien

<400> SEQUENCE: 23
atgggcaaca cggtgcaccg gaccctgcca gagagcgcct tcgctgacac gctgacgccc      60
gcgcgcctca gccaggcccg cttcagcgcc tgcctgccgc ccagcagcca cgacgcggcc     120
aacttcgaca caacgagct cgagaacaac caggtggtgg ccaagctggg ccacctggcg     180
```

-continued

```
ctgggccgcg ccccgggccc accgccagcc gacgccgcgg ccgccgccat tccgtgcggg      240
ccccgtgagc gcccgcggcc cgcgtcgtcg ccggcgctac tggaggccga cctgcgcttc      300
cacgcaacac gcgggcccga cgtgagcctg tcggccgacc gcaaagtggc ctgcgcaccg      360
cggcccgacg gcggccgcac gctggtcttc tccgagcgcc cgctgcggcc cggcgagagc      420
ctcttcgtgg aggtgggccg tccggggctg gcggcgcccg gcgcgctggc cttcggcatc      480
acgtcgtgcg acccgggcgt gctacggccc aacgagctgc ccgccgaccc agacgcgctg      540
ctcgaccgca aagagtactg ggtggtggcg cgcgccgggc ccgtgccgag cggcggcgac      600
gcgctcagct tcacgctgcg gccccggcgg cgacgtgctcc tgggcatcaa cgggcgtccg      660
cgcggccgcc tgctgtgcgt cgacaccacg caggcgctct gggccttctt cgccgtgcgc      720
ggcggcgtcg cgggccagct gcgtctcctc ggtaccctgc agtccagccc tgcgaccacg      780
actccatcag ggtccctcag cggctcccag gacgatagtg attcagatat gaccttcagt      840
gtcaaccagt cctcctcggc atctgagtca tccctggtga cggcccccag ctccccgctg      900
agccccccgg tgtccccccgt gttctcccca ccggagccgg caggcatcaa gaatggcgag      960
tgcacggtgt gcttcgatgg cgaggtggac acggtcatct acacgtgtgg acacatgtgc     1020
ctgtgccaca gctgcggcct gcggctcaag cgacaggccc gggcctgctg ccccatctgc     1080
cggcggccca tcaaggacgt cattaagatc tacaggccat agcctagcc                 1129
```

<210> SEQ ID NO 24
<211> LENGTH: 373
<212> TYPE: PRT
<213> ORGANISM: Homo sapien

<400> SEQUENCE: 24

```
Met Gly Asn Thr Val His Arg Thr Leu Pro Glu Ser Ala Phe Ala Asp
 1               5                   10                  15

Thr Leu Thr Pro Ala Arg Leu Ser Gln Ala Arg Phe Ser Ala Cys Leu
             20                  25                  30

Pro Pro Ser Ser His Asp Ala Ala Asn Phe Asp Asn Asn Glu Leu Glu
         35                  40                  45

Asn Gln Val Val Ala Lys Leu Gly His Leu Ala Leu Gly Arg Ala
 50                  55                  60

Pro Gly Pro Pro Ala Asp Ala Ala Ala Ala Ile Pro Cys Gly
 65                  70                  75                  80

Pro Arg Glu Arg Pro Arg Pro Ala Ser Ser Pro Ala Leu Leu Glu Ala
                 85                  90                  95

Asp Leu Arg Phe His Ala Thr Arg Gly Pro Asp Val Ser Leu Ser Ala
            100                 105                 110

Asp Arg Lys Val Ala Cys Ala Pro Arg Pro Asp Gly Gly Arg Thr Leu
        115                 120                 125

Val Phe Ser Glu Arg Pro Leu Arg Pro Gly Glu Ser Leu Phe Val Glu
    130                 135                 140

Val Gly Arg Pro Gly Leu Ala Ala Pro Gly Ala Leu Ala Phe Gly Ile
145                 150                 155                 160

Thr Ser Cys Asp Pro Gly Val Leu Arg Pro Asn Glu Leu Pro Ala Asp
                165                 170                 175

Pro Asp Ala Leu Leu Asp Arg Lys Glu Tyr Trp Val Val Ala Arg Ala
            180                 185                 190

Gly Pro Val Pro Ser Gly Gly Asp Ala Leu Ser Phe Thr Leu Arg Pro
        195                 200                 205
```

```
Gly Gly Asp Val Leu Leu Gly Ile Asn Gly Arg Pro Arg Gly Arg Leu
            210                 215                 220
Leu Cys Val Asp Thr Thr Gln Ala Leu Trp Ala Phe Phe Ala Val Arg
225                 230                 235                 240
Gly Gly Val Ala Gly Gln Leu Arg Leu Leu Gly Thr Leu Gln Ser Ser
                245                 250                 255
Pro Ala Thr Thr Thr Pro Ser Gly Ser Leu Ser Gly Ser Gln Asp Asp
                260                 265                 270
Ser Asp Ser Asp Met Thr Phe Ser Val Asn Gln Ser Ser Ser Ala Ser
            275                 280                 285
Glu Ser Ser Leu Val Thr Ala Pro Ser Ser Pro Leu Ser Pro Pro Val
        290                 295                 300
Ser Pro Val Phe Ser Pro Pro Glu Pro Ala Gly Ile Lys Asn Gly Glu
305                 310                 315                 320
Cys Thr Val Cys Phe Asp Gly Glu Val Asp Thr Val Ile Tyr Thr Cys
                325                 330                 335
Gly His Met Cys Leu Cys His Ser Cys Gly Leu Arg Leu Lys Arg Gln
                340                 345                 350
Ala Arg Ala Cys Cys Pro Ile Cys Arg Arg Pro Ile Lys Asp Val Ile
            355                 360                 365
Lys Ile Tyr Arg Pro
    370

<210> SEQ ID NO 25
<211> LENGTH: 955
<212> TYPE: DNA
<213> ORGANISM: Homo sapien

<400> SEQUENCE: 25
atgggcaaca cggtgcaccg gaccctgcca gacccgagcc caccggcgcg cctcctggcc      60
acccggccgt gctgcggccc cggccccgag cgacgcccgg tcctgggcga ggcgccgcgc     120
ttccacgcgc aggccaaagg caagaacgtg cggctggacg ccactcgcg ccgggccaca     180
cggcgcaaca gcttctgcaa tggcgtcacg ttcacgcagc ggcccatccg gctgtacgag     240
caggtgcggc tgcgcctggt ggccgtgcgc cctggctgga gcggcgcgct gcgcttcggc     300
ttcaccgcgc acgatccgtc gctcatgagc gcccaggaca tccccaagta cgcctgcccg     360
gacctggtca gcggccgggc tactgggcc aaggcactgc ccgagaacct ggcgctgcgc     420
gacacggtgc tggcctactg gccgaccgc acggccgcg tgttctacag cgtgaacgac     480
ggcgagccgg tgctcttcca ctgcggcgtg gccgtgggcg cccgctctg gcgctcatt     540
gatgtctacg gcatcaccga cgaggtgcag cttctgggta ccctgcagtc cagccctgcg     600
accacgactc catcagggtc cctcagcggc tcccaggacg atagtgattc agatatgacc     660
ttcagtgtca accagtcctc ctcggcatct gagtcatccc tggtgacggc ccccagctcc     720
ccgctgagcc ccccggtgtc ccccgtgttc tccccaccgg agccggcagg catcaagaat     780
ggcgagtgca cggtgtgctt cgatggcgag gtggacacgg tcatctacac gtgtggacac     840
atgtgcctgt gccacagctg cggcctgcgg ctcaagcgac aggcccgggc ctgctgcccc     900
atctgccggc ggcccatcaa ggacgtcatt aagatctaca ggccatagcc tagcc          955

<210> SEQ ID NO 26
<211> LENGTH: 315
<212> TYPE: PRT
<213> ORGANISM: Homo sapien
```

<400> SEQUENCE: 26

```
Met Gly Asn Thr Val His Arg Thr Leu Pro Asp Pro Ser Pro Pro Ala
1               5                   10                  15
Arg Leu Leu Ala Thr Arg Pro Cys Cys Gly Pro Gly Pro Glu Arg Arg
            20                  25                  30
Pro Val Leu Gly Glu Ala Pro Arg Phe His Ala Gln Ala Lys Gly Lys
        35                  40                  45
Asn Val Arg Leu Asp Gly His Ser Arg Arg Ala Thr Arg Arg Asn Ser
    50                  55                  60
Phe Cys Asn Gly Val Thr Phe Thr Gln Arg Pro Ile Arg Leu Tyr Glu
65                  70                  75                  80
Gln Val Arg Leu Arg Leu Val Ala Val Arg Pro Gly Trp Ser Gly Ala
                85                  90                  95
Leu Arg Phe Gly Phe Thr Ala His Asp Pro Ser Leu Met Ser Ala Gln
            100                 105                 110
Asp Ile Pro Lys Tyr Ala Cys Pro Asp Leu Val Thr Arg Pro Gly Tyr
        115                 120                 125
Trp Ala Lys Ala Leu Pro Glu Asn Leu Ala Leu Arg Asp Thr Val Leu
    130                 135                 140
Ala Tyr Trp Ala Asp Arg His Gly Arg Val Phe Tyr Ser Val Asn Asp
145                 150                 155                 160
Gly Glu Pro Val Leu Phe His Cys Gly Val Ala Val Gly Gly Pro Leu
                165                 170                 175
Trp Ala Leu Ile Asp Val Tyr Gly Ile Thr Asp Glu Val Gln Leu Leu
            180                 185                 190
Gly Thr Leu Gln Ser Ser Pro Ala Thr Thr Thr Pro Ser Gly Ser Leu
        195                 200                 205
Ser Gly Ser Gln Asp Asp Ser Asp Ser Asp Met Thr Phe Ser Val Asn
    210                 215                 220
Gln Ser Ser Ser Ala Ser Glu Ser Ser Leu Val Thr Ala Pro Ser Ser
225                 230                 235                 240
Pro Leu Ser Pro Pro Val Ser Pro Val Phe Ser Pro Pro Glu Pro Ala
                245                 250                 255
Gly Ile Lys Asn Gly Glu Cys Thr Val Cys Phe Asp Gly Glu Val Asp
            260                 265                 270
Thr Val Ile Tyr Thr Cys Gly His Met Cys Leu Cys His Ser Cys Gly
        275                 280                 285
Leu Arg Leu Lys Arg Gln Ala Arg Ala Cys Cys Pro Ile Cys Arg Arg
    290                 295                 300
Pro Ile Lys Asp Val Ile Lys Ile Tyr Arg Pro
305                 310                 315
```

<210> SEQ ID NO 27
<211> LENGTH: 1641
<212> TYPE: DNA
<213> ORGANISM: Rat

<400> SEQUENCE: 27

```
atgggcaaca cggtgcaccg gaccctgcca gactccagcc ctcctgcacg cctcctggcc      60
acccggcctt gctacggccc gggcccggag aggcgagcgg tcctgggcga ggcgccacgc     120
ttccacgcgc aggccaaggg caagaacgtg cgtctagacg gtcactcgcg cagggccacg     180
cgacggaaca gcttctgcaa cggagtcacc ttcacgcagc ggcccattcg cctgtacgag     240
caggtgcggt tgcgcctggt ggctgtgcgt cctggctgga gcggcgcgct cgcgcttcggc    300
```

```
ttcactgcgc acgacccgtc gctcatgagc gcacaggata tccccaagta cgcctgcccc    360
gacctggtca cacgacctgg atactgggcc aaggcgctgc cggagaacct ggcgctgcgg    420
gacacggtgc tggcctactg gctgatcgt cacggtcgcg tcttctatag tgtctatgat     480
ggcgaaccag tgctgttcca ctgcggcgtg gccgtgggaa gcccactctg gcactcatc    540 gacgtctatg gcatcacgga cgaggtgcag ctgctggaaa gcacctgcgc agacacgctg    600
accccgctgc gcctgggcca ggcccgcctc agcgcctgcc cgcctccggg cagccacgat    660
gctgccaact tcgataataa cgagctggag aataaccagg tggtagccaa gctgggtcac    720
ttggctctcg gccgtccgga cgccgccgtc ccgtgcgtgg cccgcgaacg cgcgaggccc    780
gcttcttcac ccgcgttgct ggacgctgag ctgcgtttcc acgccacgcg cggccccgac    840
gtgagcctgt tgcggaccg caggttagct tgcgcgcccc gccccgacgg cggccgcacg     900
tttgtgttct ccgagcggcc gctgcggccc ggggagagcc tgtgcgtgga agtggggcgc    960
ccggggctgg cggcgcccgc agctgtggcc ttcggcatca cgtcctgcga tcctggcgcg   1020
ctgcggccat ccgagctgcc cgccgatccc gctgcgctgc tggaccgcaa ggaatactgg   1080
gtggtggcgc gcgccgggcc cgtgcccagc ggaggcgacg cactcagctt cacgctgcga   1140
ccgggcggcg acgtcctgct ggcggtgaac gggcgcccgc ggggacgctt gctgtgcgtg   1200
gacacctcgc aggcgctctg gccttcttc gctgtgcgcg tggtgtggc gggtcagctg    1260 cgtctcctgg gcaccgtaca gtccggtcct gaggccacaa ctccatcagg gtccttcagt   1320
ggctctcagg atgacagcga ttcggacatg accttcgggg tcaaccagtc gtcatcagca   1380
tcagaatcgt ctctggtgac agcccccagc tccccactga gtccccagt gtccccggcc    1440 ttctctgcac ccgagccggc cggcagcagg aatggagagt gcacggtgtg cttcgacagc   1500
gaggtggaca cggtcatcta cacgtgtgga cacatgtgcc tgtgccacag ctgccgcctg   1560
cggctccgaa agcaggcacg ggcctgctgt cctatctgcc gtcggcccat caaggatgtt   1620
atcaagatct ataggccgta g                                             1641
```

<210> SEQ ID NO 28
<211> LENGTH: 546
<212> TYPE: PRT
<213> ORGANISM: Rat

<400> SEQUENCE: 28

```
Met Gly Asn Thr Val His Arg Thr Leu Pro Asp Ser Pro Pro Ala
 1               5                  10                  15

Arg Leu Leu Ala Thr Arg Pro Cys Tyr Gly Pro Gly Pro Glu Arg Arg
             20                  25                  30

Ala Val Leu Gly Glu Ala Pro Arg Phe His Ala Gln Ala Lys Gly Lys
         35                  40                  45

Asn Val Arg Leu Asp Gly His Ser Arg Ala Thr Arg Arg Asn Ser
     50                  55                  60

Phe Cys Asn Gly Val Thr Phe Thr Gln Arg Pro Ile Arg Leu Tyr Glu
 65                  70                  75                  80

Gln Val Arg Leu Arg Leu Val Ala Val Arg Pro Gly Trp Ser Gly Ala
                 85                  90                  95

Leu Arg Phe Gly Phe Thr Ala His Asp Pro Ser Leu Met Ser Ala Gln
                100                 105                 110

Asp Ile Pro Lys Tyr Ala Cys Pro Asp Leu Val Thr Arg Pro Gly Tyr
            115                 120                 125
```

```
Trp Ala Lys Ala Leu Pro Glu Asn Leu Ala Leu Arg Asp Thr Val Leu
130                 135                 140

Ala Tyr Trp Ala Asp Arg His Gly Arg Val Phe Tyr Ser Val Tyr Asp
145                 150                 155                 160

Gly Glu Pro Val Leu Phe His Cys Gly Val Ala Val Gly Ser Pro Leu
                165                 170                 175

Trp Ala Leu Ile Asp Val Tyr Gly Ile Thr Asp Glu Val Gln Leu Leu
            180                 185                 190

Glu Ser Thr Cys Ala Asp Thr Leu Thr Pro Leu Arg Leu Gly Gln Ala
        195                 200                 205

Arg Leu Ser Ala Cys Pro Pro Gly Ser His Asp Ala Ala Asn Phe
210                 215                 220

Asp Asn Asn Glu Leu Glu Asn Asn Gln Val Val Ala Lys Leu Gly His
225                 230                 235                 240

Leu Ala Leu Gly Arg Pro Asp Ala Ala Val Pro Cys Val Ala Arg Glu
                245                 250                 255

Arg Ala Arg Pro Ala Ser Ser Pro Ala Leu Leu Asp Ala Glu Leu Arg
                260                 265                 270

Phe His Ala Thr Arg Gly Pro Asp Val Ser Leu Phe Ala Asp Arg Arg
            275                 280                 285

Leu Ala Cys Ala Pro Arg Pro Asp Gly Gly Arg Thr Phe Val Phe Ser
        290                 295                 300

Glu Arg Pro Leu Arg Pro Gly Glu Ser Leu Cys Val Glu Val Gly Arg
305                 310                 315                 320

Pro Gly Leu Ala Ala Pro Ala Ala Val Ala Phe Gly Ile Thr Ser Cys
                325                 330                 335

Asp Pro Gly Ala Leu Arg Pro Ser Glu Leu Pro Ala Asp Pro Ala Ala
                340                 345                 350

Leu Leu Asp Arg Lys Glu Tyr Trp Val Val Arg Ala Gly Pro Val
            355                 360                 365

Pro Ser Gly Gly Asp Ala Leu Ser Phe Thr Leu Arg Pro Gly Gly Asp
    370                 375                 380

Val Leu Leu Ala Val Asn Gly Arg Pro Arg Gly Arg Leu Leu Cys Val
385                 390                 395                 400

Asp Thr Ser Gln Ala Leu Trp Ala Phe Phe Ala Val Arg Gly Gly Val
                405                 410                 415

Ala Gly Gln Leu Arg Leu Leu Gly Thr Val Gln Ser Gly Pro Glu Ala
                420                 425                 430

Thr Thr Pro Ser Gly Ser Phe Ser Gly Ser Gln Asp Asp Ser Asp Ser
            435                 440                 445

Asp Met Thr Phe Gly Val Asn Gln Ser Ser Ala Ser Glu Ser Ser
        450                 455                 460

Leu Val Thr Ala Pro Ser Ser Pro Leu Ser Pro Val Ser Pro Ala
465                 470                 475                 480

Phe Ser Ala Pro Glu Pro Ala Gly Ser Arg Asn Gly Glu Cys Thr Val
                485                 490                 495

Cys Phe Asp Ser Glu Val Asp Thr Val Ile Tyr Thr Cys Gly His Met
            500                 505                 510

Cys Leu Cys His Ser Cys Arg Leu Arg Leu Arg Lys Gln Ala Arg Ala
        515                 520                 525
```

```
Cys Cys Pro Ile Cys Arg Arg Pro Ile Lys Asp Val Ile Lys Ile Tyr
            530                 535                 540
Arg Pro
545

<210> SEQ ID NO 29
<211> LENGTH: 789
<212> TYPE: DNA
<213> ORGANISM: Homo sapien

<400> SEQUENCE: 29
atgggtgccc agctctgctt tgaggccaac gccaaggcgc cccgagaggc acttcgcttc      60
catgccgagg ccaagggcgc acaggtgcgt ctggacacgc gtggctgcat cgcgcacagg     120
cgcaccacgt tccacgacgg catcgtgttc agccagcggc cggtgcgcct gggcgagcgt     180
gtggcgctgc gagtgctgcg ggaggagagc ggctggtgcg gcggcctccg cgtgggcttc     240
acgcgcctgg accccgcgtg cgtgtccgtg cccagcctgc cgcccttcct gtgccccgac     300
ctggaggagc agagcccgac gtgggcggcc gtgctgcctg agggctgcgc gctcactggg     360
gacttggtcc gcttctgggt ggaccgccgc ggctgcctct cgccaaggt caacgccggc      420 tgccggctcc tgctgcgtga gggcgtgccc gtcggcgccc cgctctgggc cgtgatggac     480
gtgtatggga ccactaaggc catcgagctg ctggatccca cagccagccg gctcccaaca     540
cccatgccat gggacctcag caacaaggct gtgcctgagc ccaaagccac accaggagag     600
gagtgtgcca tctgcttcta tcacgctgcc aacacccgcc ttgtgccctg cggccacaca     660
tacttctgca gatactgtgc ctggcgggtc ttcagcgata cggccaagtg ccctgtgtgc     720
cgctggcaga tagaggcggt agcccctgcg cagggccctc ctgctctgag ggttgaggaa     780
ggctcatga                                                            789

<210> SEQ ID NO 30
<211> LENGTH: 262
<212> TYPE: PRT
<213> ORGANISM: Homo sapien

<400> SEQUENCE: 30

Met Gly Ala Gln Leu Cys Phe Glu Ala Asn Ala Lys Ala Pro Arg Glu
1               5                   10                  15

Ala Leu Arg Phe His Ala Glu Ala Lys Gly Ala Gln Val Arg Leu Asp
            20                  25                  30

Thr Arg Gly Cys Ile Ala His Arg Arg Thr Thr Phe His Asp Gly Ile
        35                  40                  45

Val Phe Ser Gln Arg Pro Val Arg Leu Gly Glu Arg Val Ala Leu Arg
    50                  55                  60

Val Leu Arg Glu Glu Ser Gly Trp Cys Gly Gly Leu Arg Val Gly Phe
65                  70                  75                  80

Thr Arg Leu Asp Pro Ala Cys Val Ser Val Pro Ser Leu Pro Pro Phe
                85                  90                  95

Leu Cys Pro Asp Leu Glu Glu Gln Ser Pro Thr Trp Ala Ala Val Leu
            100                 105                 110

Pro Glu Gly Cys Ala Leu Thr Gly Asp Leu Val Arg Phe Trp Val Asp
        115                 120                 125

Arg Arg Gly Cys Leu Phe Ala Lys Val Asn Ala Gly Cys Arg Leu Leu
    130                 135                 140

Leu Arg Glu Gly Val Pro Val Gly Ala Pro Leu Trp Ala Val Met Asp
145                 150                 155                 160
```

```
Val Tyr Gly Thr Thr Lys Ala Ile Glu Leu Leu Asp Pro Thr Ala Ser
            165                 170                 175

Arg Leu Pro Thr Pro Met Pro Trp Asp Leu Ser Asn Lys Ala Val Pro
            180                 185                 190

Glu Pro Lys Ala Thr Pro Gly Glu Cys Ala Ile Cys Phe Tyr His
            195                 200                 205

Ala Ala Asn Thr Arg Leu Val Pro Cys Gly His Thr Tyr Phe Cys Arg
    210                 215                 220

Tyr Cys Ala Trp Arg Val Phe Ser Asp Thr Ala Lys Cys Pro Val Cys
225                 230                 235                 240

Arg Trp Gln Ile Glu Ala Val Ala Pro Ala Gln Gly Pro Pro Ala Leu
                245                 250                 255

Arg Val Glu Glu Gly Ser
            260
```

<210> SEQ ID NO 31
<211> LENGTH: 765
<212> TYPE: DNA
<213> ORGANISM: mouse

<400> SEQUENCE: 31

| | | | | | |
|---|---|---|---|---|---|
| atgggttctc | tcctcagccc | tgaggccaat | gccgaggtgc | cccgcgaggc | ccttagtttc | 60 |
| cacgggaacg | ccacgggcgc | acaggtgcat | ctggacgatc | agcggagcac | agcgcgcagg | 120 |
| cgctcgacgt | tccacgatgg | tatcgtgttc | agccagaggc | cggtctggcc | gggtgagcgt | 180 |
| gttgctctgc | gcgtcctgcg | acatgaagaa | ggctggtgcg | gtggcctccg | cgtgggcttc | 240 |
| acgcgcctgg | accctgcgca | agtggccgcg | tcctgcctgc | cacccttcgt | gtgcccggac | 300 |
| ctggaggagc | agagtccac | gtgggcagcg | ttgcttccag | agggcttcgt | tcgtgcgggg | 360 |
| aatgtggtct | gcttctgggt | gaaccgtaga | gggtggctct | tcgccaaggt | caacgctggc | 420 |
| cgccccctct | gctgcgcaa | agacgtgctg | gtccagggcg | ccccgctctg | ggcggtgatg | 480 |
| gatgtgtacg | ggaccacgaa | agccattgag | cttctggatc | ccaaagccaa | cgcctggatt | 540 |
| cgtagtggtg | agcctgtgcc | agagtctgaa | gtcatatcag | agaggagtg | tgtcatctgc | 600 |
| ttccacaaca | ctgccaacac | ccgcctcatg | ccctgtggcc | actcacactt | ctgtggctcc | 660 |
| tgtgcctggc | acatcttcaa | agacacggcc | aggtgcccca | tatgtcgctg | cagatcgag | 720 |
| gaggtggctg | tagtgtcttc | actgaaggct | gaggaaggct | cctga | | 765 |

<210> SEQ ID NO 32
<211> LENGTH: 254
<212> TYPE: PRT
<213> ORGANISM: mouse

<400> SEQUENCE: 32

```
Met Gly Ser Leu Leu Ser Pro Glu Ala Asn Ala Glu Val Pro Arg Glu
1               5                   10                  15

Ala Leu Ser Phe His Gly Asn Ala Thr Gly Ala Gln Val His Leu Asp
            20                  25                  30

Asp Gln Arg Ser Thr Ala Arg Arg Ser Thr Phe His Asp Gly Ile
        35                  40                  45

Val Phe Ser Gln Arg Pro Val Trp Pro Gly Glu Arg Val Ala Leu Arg
    50                  55                  60

Val Leu Arg His Glu Glu Gly Trp Cys Gly Gly Leu Arg Val Gly Phe
65                  70                  75                  80
```

```
Thr Arg Leu Asp Pro Ala Gln Val Ala Ala Ser Cys Leu Pro Pro Phe
                85                  90                  95

Val Cys Pro Asp Leu Glu Glu Gln Ser Pro Thr Trp Ala Ala Leu Leu
            100                 105                 110

Pro Glu Gly Phe Val Arg Ala Gly Asn Val Val Cys Phe Trp Val Asn
        115                 120                 125

Arg Arg Gly Trp Leu Phe Ala Lys Val Asn Ala Gly Arg Pro Leu Leu
    130                 135                 140

Leu Arg Lys Asp Val Leu Val Gln Gly Ala Pro Leu Trp Ala Val Met
145                 150                 155                 160

Asp Val Tyr Gly Thr Thr Lys Ala Ile Glu Leu Leu Asp Pro Lys Ala
                165                 170                 175

Asn Ala Trp Ile Arg Ser Gly Glu Pro Val Pro Glu Ser Glu Val Ile
            180                 185                 190

Ser Gly Glu Glu Cys Val Ile Cys Phe His Asn Thr Ala Asn Thr Arg
        195                 200                 205

Leu Met Pro Cys Gly His Ser His Phe Cys Gly Ser Cys Ala Trp His
    210                 215                 220

Ile Phe Lys Asp Thr Ala Arg Cys Pro Ile Cys Arg Trp Gln Ile Glu
225                 230                 235                 240

Glu Val Ala Val Val Ser Ser Leu Lys Ala Glu Glu Gly Ser
                245                 250
```

<210> SEQ ID NO 33
<211> LENGTH: 250
<212> TYPE: DNA
<213> ORGANISM: Homo sapien
<400> SEQUENCE: 33

```
cgcttccatc gggtgcacgg tgccaacatc cgcgtggacc cctctgggac gcgggccaca    60
cgcgtggaga gcttcgccca cggcgtgtgc ttcagccgcg agccgctggc cccgggccag   120
gtcttcctgg tcgagatcga ggagaaagag ctgggctggt gcggacatct cgtctcggt   180 ctgaccgcgc tggaccccgc cagtctggcc ccgttcccg agttttctct gcccgatctg   240
gtcaacctgg                                                         250
```

<210> SEQ ID NO 34
<211> LENGTH: 83
<212> TYPE: PRT
<213> ORGANISM: Homo sapien
<400> SEQUENCE: 34

```
Arg Phe His Arg Val His Gly Ala Asn Ile Arg Val Asp Pro Ser Gly
1               5                   10                  15

Thr Arg Ala Thr Arg Val Glu Ser Phe Ala His Gly Val Cys Phe Ser
            20                  25                  30

Arg Glu Pro Leu Ala Pro Gly Gln Val Phe Leu Val Glu Ile Glu Glu
        35                  40                  45

Lys Glu Leu Gly Trp Cys Gly His Leu Arg Leu Gly Leu Thr Ala Leu
    50                  55                  60

Asp Pro Ala Ser Leu Ala Pro Val Pro Glu Phe Ser Leu Pro Asp Leu
65                  70                  75                  80

Val Asn Leu
```

<210> SEQ ID NO 35
<211> LENGTH: 1743
<212> TYPE: DNA
<213> ORGANISM: rat

<400> SEQUENCE: 35

| | | | | | |
|---|---|---|---|---|---|
| atggcggatt | tcgaggagtt | gaggaatatg | gtttctagtt | ttagggtttc | tgaattacaa | 60 |
| gtgttactgg | gctttgctgg | acggaataaa | agtgggcgca | agcatgacct | cctgatgagg | 120 |
| gcgttgcatt | tactgaagag | tggctgcagc | cctgcggttc | agattaaaat | tcgagaatta | 180 |
| tacagacgcc | gataccccacg | gacacttgaa | ggactttctg | atctatccac | aatcaaatct | 240 |
| tcagttttca | gtttggatgg | tagctcatca | ccagtagagc | ctgacttggc | cgtggctggg | 300 |
| atccactcgt | tgccttctac | ttccattgca | cctcattcac | cgtcatctcc | tgtcgcttct | 360 |
| gtgctgcttc | aagacactaa | gcccacgttt | gagatgcagc | aaccatctcc | tcccattcct | 420 |
| cctgtccatc | ctgacgtgca | gttaaaaacg | ctgcccttct | atgacgtcct | tgatgttctc | 480 |
| atcaagccca | caagtttagt | tcaaagcagt | attcagcggt | tcaagagaa | gttttttatt | 540 |
| tttgctttga | caccccagca | agttagagag | atatgcattt | caagggattt | tttgccaggt | 600 |
| ggcaggagag | actacacagt | ccaagtccag | ctgcgacttt | gcttggcaga | gaccagttgc | 660 |
| cctcaagaag | ataactatcc | caatagtttg | tgtataaaag | taaatgggaa | actctttcct | 720 |
| ttgcctggct | atgcaccacc | acctaaaaat | gggatcgaac | agaagcgtcc | tggacgcccc | 780 |
| ctgaatatta | catctttagt | gagattgtct | tcagctgtgc | caaatcagat | ttctatttct | 840 |
| tgggcatctg | aaattggaaa | gaattactcc | atgtctgtgt | atcttgtacg | acagcttaca | 900 |
| tcagccatgt | tattacagag | attaaaaatg | aaaggtatta | gaaatcctga | tcattccaaa | 960 |
| gcactcatta | agaaaaaact | tactgcagat | cctgatagtg | aaattgctac | aactagtctt | 1020 |
| cgagtgtcct | tgatgtgccc | tttaggaaaa | atgaggctga | caatcccgtg | ccgcgcagtg | 1080 |
| acgtgtacac | atctgcagtg | ctttgatgct | gccctgtatc | ttcagatgaa | tgagaagaag | 1140 |
| cccacctgga | tttgtcctgt | ttgtgacaaa | aaggctgcct | atgagagtct | gatactagat | 1200 |
| gggctttta | tggaaattct | caatgactgt | tctgatgtgg | atgagatcaa | attccaggaa | 1260 |
| gatggttcct | ggtgccccat | gagacctaag | aaagaagcta | tgaaagtaac | cagccagccc | 1320 |
| tgtacaaaag | tagaaagttc | aagtgtcttt | agtaaaacctt | gttcagtgac | tgtagccagt | 1380 |
| gatgcaagca | agaagaagat | tgatgttatt | gatctaacaa | tagagagctc | ttctgatgaa | 1440 |
| gaggaagacc | ctcccgccaa | aaggaaatgc | atctttatgt | cagaaacaca | aagcagtcca | 1500 |
| accaaagggg | ttctcatgta | tcagccatct | tctgtaaggg | tgcccagtgt | gacttcagtt | 1560 |
| gatcctgctg | ctattccacc | ttcattaaca | gactactcag | taccattcca | ccacacgcca | 1620 |
| gtgtcgagca | tgtcatcaga | tttgccaggt | ttggattttc | tttcccttat | tccagttgat | 1680 |
| ccccagtctc | acctcacccct | taacagcaag | cagtacgtct | gtcaccacca | ccagccccca | 1740 |
| tga | | | | | | 1743 |

<210> SEQ ID NO 36
<211> LENGTH: 580
<212> TYPE: PRT
<213> ORGANISM: rat

```
<400> SEQUENCE: 36

Met Ala Asp Phe Glu Glu Leu Arg Asn Met Val Ser Ser Phe Arg Val
  1               5                  10                  15

Ser Glu Leu Gln Val Leu Leu Gly Phe Ala Gly Arg Asn Lys Ser Gly
             20                  25                  30

Arg Lys His Asp Leu Leu Met Arg Ala Leu His Leu Leu Lys Ser Gly
         35                  40                  45

Cys Ser Pro Ala Val Gln Ile Lys Ile Arg Glu Leu Tyr Arg Arg Arg
     50                  55                  60

Tyr Pro Arg Thr Leu Glu Gly Leu Ser Asp Leu Ser Thr Ile Lys Ser
 65                  70                  75                  80

Ser Val Phe Ser Leu Asp Gly Ser Ser Pro Val Glu Pro Asp Leu
                 85                  90                  95

Ala Val Ala Gly Ile His Ser Leu Pro Ser Thr Ser Ile Ala Pro His
                100                 105                 110

Ser Pro Ser Ser Pro Val Ala Ser Val Leu Leu Gln Asp Thr Lys Pro
            115                 120                 125

Thr Phe Glu Met Gln Gln Pro Ser Pro Pro Ile Pro Pro Val His Pro
130                 135                 140

Asp Val Gln Leu Lys Thr Leu Pro Phe Tyr Asp Val Leu Asp Val Leu
145                 150                 155                 160

Ile Lys Pro Thr Ser Leu Val Gln Ser Ser Ile Gln Arg Phe Gln Glu
                165                 170                 175

Lys Phe Phe Ile Phe Ala Leu Thr Pro Gln Gln Val Arg Glu Ile Cys
            180                 185                 190

Ile Ser Arg Asp Phe Leu Pro Gly Gly Arg Arg Asp Tyr Thr Val Gln
        195                 200                 205

Val Gln Leu Arg Leu Cys Leu Ala Glu Thr Ser Cys Pro Gln Glu Asp
    210                 215                 220

Asn Tyr Pro Asn Ser Leu Cys Ile Lys Val Asn Gly Lys Leu Phe Pro
225                 230                 235                 240

Leu Pro Gly Tyr Ala Pro Pro Lys Asn Gly Ile Glu Gln Lys Arg
                245                 250                 255

Pro Gly Arg Pro Leu Asn Ile Thr Ser Leu Val Arg Leu Ser Ser Ala
            260                 265                 270

Val Pro Asn Gln Ile Ser Ile Ser Trp Ala Ser Glu Ile Gly Lys Asn
    275                 280                 285

Tyr Ser Met Ser Val Tyr Leu Val Arg Gln Leu Thr Ser Ala Met Leu
    290                 295                 300

Leu Gln Arg Leu Lys Met Lys Gly Ile Arg Asn Pro Asp His Ser Lys
305                 310                 315                 320

Ala Leu Ile Lys Glu Lys Leu Thr Ala Asp Pro Asp Ser Glu Ile Ala
                325                 330                 335

Thr Thr Ser Leu Arg Val Ser Leu Met Cys Pro Leu Gly Lys Met Arg
            340                 345                 350

Leu Thr Ile Pro Cys Arg Ala Val Thr Cys Thr His Leu Gln Cys Phe
        355                 360                 365

Asp Ala Ala Leu Tyr Leu Gln Met Asn Glu Lys Lys Pro Thr Trp Ile
    370                 375                 380

Cys Pro Val Cys Asp Lys Lys Ala Ala Tyr Glu Ser Leu Ile Leu Asp
385                 390                 395                 400

Gly Leu Phe Met Glu Ile Leu Asn Asp Cys Ser Asp Val Asp Glu Ile
                405                 410                 415
```

-continued

Lys Phe Gln Glu Asp Gly Ser Trp Cys Pro Met Arg Pro Lys Lys Glu
            420                 425                 430

Ala Met Lys Val Thr Ser Gln Pro Cys Thr Lys Val Glu Ser Ser Ser
            435                 440                 445

Val Phe Ser Lys Pro Cys Ser Val Thr Val Ala Ser Asp Ala Ser Lys
        450                 455                 460

Lys Lys Ile Asp Val Ile Asp Leu Thr Ile Glu Ser Ser Ser Asp Glu
465                 470                 475                 480

Glu Glu Asp Pro Pro Ala Lys Arg Lys Cys Ile Phe Met Ser Glu Thr
            485                 490                 495

Gln Ser Ser Pro Thr Lys Gly Val Leu Met Tyr Gln Pro Ser Ser Val
            500                 505                 510

Arg Val Pro Ser Val Thr Ser Val Asp Pro Ala Ala Ile Pro Pro Ser
        515                 520                 525

Leu Thr Asp Tyr Ser Val Pro Phe His His Thr Pro Val Ser Ser Met
    530                 535                 540

Ser Ser Asp Leu Pro Gly Leu Asp Phe Leu Ser Leu Ile Pro Val Asp
545                 550                 555                 560

Pro Gln Ser His Leu Thr Leu Asn Ser Lys Gln Tyr Val Cys His His
            565                 570                 575

His Gln Pro Pro
        580

<210> SEQ ID NO 37
<211> LENGTH: 1251
<212> TYPE: DNA
<213> ORGANISM: Homo sapien

<400> SEQUENCE: 37

```
atgagcacca agcagatcac ttgcaggtat tttatgcatg gtgtgtgtcg ggaaggaagt      60
cagtgcctat tctcacatga cttggcaaac agcaaaccgt ccaccatctg caagtactac     120
cagaagggct actgtgccta tggaactcgg tgcagatatg accacacgag ccctctgct      180
gcagctggag gtgctgtggg caccatggcc cacagtgtgc cctccccagc tttccacagt     240
cctcaccctc cttccgaggt cactgcatcc attgtgaaaa ctaactcaca tgaacccgga     300
aagcgtgaaa agagaacatt ggttcttaga gaccgaaatc tctctggcat ggctgaaagg     360
aagacccagc cgagcatggt gagtaatcca ggcagctgca gcgaccccca gcccagcccc     420
gagatgaagc gcattcctcc ctggatgcca tcaggagtg gccttgatga cgtggaggcc      480
agcagctcct acagcaacga gcagcagctg tgcccctacg cagctgctgg ggagtgccgg     540
tttggggatg cctgtgtcta cctgcacggg gaggtgtgtg aaatctgtag gctgcaagtc     600
ttgcacccat cgacccaga gcagaggaag gctcatgaaa agatctgcat gttgacgttc      660
gaacacgaga tggaaaaggc ctttgccttc caggcaagcc aggacaaagt gtgcagtatc     720
tgcatggaag tgatcctgga gaaggcctct gcttctgaga ggagatttgg gattctctcc     780
aattgcaatc acacgtactg tttgtcctgc atccggcagt ggcggtgtgc cgaacagttt     840
gaaaacccaa tcattaagtc ttgtccagaa tgccgtgtga tatcagagtt tgtaattcca     900
agtgtgtatt gggtggaaga tcagaataaa agaacgagt tgattgaagc tttcaaacag     960
gggatgggga aaaagcctg taaatacttt gagcaaggca aggggacctg cccatttgga    1020
agcaaatgtc tttatcgcca tgcttacccc gatgggcggc tagcagagcc tgagaaacct    1080
cggaaacagc tcagttctca aggcactgtg aggttcttta attcagtgcg gctctgggat    1140
```

```
ttcatcgaga accgagaaag ccggcatgtc cccaacaatg aagatgtcga catgacagag    1200
ctcggggacc tcttcatgca cctttctgga gtggaatcat cagaacccta a             1251
```

<210> SEQ ID NO 38
<211> LENGTH: 416
<212> TYPE: PRT
<213> ORGANISM: Homo sapien

<400> SEQUENCE: 38

```
Met Ser Thr Lys Gln Ile Thr Cys Arg Tyr Phe Met His Gly Val Cys
 1               5                  10                  15

Arg Glu Gly Ser Gln Cys Leu Phe Ser His Asp Leu Ala Asn Ser Lys
            20                  25                  30

Pro Ser Thr Ile Cys Lys Tyr Tyr Gln Lys Gly Tyr Cys Ala Tyr Gly
        35                  40                  45

Thr Arg Cys Arg Tyr Asp His Thr Arg Pro Ser Ala Ala Ala Gly Gly
    50                  55                  60

Ala Val Gly Thr Met Ala His Ser Val Pro Ser Pro Ala Phe His Ser
65                  70                  75                  80

Pro His Pro Pro Ser Glu Val Thr Ala Ser Ile Val Lys Thr Asn Ser
                85                  90                  95

His Glu Pro Gly Lys Arg Glu Lys Arg Thr Leu Val Leu Arg Asp Arg
            100                 105                 110

Asn Leu Ser Gly Met Ala Glu Arg Lys Thr Gln Pro Ser Met Val Ser
        115                 120                 125

Asn Pro Gly Ser Cys Ser Asp Pro Gln Pro Ser Pro Glu Met Lys Pro
    130                 135                 140

His Ser Tyr Leu Asp Ala Ile Arg Ser Gly Leu Asp Asp Val Glu Ala
145                 150                 155                 160

Ser Ser Ser Tyr Ser Asn Glu Gln Gln Leu Cys Pro Tyr Ala Ala Ala
                165                 170                 175

Gly Glu Cys Arg Phe Gly Asp Ala Cys Val Tyr Leu His Gly Glu Val
            180                 185                 190

Cys Glu Ile Cys Arg Leu Gln Val Leu His Pro Phe Asp Pro Glu Gln
        195                 200                 205

Arg Lys Ala His Glu Lys Ile Cys Met Leu Thr Phe Glu His Glu Met
    210                 215                 220

Glu Lys Ala Phe Ala Phe Gln Ala Ser Gln Asp Lys Val Cys Ser Ile
225                 230                 235                 240

Cys Met Glu Val Ile Leu Glu Lys Ala Ser Ala Ser Glu Arg Arg Phe
                245                 250                 255

Gly Ile Leu Ser Asn Cys Asn His Thr Tyr Cys Leu Ser Cys Ile Arg
            260                 265                 270

Gln Trp Arg Cys Ala Glu Gln Phe Glu Asn Pro Ile Ile Lys Ser Cys
        275                 280                 285

Pro Glu Cys Arg Val Ile Ser Glu Phe Val Ile Pro Ser Val Tyr Trp
    290                 295                 300

Val Glu Asp Gln Asn Lys Lys Asn Glu Leu Ile Glu Ala Phe Lys Gln
305                 310                 315                 320

Gly Met Gly Lys Lys Ala Cys Lys Tyr Phe Glu Gln Gly Lys Gly Thr
                325                 330                 335

Cys Pro Phe Gly Ser Lys Cys Leu Tyr Arg His Ala Tyr Pro Asp Gly
            340                 345                 350
```

```
Arg Leu Ala Glu Pro Glu Lys Pro Arg Lys Gln Leu Ser Ser Gln Gly
            355                 360                 365

Thr Val Arg Phe Phe Asn Ser Val Arg Leu Trp Asp Phe Ile Glu Asn
        370                 375                 380

Arg Glu Ser Arg His Val Pro Asn Asn Glu Asp Val Asp Met Thr Glu
385                 390                 395                 400

Leu Gly Asp Leu Phe Met His Leu Ser Gly Val Glu Ser Ser Glu Pro
                405                 410                 415
```

<210> SEQ ID NO 39
<211> LENGTH: 738
<212> TYPE: DNA
<213> ORGANISM: Homo sapien

<400> SEQUENCE: 39

```
atgaaacgga ggaagcaaga tgaagggcag agggaaggct cctgcatggc tgaggatgat      60
gctgtggaca tcgagcatga gaacaacaac cgctttgagg agtatgagtg gtgtggacag     120
aagcggatac gggccaccac tctcctggaa ggtggcttcc gaggctctgg cttcatcatg     180
tgcagcggca agagaacccc ggacagtgat gctgacttgg atgtggatgg ggatgacact     240
ctggagtatg gaagccaca atacacagag gctgatgtca tccctgcac aggcgaggag     300
cctggtgaag ccaaggagag agaggcactt cggggcgcag tcctaaatgg cggccctccc     360
agcacgcgca tcacacctga gttctctaaa tgggccagtg atgagatgcc atccaccagc     420
aatggtgaaa gcagcaagca ggaggccatg cagaagacct gcaagaacag cgacatcgag     480
aaaatcaccg aagattcagc tgtgaccacg tttgaggctc tgaaggctcg ggtcagagaa     540
cttgaacggc agctatctcg tggggaccgt tacaaatgcc tcatctgcat ggactcgtac     600
tcgatgcccc taacgtccat ccagtgttgg cacgtgcact gcgaggagtg ctggctgcgg     660
accctgggtg ccaagaagct ctgccctcag tgcaacacga tcacagcgcc cggagacctg     720
cggaggatct acttgtga                                                    738
```

<210> SEQ ID NO 40
<211> LENGTH: 245
<212> TYPE: PRT
<213> ORGANISM: Homo sapien

<400> SEQUENCE: 40

```
Met Lys Arg Arg Lys Gln Asp Glu Gly Gln Arg Glu Gly Ser Cys Met
  1               5                  10                  15

Ala Glu Asp Asp Ala Val Asp Ile Glu His Glu Asn Asn Asn Arg Phe
                20                  25                  30

Glu Glu Tyr Glu Trp Cys Gly Gln Lys Arg Ile Arg Ala Thr Thr Leu
            35                  40                  45

Leu Glu Gly Gly Phe Arg Gly Ser Gly Phe Ile Met Cys Ser Gly Lys
        50                  55                  60

Glu Asn Pro Asp Ser Asp Ala Asp Leu Asp Val Asp Gly Asp Asp Thr
 65                 70                  75                  80

Leu Glu Tyr Gly Lys Pro Gln Tyr Thr Glu Ala Asp Val Ile Pro Cys
                85                  90                  95

Thr Gly Glu Glu Pro Gly Glu Ala Lys Glu Arg Glu Ala Leu Arg Gly
            100                 105                 110

Ala Val Leu Asn Gly Gly Pro Pro Ser Thr Arg Ile Thr Pro Glu Phe
        115                 120                 125
```

```
Ser Lys Trp Ala Ser Asp Glu Met Pro Ser Thr Ser Asn Gly Glu Ser
    130                 135                 140

Ser Lys Gln Glu Ala Met Gln Lys Thr Cys Lys Asn Ser Asp Ile Glu
145                 150                 155                 160

Lys Ile Thr Glu Asp Ser Ala Val Thr Thr Phe Glu Ala Leu Lys Ala
                165                 170                 175

Arg Val Arg Glu Leu Glu Arg Gln Leu Ser Arg Gly Asp Arg Tyr Lys
            180                 185                 190

Cys Leu Ile Cys Met Asp Ser Tyr Ser Met Pro Leu Thr Ser Ile Gln
        195                 200                 205

Cys Trp His Val His Cys Glu Glu Cys Trp Leu Arg Thr Leu Gly Ala
    210                 215                 220

Lys Lys Leu Cys Pro Gln Cys Asn Thr Ile Thr Ala Pro Gly Asp Leu
225                 230                 235                 240

Arg Arg Ile Tyr Leu
                245

<210> SEQ ID NO 41
<211> LENGTH: 1425
<212> TYPE: DNA
<213> ORGANISM: Homo sapien

<400> SEQUENCE: 41
atgtcgtcag aagatcgaga agctcaggag gatgaattgc tggccctggc aagtatttac      60
gatggagatg aatttagaaa agcagagtct gtccaaggtg gagaaaccag gatctatttg     120
gatttgccac agaatttcaa gatatttgtg agcggcaatt caaatgagtg tctccagaat     180
agtggctttg aataccacca ttgctttctg cctccacttg tgctgaactt tgaactgcca     240
ccagattatc atcctcttc cccaccttca ttcacactta gtggcaaatg gctgtcacca     300
actcagctat ctgctctatg caagcactta gacaacctat gggaagaaca ccgtggcagc     360
gtggtcctgt ttgcctggat gcaatttctt aaggaagaga ccctagcata cttgaatatt     420
gtctctcctt ttgagctcaa gattggttct cagaaaaaag tgcagagaag gacagctcaa     480
gcttctccca acacagagct agattttgga ggagctgctg gatctgatgt agaccaagag     540
gaaattgtgg atgagagagc agtgcaggat gtggaatcac tgtcaaatct gatccaggaa     600
atcttggact tgatcaagc tcagcagata aaatgcttta atagtaaatt gttcctgtgc     660
agtatctgtt tctgtgagaa gctgggtagt gaatgcatgt acttcttgga gtgcaggcat     720
gtgtactgca aagcctgtct gaaggactac tttgaaatcc agatcagaga tggccaggtt     780
caatgcctca actgcccaga accaaagtgc ccttcggtgg ccactcctgg tcaggtcaaa     840
gagttagtgg aagcagagtt atttgcccgt tatgaccgcc ttctcctcca gtcctccttg     900
gacctgatgg cagatgtggt gtactgcccc cggccgtgct gccagctgcc tgtgatgcag     960
gaacctggct gcaccatggg tatctgctcc agctgcaatt ttgccttctg tactttgtgc    1020
aggttgacct accatggggt ctccccatgt aaggtgactg cagagaaatt aatggactta    1080
cgaaatgaat acctgcaagc ggatgaggct aataaaagac ttttggatca aggtatggt     1140 aagagagtga ttcagaaggc actggaagag atgaaagta aggagtggct agagaagaac    1200
tcaaagagct gccatgttg tggaactccc atagagaaat tagacggatg taacaagatg    1260
acatgtactg gctgtatgca atatttctgt tggatttgca tgggttctct ctctagagca    1320 aaccccttaca aacatttcaa tgaccctggt tcaccatgtt ttaaccggct gttttatgct    1380
gtggatgttg acgacgatat ttgggaagat gaggtagaag actag                    1425
```

<210> SEQ ID NO 42
<211> LENGTH: 474
<212> TYPE: PRT
<213> ORGANISM: Homo sapien

<400> SEQUENCE: 42

```
Met Ser Ser Glu Asp Arg Glu Ala Gln Glu Asp Leu Leu Ala Leu
 1               5                  10                  15

Ala Ser Ile Tyr Asp Gly Asp Glu Phe Arg Lys Ala Glu Ser Val Gln
             20                  25                  30

Gly Gly Glu Thr Arg Ile Tyr Leu Asp Leu Pro Gln Asn Phe Lys Ile
         35                  40                  45

Phe Val Ser Gly Asn Ser Asn Glu Cys Leu Gln Asn Ser Gly Phe Glu
     50                  55                  60

Tyr Thr Ile Cys Phe Leu Pro Pro Leu Val Leu Asn Phe Glu Leu Pro
 65                  70                  75                  80

Pro Asp Tyr Pro Ser Ser Pro Pro Ser Phe Thr Leu Ser Gly Lys
                 85                  90                  95

Trp Leu Ser Pro Thr Gln Leu Ser Ala Leu Cys Lys His Leu Asp Asn
                100                 105                 110

Leu Trp Glu Glu His Arg Gly Ser Val Val Leu Phe Ala Trp Met Gln
            115                 120                 125

Phe Leu Lys Glu Glu Thr Leu Ala Tyr Leu Asn Ile Val Ser Pro Phe
        130                 135                 140

Glu Leu Lys Ile Gly Ser Gln Lys Lys Val Gln Arg Arg Thr Ala Gln
145                 150                 155                 160

Ala Ser Pro Asn Thr Glu Leu Asp Phe Gly Ala Ala Gly Ser Asp
                165                 170                 175

Val Asp Gln Glu Glu Ile Val Asp Glu Arg Ala Val Gln Asp Val Glu
                180                 185                 190

Ser Leu Ser Asn Leu Ile Gln Glu Ile Leu Asp Phe Asp Gln Ala Gln
            195                 200                 205

Gln Ile Lys Cys Phe Asn Ser Lys Leu Phe Leu Cys Ser Ile Cys Phe
        210                 215                 220

Cys Glu Lys Leu Gly Ser Glu Cys Met Tyr Phe Leu Glu Cys Arg His
225                 230                 235                 240

Val Tyr Cys Lys Ala Cys Leu Lys Asp Tyr Phe Glu Ile Gln Ile Arg
                245                 250                 255

Asp Gly Gln Val Gln Cys Leu Asn Cys Pro Glu Pro Lys Cys Pro Ser
            260                 265                 270

Val Ala Thr Pro Gly Gln Val Lys Glu Leu Val Glu Ala Glu Leu Phe
        275                 280                 285

Ala Arg Tyr Asp Arg Leu Leu Leu Gln Ser Ser Leu Asp Leu Met Ala
    290                 295                 300

Asp Val Val Tyr Cys Pro Arg Pro Cys Gln Leu Pro Val Met Gln
305                 310                 315                 320

Glu Pro Gly Cys Thr Met Gly Ile Cys Ser Ser Cys Asn Phe Ala Phe
                325                 330                 335

Cys Thr Leu Cys Arg Leu Thr Tyr His Gly Val Ser Pro Cys Lys Val
            340                 345                 350

Thr Ala Glu Lys Leu Met Asp Leu Arg Asn Glu Tyr Leu Gln Ala Asp
        355                 360                 365

Glu Ala Asn Lys Arg Leu Leu Asp Gln Arg Tyr Gly Lys Arg Val Ile
    370                 375                 380
```

```
Gln Lys Ala Leu Glu Glu Met Glu Ser Lys Glu Trp Leu Glu Lys Asn
385                 390                 395                 400

Ser Lys Ser Cys Pro Cys Cys Gly Thr Pro Ile Glu Lys Leu Asp Gly
            405                 410                 415

Cys Asn Lys Met Thr Cys Thr Gly Cys Met Gln Tyr Phe Cys Trp Ile
            420                 425                 430

Cys Met Gly Ser Leu Ser Arg Ala Asn Pro Tyr Lys His Phe Asn Asp
        435                 440                 445

Pro Gly Ser Pro Cys Phe Asn Arg Leu Phe Tyr Ala Val Asp Val Asp
    450                 455                 460

Asp Asp Ile Trp Glu Asp Glu Val Glu Asp
465                 470

<210> SEQ ID NO 43
<211> LENGTH: 6
<212> TYPE: PRT
<213> ORGANISM: Artificial Sequence
<220> FEATURE:
<223> OTHER INFORMATION: nuclear localization signal

<400> SEQUENCE: 43

His Lys Ala Val Lys Arg
1               5

<210> SEQ ID NO 44
<211> LENGTH: 7
<212> TYPE: PRT
<213> ORGANISM: Artificial Sequence
<220> FEATURE:
<223> OTHER INFORMATION: nuclear localization signal

<400> SEQUENCE: 44

Arg Leu Lys Ile Thr Lys Lys
1               5

<210> SEQ ID NO 45
<211> LENGTH: 6
<212> TYPE: PRT
<213> ORGANISM: Artificial Sequence
<220> FEATURE:
<223> OTHER INFORMATION: putative protein kinase phosphorylation site

<400> SEQUENCE: 45

Arg Pro Arg Ser Phe Thr
1               5

<210> SEQ ID NO 46
<211> LENGTH: 7
<212> TYPE: PRT
<213> ORGANISM: Artificial Sequence
<220> FEATURE:
<223> OTHER INFORMATION: protein kinase phosphorylation site consensus
      sequence
<221> NAME/KEY: VARIANT
<222> LOCATION: 2, 4, 5
<223> OTHER INFORMATION: Xaa = any amino acid

<400> SEQUENCE: 46

Arg Xaa Arg Xaa Xaa Ser Thr
1               5

<210> SEQ ID NO 47
<211> LENGTH: 24
<212> TYPE: PRT
<213> ORGANISM: Artificial Sequence
```

```
-continued

<220> FEATURE:
<223> OTHER INFORMATION: consensus sequence
<221> NAME/KEY: VARIANT
<222> LOCATION: 3, 5, 8, 10, 12, 15, 16, 17, 19, 20, 21, 22
<223> OTHER INFORMATION: Xaa = any amino acid

<400> SEQUENCE: 47

Ser Thr Xaa Pro Xaa Ser Pro Xaa Ser Xaa Pro Xaa Ser Pro Xaa Xaa
1               5                   10                  15

Xaa Gly Xaa Xaa Xaa Xaa Ser Asp
            20

<210> SEQ ID NO 48
<211> LENGTH: 9
<212> TYPE: PRT
<213> ORGANISM: Artificial Sequence
<220> FEATURE:
<223> OTHER INFORMATION: neuralized homology repeat domain

<400> SEQUENCE: 48

Leu Pro Lys Tyr Ala Cys Pro Asp Leu
1               5
```